(12) United States Patent
Schwarz

(10) Patent No.: US 10,428,093 B2
(45) Date of Patent: Oct. 1, 2019

(54) LIPID CO-FACTOR ESSENTIAL FOR CELL DENSITY SIGNALING

(71) Applicant: Richard I. Schwarz, Oakland, CA (US)

(72) Inventor: Richard I. Schwarz, Oakland, CA (US)

( * ) Notice: Subject to any disclaimer, the term of this patent is extended or adjusted under 35 U.S.C. 154(b) by 35 days.

(21) Appl. No.: 15/137,448

(22) Filed: Apr. 25, 2016

(65) Prior Publication Data

US 2016/0251386 A1   Sep. 1, 2016

Related U.S. Application Data

(60) Provisional application No. 61/896,604, filed on Oct. 28, 2013.

(51) Int. Cl.
| | | |
|---|---|---|
| *C07F 9/572* | (2006.01) |
| *C07K 14/47* | (2006.01) |
| *B01D 61/14* | (2006.01) |
| *C07K 14/465* | (2006.01) |
| *B01D 61/16* | (2006.01) |
| *C07K 16/18* | (2006.01) |

(52) U.S. Cl.
CPC ............ *C07F 9/572* (2013.01); *B01D 61/145* (2013.01); *B01D 61/16* (2013.01); *C07K 14/465* (2013.01); *C07K 14/47* (2013.01); *C07K 14/4705* (2013.01); *C07K 16/18* (2013.01)

(58) Field of Classification Search
CPC .. C07K 9/572; C07K 14/4705; C07K 14/465; C07K 14/47; B01D 61/145
See application file for complete search history.

(56) References Cited

PUBLICATIONS

Taylor et al., Enhanced potency of human sonic hedgehog by hydrophobic modification. Biochemistry 40:4359-4371, 2001.*

* cited by examiner

*Primary Examiner* — Ruixiang Li

(57) ABSTRACT

Herein is described a cell density signaling protein and its tissue-specific lipid cofactor. Constructs, compositions and methods for isolation, purification and use of the protein and the tissue-specific lipid cofactor are described.

4 Claims, 16 Drawing Sheets

Specification includes a Sequence Listing.

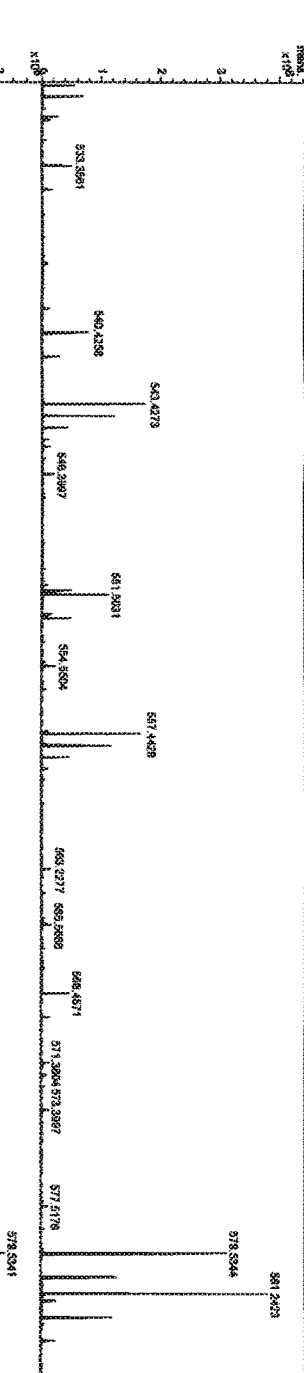
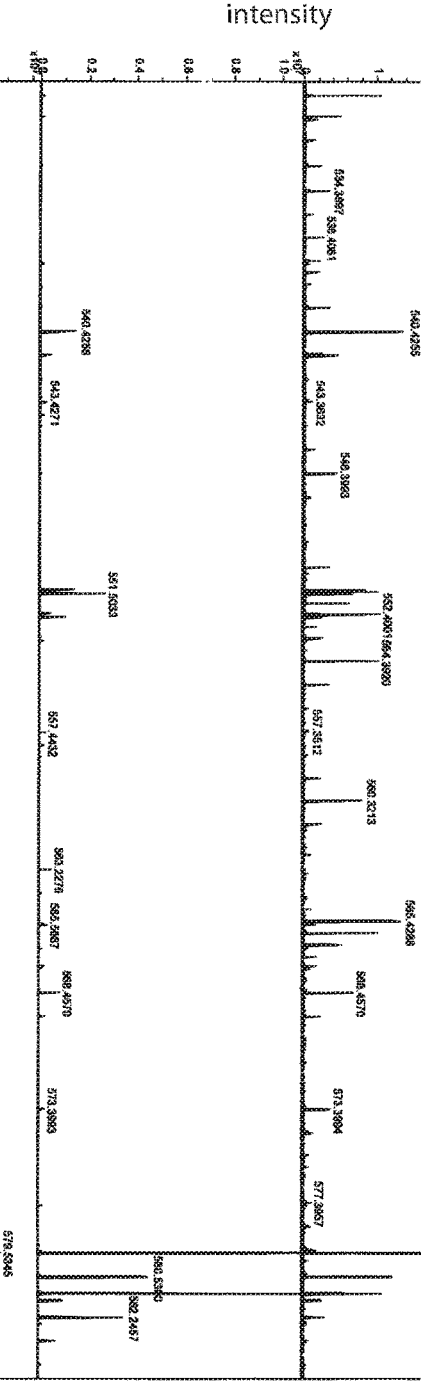
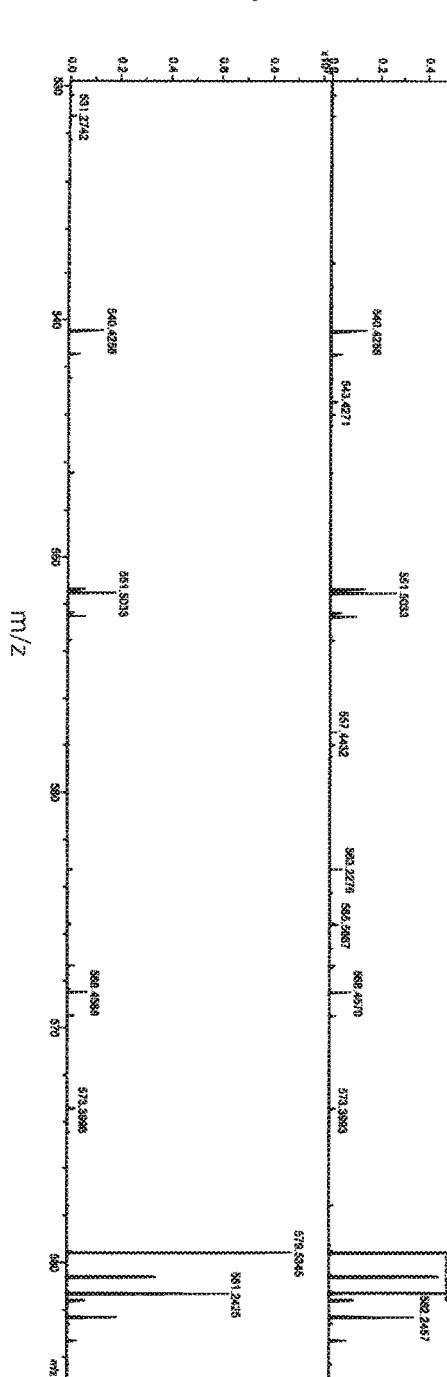
Fig. 8A untreated cofactor
Fig. 8B phospholipase C
Fig. 8C lipase
Fig. 8D no cofactor buffer only

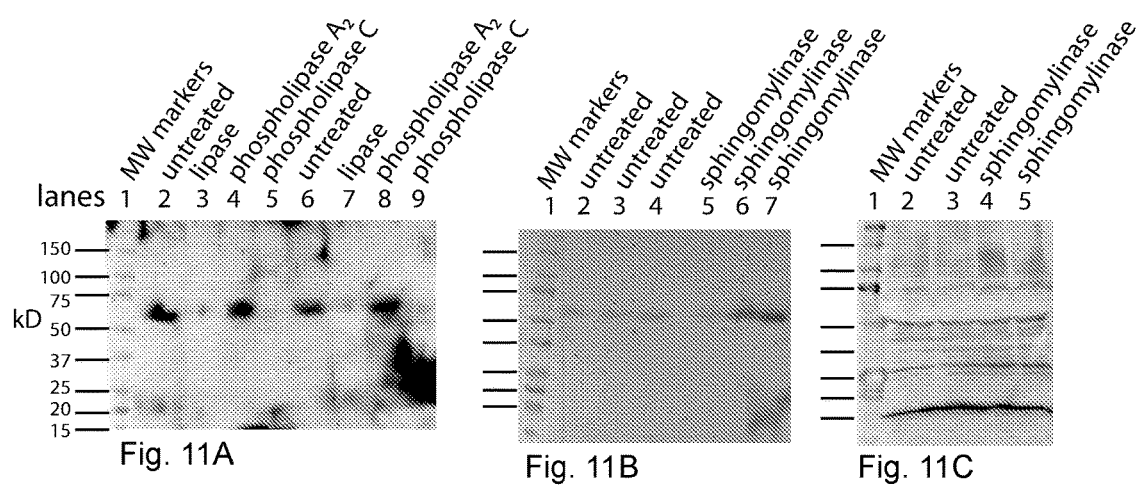

6 day control 6 day 5X CM U2OS-pESY1c 6 day 5 μg/ml E. coli-pESY1c 6 day 5X CM PAT 15 day control 15 day 5X CM U2OS-pESY1c polyclonal antibody

DAPI preimmune serum

DAPI

SEQUENCE LISTING

<160> NUMBER OF SEQ ID NOS: 17

<210> SEQ ID NO 1
<211> LENGTH: 8
<212> TYPE: PRT
<213> ORGANISM: Gallus gallus
<220> FEATURE:
<221> NAME/KEY: MISC_FEATURE
<222> LOCATION: (1)..(8)
<223> OTHER INFORMATION: First 8 amino acids of CDS sequence identified
      in US Patent No. 6433136

<400> SEQUENCE: 1

Glu Pro Leu Ala Val Val Asp Leu
1               5

<210> SEQ ID NO 2
<211> LENGTH: 14
<212> TYPE: PRT
<213> ORGANISM: Gallus gallus
<220> FEATURE:
<221> NAME/KEY: MISC_FEATURE
<222> LOCATION: (1)..(14)
<223> OTHER INFORMATION: 14 amino acid CDS sequence identified in US
      Patent No. 6433136

<400> SEQUENCE: 2

Glu Pro Leu Ala Val Val Asp Leu Thr Glu Lys Thr Ile Ser
1               5                   10

<210> SEQ ID NO 3
<211> LENGTH: 94
<212> TYPE: PRT
<213> ORGANISM: Gallus gallus

<400> SEQUENCE: 3

Glu Pro Leu Ala Val Val Asp Leu Arg Pro Gln Ser Ser Val Lys Val
1               5                   10                  15

Glu Val His Phe Gln Asp Lys Val Glu Glu Met Ser Ile Arg Leu Asp
            20                  25                  30

Gln Thr Val Ala Glu Leu Lys Lys His Leu Lys Thr Val Val Gln Leu
        35                  40                  45

Ser Thr Ser Asn Met Leu Leu Phe Tyr Leu Asp Gln Glu Ala Pro Phe
            50                  55                  60

Gly Pro Glu Glu Met Lys Tyr Ser Ser Arg Ala Leu His Ser Tyr Gly
 65                  70                  75                  80

Ile Arg Asp Gly Asp Lys Ile Tyr Val Glu Pro Arg Met Lys
                85                  90

<210> SEQ ID NO 4
<211> LENGTH: 89
<212> TYPE: PRT
<213> ORGANISM: Artificial sequence
<220> FEATURE:
<223> OTHER INFORMATION: 94 aa cell density signal consensus -
      artificial sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (87)..(88)
<223> OTHER INFORMATION: Xaa can be any naturally occurring amino acid

<400> SEQUENCE: 4

Glu Pro Leu Ala Xaa Val Asp Leu Arg Pro Gln Ser Ser Xaa Lys Val
 1               5                  10                  15

Glu Val His Phe Xaa Asp Val Glu Glu Met Ser Ile Arg Leu Asp Gln
                20                  25                  30

Thr Val Ala Glu Leu Lys Lys Xaa Leu Lys Thr Val Gln Leu Xaa Thr
            35                  40                  45

Ser Asn Met Leu Leu Tyr Xaa Asp Xaa Glu Ala Pro Phe Gly Pro Glu
        50                  55                  60

Glu Met Lys Tyr Ser Ser Arg Ala Leu His Ser Gly Ile Arg Asp Gly
 65                  70                  75                  80

Asp Lys Ile Tyr Val Glu Xaa Xaa Lys
                85

<210> SEQ ID NO 5
<211> LENGTH: 94
<212> TYPE: PRT
<213> ORGANISM: Homo sapiens

<400> SEQUENCE: 5

Glu Pro Leu Ala Glu Val Asp Leu Arg Pro Gln Ser Ser Ala Lys Val

```
              1               5                  10                 15
           Glu Val His Phe Asn Asp Gln Val Glu Met Ser Ile Arg Leu Asp
                         20                  25                 30
           Gln Thr Val Ala Glu Leu Lys Lys Gln Leu Lys Thr Leu Val Gln Leu
                             35                  40                  45
           Pro Thr Ser Asn Met Leu Leu Tyr Tyr Phe Asp His Glu Ala Pro Phe
                   50                  55                  60
           Gly Pro Glu Glu Met Lys Tyr Ser Ser Arg Ala Leu His Ser Phe Gly
           65                  70                  75                  80
           Ile Arg Asp Gly Asp Lys Ile Tyr Val Glu Ser Lys Thr Lys
                               85                  90

<210> SEQ ID NO 6
<211> LENGTH: 1781
<212> TYPE: DNA
<213> ORGANISM: Homo sapiens

<400> SEQUENCE: 6
acactgggct ccggcggcca gagtggggga ctaggtgaag cggcgccggg ccggggctgg      60
ccgggaccag gcccgaggct gagcggcggc gacagcggtg gccgggaggg gggaggagag     120
gcgcagccag aggagccgcc gcagtagctc ccccgcctcc cgggctgagg gcattttaag     180
aaagaaagat ggatcaacct agtggaagaa gtttcatgca agtattatgt gaaaaatata     240
gtcctgaaaa ttttccttat cgccgtggcc cggggatggg agtccatgtc ccagccacac     300
ctcagggctc tcctatgaaa gatcgcctca acctcccaag tgtactagtg ttgaacagct     360
gtggaataac ctgtgcagga gatgaaaaag aaattgctgc tttctgcgct catgtgtcgg     420
aactagatct ttctgacaac aaactcgaag actggcatga ggtcagtaaa attgtgtcaa     480
atgttcctca gttggagttt ctaaacctga gttccaaccc tctgaatttg tcggttttag     540
aaagaacatg tgctgggtcc ttctctgggg ttcgcaaact tgtcctcaac aacagcaaag     600
cttcttggga cggtccac atgatactac aggagttacc agatttggag gagctcttcc      660
tgtgccttaa tgactatgaa acagtgtctt gtccttctat ttgctgtcat tctcttaagc     720
tactacatat aacagacaat aacctccaag actggactga aatacgaaag ttaggagtta     780
tgtttccttc actggatacc ctcgtcctgg ccaacaatca tttgaatgct attgaggagc     840
ctgatgattc attggccagg ttggttccta atcttcgatc catcagcctc cacaggtcag     900
gtttgcagtc ctgggaagac attgataaac taaattcatt tcccaaactg gaagaagtga     960
gattgttagg aattcctctt ctgcagccat ataccaccga ggagcgaagg aaattggtaa    1020
tagccagatt gccatcagtt tccaaactta atggcagcgt tgttactgat ggtgaacgag    1080
aagattctga gattttttt attcgttact atgtggatgt tccacaggaa gaagtgccat    1140
tcaggtatca tgaactgatc actaaatatg ggaagttgga gcctttgaca gaagtggacc    1200
taagacccca gagcagtgca aaagtagaag tccactttaa cgatcaggtg aagaaatga    1260
gcattcgtct ggaccaaaca gtggcagaac taaagaaaca gttaaaaact ctagtacaat    1320
tacccacaag caacatgctt ctctactatt ttgaccatga agcaccctt ggcccagagg    1380
aaatgaagta cagctctcgg gcattgcatt cctttggcat tagggatgga gataaatttt    1440
acgtggaatc caaaacaaaa taacctctac cagccttgtg aaaaacatac acataaggac    1500
ttgttgcagg gcatttgttt ttaatgtggt tttcttagg agggagaggt tgttttgtt    1560
ttgtttgtt ctgtttaggt ttgggaagga ttttgtatat ttttcccct ggagtgagta    1620
```

```
ggggccattt ttgggtgttt tctaccacag attgatttgg ctcagccagc ggaattggcc    1680
acatttccag tgtatgtgcc ctctctaagg aaagatgaca agaaatcac cgacttctta    1740 ctgtgttcac tgggatttgc ctgccacgtt ggtatcagta c                        1781
```

<210> SEQ ID NO 7
<211> LENGTH: 424
<212> TYPE: PRT
<213> ORGANISM: Homo sapiens

<400> SEQUENCE: 7

```
Met Asp Gln Pro Ser Gly Arg Ser Phe Met Gln Val Leu Cys Glu Lys
1               5                   10                  15

Tyr Ser Pro Glu Asn Phe Pro Tyr Arg Arg Gly Pro Gly Met Gly Val
                20                  25                  30

His Val Pro Ala Thr Pro Gln Gly Ser Pro Met Lys Asp Arg Leu Asn
            35                  40                  45

Leu Pro Ser Val Leu Val Leu Asn Ser Cys Gly Ile Thr Cys Ala Gly
        50                  55                  60

Asp Glu Lys Glu Ile Ala Ala Phe Cys Ala His Val Ser Glu Leu Asp
65                  70                  75                  80

Leu Ser Asp Asn Lys Leu Glu Asp Trp His Glu Val Ser Lys Ile Val
                85                  90                  95

Ser Asn Val Pro Gln Leu Glu Phe Leu Asn Leu Ser Ser Asn Pro Leu
                100                 105                 110

Asn Leu Ser Val Leu Glu Arg Thr Cys Ala Gly Ser Phe Ser Gly Val
            115                 120                 125

Arg Lys Leu Val Leu Asn Asn Ser Lys Ala Ser Trp Glu Thr Val His
        130                 135                 140

Met Ile Leu Gln Glu Leu Pro Asp Leu Glu Glu Leu Phe Leu Cys Leu
145                 150                 155                 160

Asn Asp Tyr Glu Thr Val Ser Cys Pro Ser Ile Cys Cys His Ser Leu
                165                 170                 175

Lys Leu Leu His Ile Thr Asp Asn Asn Leu Gln Asp Trp Thr Glu Ile
            180                 185                 190

Arg Lys Leu Gly Val Met Phe Pro Ser Leu Asp Thr Leu Val Leu Ala
        195                 200                 205

Asn Asn His Leu Asn Ala Ile Glu Glu Pro Asp Ser Leu Ala Arg
210                 215                 220

Leu Val Pro Asn Leu Arg Ser Ile Ser Leu His Arg Ser Gly Leu Gln
225                 230                 235                 240

Ser Trp Glu Asp Ile Asp Lys Leu Asn Ser Phe Pro Lys Leu Glu Glu
                245                 250                 255

Val Arg Leu Leu Gly Ile Pro Leu Leu Gln Pro Tyr Thr Thr Glu Glu
            260                 265                 270

Arg Arg Lys Leu Val Ile Ala Arg Leu Pro Ser Val Ser Lys Leu Asn
        275                 280                 285

Gly Ser Val Val Thr Asp Gly Glu Arg Glu Asp Ser Glu Arg Phe Phe
    290                 295                 300

Ile Arg Tyr Tyr Val Asp Val Pro Gln Glu Glu Val Pro Phe Arg Tyr
305                 310                 315                 320

His Glu Leu Ile Thr Lys Tyr Gly Lys Leu Glu Pro Leu Thr Glu Val
                325                 330                 335

Asp Leu Arg Pro Gln Ser Ser Ala Lys Val Glu Val His Phe Asn Asp
            340                 345                 350
```

Gln Val Glu Glu Met Ser Ile Arg Leu Asp Gln Thr Val Ala Glu Leu
        355                 360                 365

Lys Lys Gln Leu Lys Thr Leu Val Gln Leu Pro Thr Ser Asn Met Leu
370                 375                 380

Leu Tyr Tyr Phe Asp His Glu Ala Pro Phe Gly Pro Glu Glu Met Lys
385                 390                 395                 400

Tyr Ser Ser Arg Ala Leu His Ser Phe Gly Ile Arg Asp Gly Asp Lys
                405                 410                 415

Ile Tyr Val Glu Ser Lys Thr Lys
        420

<210> SEQ ID NO 8
<211> LENGTH: 5395
<212> TYPE: DNA
<213> ORGANISM: Gallus gallus

<400> SEQUENCE: 8

| | |
|---|---|
| acgggggggc tatcacgtga tgtttggttg ctaccgagct gtttccgggt cgatgcggga | 60 |
| cgcggccgcc gggcctggaa gtccaagaaa ggagcatgga ccaacccagt ggcaggagtt | 120 |
| tcatgcaagt tctttgtgag aaatacagcc ctgagaactt cccgtatcgc cgcggccctg | 180 |
| gtatgggtgt gcacgtccca gcaactccac agggctcacc tatgaaagat cgtctcaacc | 240 |
| ttccaagcgt gctggtgctg aacagctgtg gcataacctg tgcaggggat gagaacgaga | 300 |
| ttgctgcctt ctgtgctcac gtctccgaac tcgatctttc tgacaataaa ctggaagact | 360 |
| ggcacgaggt cagtaaaatt gtgtccaacg ttccccactt ggagtttcta aacttgagtt | 420 |
| ccaatcctct cagtttgtcc gttctagaga aaggtgtgc tgggtccttc gctggtgtcc | 480 |
| gcaaacttgt gctcaacaac agcaaagctt cctgggaaac agtccacaca atcctgcagg | 540 |
| agttacctga cttggaggag ctcttcctgt gccttaatga ctacgaaaca gtgtcttgtt | 600 |
| ctccagtttg ctgtcagtct ctcaaattac tccacataac tgacaataac cttcaagact | 660 |
| ggactgaaat tcgaaaattg gcattatgt ttccatctct ggacacccctt attctggcta | 720 |
| acaacaacct caccaccatc gaagagtcgg aagattccct cgcaaggctg ttccccaacc | 780 |
| tgcgatccat caatttgcac aagtcaggtc tgcattgctg ggaagacatt gacaagttaa | 840 |
| attcgttccc caagcttgag gaagtgaaat tgctaggaat ccctttgctg cagtcctaca | 900 |
| ccactgagga gcgcaggaag ctgctaatag ccaggttgcc atctatcatc aagctcaacg | 960 |
| ggagcattgt tggtgatggg gagcgagagg actcggagcg attcttcatc cgatattaca | 1020 |
| tggagttccc agaggaggaa gtcccattca ggtaccacga gctgatcacc aagtatggga | 1080 |
| agctggagcc cttggcagtc gtggatcttc ggccgcagag cagtgtgaag gtggaggttc | 1140 |
| acttccagga caaagtagaa gagatgtcaa tccgtcttga tcagactgtg gcagaactga | 1200 |
| agaagcactt aaaaactgtg gtgcagctgt caaccagcaa catgctgctc ttctacttgg | 1260 |
| accaggaagc cccttcggc cccgaggaga tgaagtacag ctcacgagca ctgcattcct | 1320 |
| atggcattcg ggatggagac aaaatctatg tggagcccag gatgaagtag cctctctcga | 1380 |
| cctacacagc ccacacaccc acacgtgc atttaaggag ttttgcaag gttttattt | 1440 |
| cggtcagttg gttgaggttt ggttgtgttt ctatagcagg taatggctta gcccggagcg | 1500 |
| agtgccctga tgacagaacc atgcccacca cccactgcag gtgacctcgg ggtgacgact | 1560 |
| gacttcagtg catgtgtttc cgtgtgtgca ataccccccat gttttctttg atgctccggt | 1620 |
| atactcgtga tttggcatga gtggtcagtt attgaagctg aagaatgcta gggcccgtaa | 1680 |

```
gggagaggat ggctcggtgc agaatttgac ctatttattt ctctttctct aaaaaacatg    1740
ggttttttt ttggcaccat cagagcaccc cagctatcca actgcagttt gagcgagctt     1800
ggttttccat ctgggtgctg tcttgtagcc ttttgtcaca ctcaagctca ctgaaaagat    1860
ctgaaataat gttcagtttg aatcagagct caggtattca gtattcagcg catccactta   1920
gctccactgg ttggtgtgag cgcacaagat gagggaaaga cagggatgct atgagaaaga   1980
aaggatttct tttaaaaact catgcttcta gccatgctgt cttatcagga gtttggaggt   2040
ttgctttctg tgtccgtgtc acggtgtctg caacctgtag cactgtcagc ctgcaggcaa   2100
agcaagcctg gccctgtaat ttgggaaagg aattgtgggc tggcattgtg ttggaggact   2160
tctagggtag tgggtcagaa atgtggtgag gagtgtgttc ctccattggc taggaaacat   2220
ccctgcgatg ctgaaaggtc ttccaatgag cacttaaccc tgtaccgctg tgtcccgaaa   2280
gtggaatggc tgaaattgct ctcctgggag ggagcaagac tcgagttgaa gtttgtttgt   2340
tgttgttgca ccagaaatga aacctggcac tttccccggg gacccctggc tgcagggtct   2400
ccatttaggg tccaagctag cagaatgtgt tcactaggat cagtttctta gacagcaggt   2460
ccagaagcac ctatacccac gtgtattgta aagcaggtgt tcactagatc ccctcccccc   2520
cacatgcacc ttgtaggcat tgtgtgctgc tgcttaaatt agccccccctt ctctaatgca   2580
gcgcagattc ctgtgcgatg aaaccctcag tcctttatat ctcttgtaaa tcagacagcc   2640
gtttcgcttt actctgtcct cccttgttct tctgtcatcc tgacaagctg aagacttttc   2700
aaattacctt cttataagca actgcatcaa cgtttctgaa gctgtgcagt gagggctctg   2760
gttacacgtg aactcctgac cgtgattttg aaatgctccc tgtccccacg tgcactttt    2820
tcccgagatg cttttgtcca cgccaccaag ctcccttata gccttggagt tgtgtatttc   2880
tcttcatatt ttacctagat catgggatgg ggtaggatgg gggaggggac aaagtattat   2940
ctcgtaatct tcaggttcgg gttgtaggga ccgttgagag gggattagtt ccgcatccac   3000
agtaaggatt aaaagtggga ggacttaaga caaggtaatt atttctgcct catctccctg   3060
ccaaaaccat ccatctcctg gcaccatcga gacgagcaat agtaaacaga gcaggagtcg   3120
ccataggtag agtagagact acggccatag ctgcagggcc gctgtaccca taaaacacga   3180
gcagggagat ggtggcagtg taccataaga tgatgctttt ataagctaga gctttactga   3240
agatgtattt tccatttggg cagcaaaagg cattttgctg ccttatagcg gaactcttaa   3300
gccaacactt ctgtatgata tatacataga tatgcattgg aaaagttgtg tttaataaga   3360
tattttgtta taaaacaaag ttttatgaag atatggttgt ttaatattag aagcctattt   3420
ctcccttga cctcctgttt aagtacatca tccatcggtc gccgcgttgt ccgaattagg    3480
caaccaatgc ggatgcaaag gaatctctga tctaattcta cagagcagta attgcctaca   3540
tggatatgtt tatggcattg taactggtat tagtgagatg ctgtaattac tgaccagctt   3600
gctcagcaca attaaatgtc tcagttgcag acagggaaat aaacaaagtc cattaaagaa   3660
ctaaagggga tattgaagaa gacccagctg taggcttgta ggcttgtttc cccgctaaga   3720
attaccctta tccgcatagg gagcagtgct gccacgctgg ctgggaaccg ccagtaaata   3780
atggctttat ttatggtgga actggtggga actggaagat gaacaaagag gatcgcttgt   3840
tgcttgtgat gtggacacgc gccgtgtatc accggggatt tggcatcaac acccaaactg   3900
gctcctcggt atgaatgtgt gccttgccat gtcattgagg aaggttgttc ctggacgatg   3960
ttcccaggct gttcaggcag cagcagagcg tgcattaggt ggaaaccaaa agcatcggtt   4020
```

```
ggcttcccaa ggagaaagag ccacgtccaa aagccaggaa tgactgacac gtttatgtga    4080
tggactttga aaagtaggat ggagtggcac gcaaacaacg cgccaggatg tcccgaactg    4140
gattgctttc ctgttgtaat acctgctggg aagggatttt gtgtttgggc aatgttactg    4200
cttaccaggt gtattgggga gagagtgagg gctctgaaca agggggggtcc tggggctggc    4260 attgggcagt gagagtgtcc tgagctggca ggagggtcca tgtcagtcca ttcaatgcca    4320
caaggtgctg cgtcctggct tgatgacat gcatctgctt tagtgacaga tcccagttct    4380
gccccattcc ttcgagaaaa caaaatacag gcttgcgagc ttctctagct cttgtgttct    4440
tttctcagag tgctactttt gtcaagaact gttttgttgt tcatgcataa aaatctgctg    4500
tgggcagtct gcacagtgga agaagcacct ggttcgtatg gaattgggta acagctatat    4560
accaaagttt tgcacggctc cgcgtgttga gacgagatgc tgcgccgttg tttttttttgg    4620 agacgtcctc attgaatatc catgctttga ccagatgtta caagcctact gctgagccgg    4680
cgatgctatg aatatgcatg gcatggtggc tgtcccccct cactgcgatg tgccactgtg    4740
gttggagggg ctcccacgca tcctgctggc caatggcacc atgtgtgtccc ccagggcttg    4800 gggtggctca gggtccatgc gctcagtcct gtgcggtgct cttgggatcg gctcttggtt    4860
ggccatcgcc tgctgcgctc tgcgatcgct ctgtctccgc cgcttgactt tcctgcttgg    4920
aaatgagatt ctgtaggtgc tgttggtgtg cagattggaa aatgcaaacg atgtgctgaa    4980
agcagcccgg aggctaaaat atgtattcct ggcagctgtg ccaccctcgg tgctcgtgga    5040
gcctttgtag gcagcgggca gacgccgttc ccagcgcggc gctggggcgg ccgcagccat    5100
ctcaggcctc cgccgctgtg attgctgttc tgcacttact ggaaacttca aacatgattt    5160
aaacatgaag gtctattctc gcaccctatt aattatgcat ccgtatgtaa ttctaaagaa    5220
aaagggaaaa ctgtaagtct atatctgttt ttatgctggt ttctctcatg gggattatac    5280
ttcgcgtgcc gacaatttgc ctttggtttg ctcgcagact tagaggtgga attcaggcca    5340
cttaggtcat tggtttggat caattcaata aacctgttta agttttttgca caaaa         5395
```

<210> SEQ ID NO 9
<211> LENGTH: 424
<212> TYPE: PRT
<213> ORGANISM: Gallus gallus

<400> SEQUENCE: 9

```
Met Asp Gln Pro Ser Gly Arg Ser Phe Met Gln Val Leu Cys Glu Lys
1               5                   10                  15

Tyr Ser Pro Glu Asn Phe Pro Tyr Arg Arg Gly Pro Gly Met Gly Val
            20                  25                  30

His Val Pro Ala Thr Pro Gln Gly Ser Pro Met Lys Asp Arg Leu Asn
        35                  40                  45

Leu Pro Ser Val Leu Val Leu Asn Ser Cys Gly Ile Thr Cys Ala Gly
    50                  55                  60

Asp Glu Asn Glu Ile Ala Ala Phe Cys Ala His Val Ser Glu Leu Asp
65                  70                  75                  80

Leu Ser Asp Asn Lys Leu Glu Asp Trp His Glu Val Ser Lys Ile Val
                85                  90                  95

Ser Asn Val Pro His Leu Glu Phe Leu Asn Leu Ser Ser Asn Pro Leu
            100                 105                 110

Ser Leu Ser Val Leu Glu Arg Arg Cys Ala Gly Ser Phe Ala Gly Val
        115                 120                 125

Arg Lys Leu Val Leu Asn Asn Ser Lys Ala Ser Trp Glu Thr Val His
```

```
           130             135              140
Thr Ile Leu Gln Glu Leu Pro Asp Leu Glu Glu Phe Leu Cys Leu
145                 150             155                 160

Asn Asp Tyr Glu Thr Val Ser Cys Ser Pro Val Cys Cys Gln Ser Leu
            165             170                 175

Lys Leu Leu His Ile Thr Asp Asn Asn Leu Gln Asp Trp Thr Glu Ile
            180             185                 190

Arg Lys Leu Gly Ile Met Phe Pro Ser Leu Asp Thr Leu Ile Leu Ala
            195             200             205

Asn Asn Asn Leu Thr Thr Ile Glu Glu Ser Glu Asp Ser Leu Ala Arg
            210             215             220

Leu Phe Pro Asn Leu Arg Ser Ile Asn Leu His Lys Ser Gly Leu His
225             230              235                 240

Cys Trp Glu Asp Ile Asp Lys Leu Asn Ser Phe Pro Lys Leu Glu Glu
                245             250                 255

Val Lys Leu Leu Gly Ile Pro Leu Leu Gln Ser Tyr Thr Thr Glu Glu
                260             265             270

Arg Arg Lys Leu Leu Ile Ala Arg Leu Pro Ser Ile Ile Lys Leu Asn
            275             280             285

Gly Ser Ile Val Gly Asp Gly Glu Arg Glu Asp Ser Glu Arg Phe Phe
            290             295             300

Ile Arg Tyr Tyr Met Glu Phe Pro Glu Glu Val Pro Phe Arg Tyr
305             310             315                 320

His Glu Leu Ile Thr Lys Tyr Gly Lys Leu Glu Pro Leu Ala Val Val
                325             330             335

Asp Leu Arg Pro Gln Ser Ser Val Lys Val Glu Val His Phe Gln Asp
            340             345             350

Lys Val Glu Glu Met Ser Ile Arg Leu Asp Gln Thr Val Ala Glu Leu
            355             360             365

Lys Lys His Leu Lys Thr Val Val Gln Leu Ser Thr Ser Asn Met Leu
            370             375             380

Leu Phe Tyr Leu Asp Gln Glu Ala Pro Phe Gly Pro Glu Glu Met Lys
385             390             395                 400

Tyr Ser Ser Arg Ala Leu His Ser Tyr Gly Ile Arg Asp Gly Asp Lys
            405             410             415

Ile Tyr Val Glu Pro Arg Met Lys
            420

<210> SEQ ID NO 10
<211> LENGTH: 33
<212> TYPE: DNA
<213> ORGANISM: Artificial sequence
<220> FEATURE:
<223> OTHER INFORMATION: Synthetic sequence: Forward primer

<400> SEQUENCE: 10
gctggatcca tgaaagaccg tctcaacctt cca                           33

<210> SEQ ID NO 11
<211> LENGTH: 27
<212> TYPE: DNA
<213> ORGANISM: Artificial sequence
<220> FEATURE:
<223> OTHER INFORMATION: Synthetic sequence: Reverse primer

<400> SEQUENCE: 11
acagaattcg acttcatcct gggctcc                                  27
```

<210> SEQ ID NO 12
<211> LENGTH: 423
<212> TYPE: PRT
<213> ORGANISM: Artificial sequence
<220> FEATURE:
<223> OTHER INFORMATION: Chicken full cell density signal protein with added methionine start sequence, and myc and his tags added on C-terminus

<400> SEQUENCE: 12

Met Lys Asp Arg Leu Asn Leu Pro Ser Val Leu Val Leu Asn Ser Cys
1               5                   10                  15

Gly Ile Thr Cys Ala Gly Asp Glu Asn Glu Ile Ala Ala Phe Cys Ala
            20                  25                  30

His Val Ser Glu Leu Asp Leu Ser Asp Asn Lys Leu Glu Asp Trp His
        35                  40                  45

Glu Val Ser Lys Ile Val Ser Asn Val Pro His Leu Glu Phe Leu Asn
    50                  55                  60

Leu Ser Ser Asn Pro Leu Ser Leu Ser Val Leu Glu Arg Arg Cys Ala
65                  70                  75                  80

Gly Ser Phe Ala Gly Val Arg Lys Leu Val Leu Asn Asn Ser Lys Ala
                85                  90                  95

Ser Trp Glu Thr Val His Thr Ile Leu Gln Glu Leu Pro Asp Leu Glu
            100                 105                 110

Glu Leu Phe Leu Cys Leu Asn Asp Tyr Glu Thr Val Ser Cys Ser Pro
        115                 120                 125

Val Cys Cys Gln Ser Leu Lys Leu Leu His Ile Thr Asp Asn Asn Leu
130                 135                 140

Gln Asp Trp Thr Glu Ile Arg Lys Leu Gly Ile Met Phe Pro Ser Leu
145                 150                 155                 160

Asp Thr Leu Ile Leu Ala Asn Asn Leu Thr Thr Ile Glu Glu Ser
                165                 170                 175

Glu Asp Ser Leu Ala Arg Leu Phe Pro Asn Leu Arg Ser Ile Asn Leu
            180                 185                 190

His Lys Ser Gly Leu His Cys Trp Glu Asp Ile Asp Lys Leu Asn Ser
        195                 200                 205

Phe Pro Lys Leu Glu Glu Val Lys Leu Leu Gly Ile Pro Leu Leu Gln
    210                 215                 220

Ser Tyr Thr Thr Glu Glu Arg Arg Lys Leu Leu Ile Ala Arg Leu Pro
225                 230                 235                 240

Ser Ile Ile Lys Leu Asn Gly Ser Ile Val Gly Asp Gly Glu Arg Glu
                245                 250                 255

Asp Ser Glu Arg Phe Phe Ile Arg Tyr Tyr Met Glu Phe Pro Glu Glu
            260                 265                 270

Glu Val Pro Phe Arg Tyr His Glu Leu Ile Thr Lys Tyr Gly Lys Leu
        275                 280                 285

Glu Pro Leu Ala Val Val Asp Leu Arg Pro Gln Ser Ser Val Lys Val
    290                 295                 300

Glu Val His Phe Gln Asp Lys Val Glu Met Ser Ile Arg Leu Asp
305                 310                 315                 320

Gln Thr Val Ala Glu Leu Lys Lys His Leu Lys Thr Val Gln Leu
                325                 330                 335

Ser Thr Ser Asn Met Leu Leu Phe Tyr Leu Asp Gln Glu Ala Pro Phe
            340                 345                 350

-continued

```
Gly Pro Glu Glu Met Lys Tyr Ser Ser Arg Ala Leu His Ser Tyr Gly
            355                 360                 365
Ile Arg Asp Gly Asp Lys Ile Tyr Val Glu Pro Arg Met Lys Ser Asn
        370                 375                 380
Ser Ala Asp Ile Gln His Ser Gly Gly Arg Ser Ser Leu Gly Pro
385                 390                 395                 400
Arg Phe Glu Gln Lys Leu Ile Ser Glu Glu Asp Leu Asn Met His Thr
                405                 410                 415
Gly His His His His His His
            420
```

<210> SEQ ID NO 13
<211> LENGTH: 129
<212> TYPE: PRT
<213> ORGANISM: Artificial sequence
<220> FEATURE:
<223> OTHER INFORMATION: Chicken 94 aa cell density signal with an added
      methionine start sequence, and myc and his tags added on
      C-terminus

<400> SEQUENCE: 13

```
Met Glu Pro Leu Ala Val Val Asp Leu Arg Pro Gln Ser Ser Val Lys
1               5                   10                  15
Val Glu Val His Phe Gln Asp Lys Val Glu Glu Met Ser Ile Arg Leu
            20                  25                  30
Asp Gln Thr Val Ala Glu Leu Lys Lys His Leu Lys Thr Val Val Gln
        35                  40                  45
Leu Ser Thr Ser Asn Met Leu Leu Phe Tyr Leu Asp Gln Glu Ala Pro
    50                  55                  60
Phe Gly Pro Glu Glu Met Lys Tyr Ser Ser Arg Ala Leu His Ser Tyr
65                  70                  75                  80
Gly Ile Arg Asp Gly Asp Lys Ile Tyr Val Glu Pro Arg Met Lys Asp
                85                  90                  95
Asp Asp Asp Lys Lys Gly Glu Phe Glu Ala Tyr Val Glu Gln Lys Leu
            100                 105                 110
Ile Ser Glu Glu Asp Leu Asn Ser Ala Val Asp His His His His His
        115                 120                 125
His
```

<210> SEQ ID NO 14
<211> LENGTH: 1137
<212> TYPE: DNA
<213> ORGANISM: Gallus gallus

<400> SEQUENCE: 14

```
cgtctcaacc ttccaagcgt gctggtgctg aacagctgtg cataacctg tgcaggggat      60
gagaacgaga ttgctgcctt ctgtgctcac gtctccgaac tcgatctttc tgacaataaa    120
ctggaagact ggcacgaggt cagtaaaatt gtgtccaacg ttccccactt ggagtttcta    180
aacttgagtt ccaatcctct cagtttgtcc gttctagaga aaggtgtgc tgggtccttc     240
gctggtgtcc gcaaacttgt gctcaacaac agcaaagctt cctgggaaac agtccacaca    300
atcctgcagg agttacctga cttggaggag ctcttcctgt gccttaatga ctacgaaaca    360
gtgtcttgtt ctccagtttg ctgtcagtct ctcaaattac tccacataac tgacaataac    420
cttcaagact ggactgaaat tcgaaaattg gcattatgt ttccatctct ggacacccctt    480
attctggcta acaacaacct caccaccatc gaagagtcgg aagattccct cgcaaggctg    540
```

```
ttccccaacc tgcgatccat caatttgcac aagtcaggtc tgcattgctg ggaagacatt      600
gacaagttaa attctttcc caagcttgag gaagtgaaat tgctaggaat ccctttgctg       660
cagtcctaca ccactgagga gcgcaggaag ctgctaatag ccaggttgcc atctatcatc      720
aagctcaacg ggagcattgt tggtgatggg gagcgagagg actcggagcg attcttcatc      780
cgatattaca tggagttccc agaggaggaa gtcccattca ggtaccacga gctgatcacc      840
aagtatggga agctggagcc cttggcagtc gtggatcttc ggccgcagag cagtgtgaag      900
gtggaggttc acttccagga caaagtagaa gagatgtcaa tccgtcttga tcagactgtg      960
gcagaactga agaagcactt aaaaactgtg gtgcagctgt caaccagcaa catgctgctc     1020
ttctacttgg accaggaagc ccccttcggc cccgaggaga tgaagtacag ctcacgagca     1080
ctgcattcct atggcattcg ggatggagac aaaatctatg tggagcccag gatgaag       1137
```

<210> SEQ ID NO 15
<211> LENGTH: 30
<212> TYPE: DNA
<213> ORGANISM: Artificial sequence
<220> FEATURE:
<223> OTHER INFORMATION: Synthetic sequence: forward primer

<400> SEQUENCE: 15
gtgaccatgg agcccttggc agtcgtggat                                        30

<210> SEQ ID NO 16
<211> LENGTH: 30
<212> TYPE: DNA
<213> ORGANISM: Artificial sequence
<220> FEATURE:
<223> OTHER INFORMATION: Synthetici sequence: Reverse primer

<400> SEQUENCE: 16
cttatcgtca tcgtccttca tcctgggctc                                        30

<210> SEQ ID NO 17
<211> LENGTH: 379
<212> TYPE: PRT
<213> ORGANISM: Gallus gallus

<400> SEQUENCE: 17

Arg Leu Asn Leu Pro Ser Val Leu Val Leu Asn Ser Cys Gly Ile Thr
1               5                   10                  15

Cys Ala Gly Asp Glu Asn Glu Ile Ala Ala Phe Cys Ala His Val Ser
            20                  25                  30

Glu Leu Asp Leu Ser Asp Asn Lys Leu Glu Asp Trp His Glu Val Ser
        35                  40                  45

Lys Ile Val Ser Asn Val Pro His Leu Glu Phe Leu Asn Leu Ser Ser
    50                  55                  60

Asn Pro Leu Ser Leu Ser Val Leu Glu Arg Arg Cys Ala Gly Ser Phe
65                  70                  75                  80

Ala Gly Val Arg Lys Leu Val Leu Asn Asn Ser Lys Ala Ser Trp Glu
                85                  90                  95

Thr Val His Thr Ile Leu Gln Glu Leu Pro Asp Leu Glu Glu Leu Phe
            100                 105                 110

Leu Cys Leu Asn Asp Tyr Glu Thr Val Ser Cys Ser Pro Val Cys Cys
        115                 120                 125

Gln Ser Leu Lys Leu Leu His Ile Thr Asp Asn Asn Leu Gln Asp Trp
    130                 135                 140

```
Thr Glu Ile Arg Lys Leu Gly Ile Met Phe Pro Ser Leu Asp Thr Leu
145                 150                 155                 160

Ile Leu Ala Asn Asn Asn Leu Thr Thr Ile Glu Glu Ser Glu Asp Ser
                165                 170                 175

Leu Ala Arg Leu Phe Pro Asn Leu Arg Ser Ile Asn Leu His Lys Ser
            180                 185                 190

Gly Leu His Cys Trp Glu Asp Ile Asp Lys Leu Asn Ser Phe Pro Lys
        195                 200                 205

Leu Glu Glu Val Lys Leu Leu Gly Ile Pro Leu Leu Gln Ser Tyr Thr
    210                 215                 220

Thr Glu Glu Arg Arg Lys Leu Leu Ile Ala Arg Leu Pro Ser Ile Ile
225                 230                 235                 240

Lys Leu Asn Gly Ser Ile Val Gly Asp Gly Glu Arg Glu Asp Ser Glu
                245                 250                 255

Arg Phe Phe Ile Arg Tyr Tyr Met Glu Phe Pro Glu Glu Glu Val Pro
                260                 265                 270

Phe Arg Tyr His Glu Leu Ile Thr Lys Tyr Gly Lys Leu Glu Pro Leu
            275                 280                 285

Ala Val Val Asp Leu Arg Pro Gln Ser Ser Val Lys Val Glu Val His
    290                 295                 300

Phe Gln Asp Lys Val Glu Glu Met Ser Ile Arg Leu Asp Gln Thr Val
305                 310                 315                 320

Ala Glu Leu Lys Lys His Leu Lys Thr Val Val Gln Leu Ser Thr Ser
                325                 330                 335

Asn Met Leu Leu Phe Tyr Leu Asp Gln Glu Ala Pro Phe Gly Pro Glu
            340                 345                 350

Glu Met Lys Tyr Ser Ser Arg Ala Leu His Ser Tyr Gly Ile Arg Asp
            355                 360                 365

Gly Asp Lys Ile Tyr Val Glu Pro Arg Met Lys
            370                 375
```

LIPID CO-FACTOR ESSENTIAL FOR CELL DENSITY SIGNALING

CROSS-REFERENCE TO RELATED APPLICATIONS

This non-provisional application is a Continuation of and claims priority to International Patent Application No. PCT/US14/062729, filed on Oct. 28, 2014, which claims priority to U.S. Provisional Patent Application No. 61/896,604 filed on Oct. 28, 2013, both of which are hereby incorporated by reference in their entirety. This application is related to U.S. Pat. Nos. 5,741,895; 6,245,899; and 6,433,136; all of which are hereby incorporated by reference in their entirety.

STATEMENT OF GOVERNMENTAL SUPPORT

This invention was made with government support under Contract No. DE-AC02-05CH11231 awarded by the U.S. Department of Energy, and Grant No. CA064786 awarded by the National Institutes of Health. The government has certain rights in the invention.

REFERENCE TO SEQUENCE LISTING, TABLE, OR COMPUTER PROGRAM APPENDIX

A sequence listing is submitted concurrently with the specification and is part of the specification and is hereby incorporated in its entirety by reference herein. This application also incorporates by reference the sequence listing found in computer-readable form in a *.txt file entitled, "[3190US_SequenceListing_ST25.txt]", created on [Apr. 19, 2016], which is identical to the sequence listing in paper form provided at the time of filing.

BACKGROUND OF THE INVENTION

Field of the Invention

The present invention relates to compositions and methods for modulating cell density signaling.

Related Art

To function correctly, a cell needs a real-time assessment of its environment. A key component of this running tally is cell density—a parameter known to alter both the rates of cell proliferation and the level of cell differentiation. Loss of cell density awareness has long been associated with the onset of cancer and the ability of malignant cells to overgrow the monolayer when grown in cell culture[1]. Similarly, in normal cells the slowdown in growth as cells become dense is associated with the induction of differentiated function[2]. Despite its importance to normal function, how a cell "sees" its neighbors remains an enigma. The sensing mechanism is known to be influenced by high concentrations of growth factors, for instance high serum levels, but this has not shed light on how a cell actually detects the presence of its neighbors[3,4]. Therefore, to better comprehend tissue morphogenesis and stability requires an understanding of how cells signal their presence to each other.

Tendon morphogenesis is highly dependent on cell density signaling. This is because the tissue is over 90% type I collagen and the two parameters controlling local collagen deposition—the rate of cellular collagen production and the cell number—are cell density regulated[5,6]. Cell density regulation of cell proliferation and apoptosis causes a growth plate to form, allowing the cells to deposit an even distribution of collagen along the longitudinal axis of the fibril—a hallmark of this tissue[7].

In cell culture primary avian tendon (PAT) cells from 16 day embryos devote ~50% of their total protein production to procollagen[8]. This high level is identical to that seen in ovo where tendon development occurs rapidly (~11 days) enabling the newly hatched chick the ability to walk. To produce high levels of procollagen from a single copy gene and allow rapid regulation puts restrictions on where this pathway can be controlled. Transcription is an unlikely candidate because induction is slow from a single copy gene. When PAT cells are stimulated to make high levels of collagen, there is a 12 h lag before the cells linearly increase the procollagen mRNA levels over a 2.5 day period[5]. Moreover, to maintain the pool of procollagen mRNA, it has to be stable with a half-life of 24 h[9]. So manipulating procollagen mRNA levels is not feasible when the cells are required to make high levels of procollagen. Instead the cell regulates procollagen at a post-translational step. Translation and secretion rates are both tied to formation of a triple helical molecule and this in turn requires hydroxylation of prolines to stabilize this conformation. This can be manipulated by the addition of ascorbate whose only known role in the process is being a reducing agent and this rapidly (<30 min) induces a 6 fold increase in procollagen secretion[10] and a 2 fold increase in procollagen translation (rates reach 6 fold but require a partial increase in mRNA)[5]. In the fully induced state, inhibiting prolyl hydroxylase by chelating ferrous ion causes a rapid drop in procollagen translation (>50% in 2 h)[5]. The enzyme, prolyl hydroxylase, responsible for this rapid regulatory control requires ascorbate to keep its catalytic ferrous ion in a reduced state. The enzyme has two subunits and the level of the alpha subunit is dependent on cell density[11]. How cell density regulates prolyl hydroxylase has not been defined except that the pool of this enzyme increases 5-6 fold while the level of its mRNA remains unchanged[11]. With 5 cysteines the alpha subunit of prolyl hydroxylase would be sensitive to the redox potential of the cell and this has been postulated as a mechanism for signal transduction[11].

Cell density signaling plays a critical role in the formation of high collagen producing tissues such as tendon, ligament, and bone. Knowing its neighbors allows the cell to control its collagen production and proliferation. The net effect in tendon is the formation of a growth plate where cells at the leading edge at moderate density are growing, cells in the middle at high cell density stop growing and make high levels of collagen, and cells at the trailing edge are apoptosing. In the adult tendon the few remaining cells that were on the periphery of the growth plate and never reached high cell density are now at low cell density in a maintenance state. It is not known whether a damaged tendon can be driven to form a new growth plate by injecting a tendon cell density signal and thereby heal a damaged tendon with speed and strength. Identification of and understanding these signals as potent and specific agents that drive the morphogenesis of tissues is needed.

BRIEF SUMMARY OF THE INVENTION

Herein we describe, a candidate gene for the diffusible cell density signal is put through the classic test to validate its activity: ectopic expression in another cell type from another species, purification of the recombinant factor, and testing back on PAT cells to see if it acts like the original diffusible cell density signal. This classic approach is complicated by the finding that the cell type producing this protein binds a unique tissue-specific lipid cofactor and this composite molecule imparts a tissue-specific response.

Cell density is a critical parameter controlling tendon morphogenesis. Knowing its neighbors allows a cell to regulate correctly its own proliferation and collagen production. A missing link to understanding this process is the sensing mechanism. Previously, this mechanism was shown to rely on a diffusible factor with an affinity for the cell layer. Purifying and sequencing the band that best correlated with a cell proliferation assay yielded an 8 amino acid (AA) sequence that was part of a 424 AA gene product, highly conserved between chicken and human (89% identical). By cleavage the 8 AA sequence, towards the carboxy terminus, could begin a 94 AA secreted protein. To validate its role, the chicken cDNA was transfected into a human osteosarcoma cell line (U2OS) to test whether the recombinant protein would exhibit the expected activity on tendon cells. U2OS cells expressed the gene but not passively: differentiating into structures resembling spongy bone and expressing alkaline phosphatase, an early bone marker. Intracellularly, two bands were observed: the full length protein (44 kD) and a smaller form (26 kD). Outside the cell, a 28 kD band was detected as well as multiple larger bands. In various embodiments, these larger forms could be converted to a 16 kD form by changing salt concentrations and ultrafiltering— releasing a cofactor to the filtrate while leaving a protein factor in the retentate. Using various enzymes the cofactor was identified as a lipid. Through mass spectrometry, the cofactor was shown to be a 1114.89 MW molecule containing a ceramide phosphate, a single chained glycerol lipid and a linker. Chick tendon uses a different cofactor made up of two fatty acid chains linked directly to the phosphate yielding a molecule about half the size. Moreover, adding the tendon factor/cofactor to osteosarcoma cells causes the osteosarcoma cells to stop growing which is opposite to its effects on tendon cells. The cofactor is cell type specific both in composition and in the triggered response. Further proof of its role came from frozen sections from 5 week old mice where an antibody to the factor stained strongly at the growing ends of the tendon as predicted. Thus, we describe herein one part of the cell density signaling mechanism is a small protein bound to a unique, tissue-specific phospholipid yielding a membrane associated but diffusible molecule.

To analyze what was secreted from the cell, the CM was put through a 30 kD ultrafilter and the retentate and the filtrate were further concentrated on a 10 kD ultrafilter so that a sufficient level of protein could be loaded onto the gel. The retentate shows a wide spectrum of bands from the smallest at 28 kD, the most intense at ~60 kD and the highest at ~250 kD (lanes 5, 6). The filtrate showed one band at ~60 kD (lanes 7, 8). Since the filtrate initially went through a 30 kD ultrafilter, this large band is an indication that concentrating the sample causes aggregation.

Figure 3:
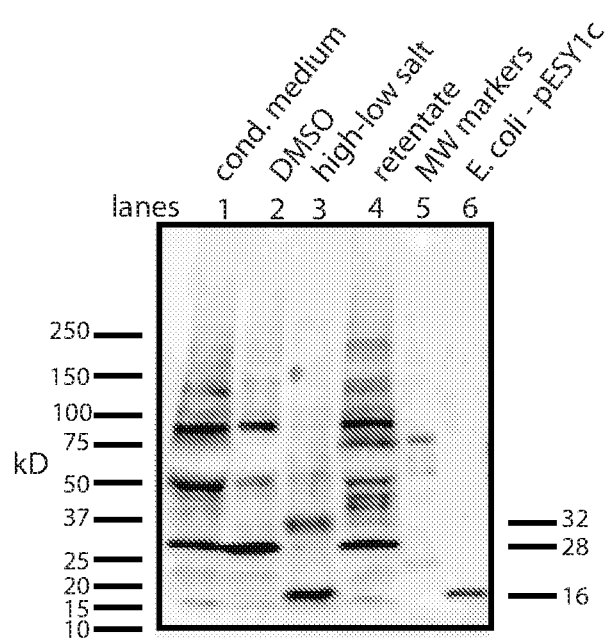

FIG. 3—Determining whether the apparent aggregation of the factor in the CM is due to covalent modifications or binding of a cofactor. When the CM was concentrated using a 10 kD ultrafilter and this sample was analyzed by Western using a myc antibody (clone 4A6), one sees a lane of multiple bands, the smallest being 28 KD (lane 1). In contrast, if the secreted form of the factor with tags (94 AA+tags) is expressed in *E. coli*, one sees a single band at 16 kD (lane 6). Lane 5 was reserved for MW markers. The CM was put through a 30 kD ultrafilter and the retentate used as a control (lane 4) and the filtrate was divided into two parts. The first was further concentrated on 10 kD ultrafilter and then made 30% DMSO in order to see if this solvent could affect the mobility of the factor (lane 2). The DMSO did limit the aggregation in that more of the factor ran at 28 kD. In contrast, when the filtrate was treated with high salt (0.5 M) and then low salt by 10 fold dilution and then concentrated on a 10 kD ultrafilter, the bands almost all went to a 16 kD form and its 32 kD dimmer (lane 3). This is strong evidence that whatever was causing the increased MW to 28 kD and the further aggregation was not covalently bound.

Figure 4A:
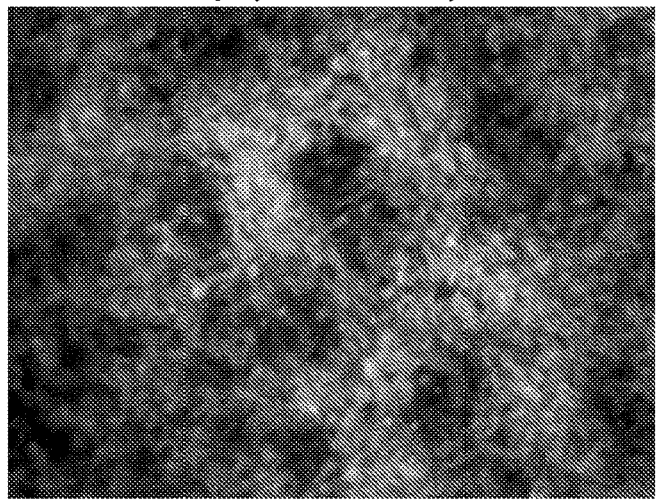
Figure 4B:
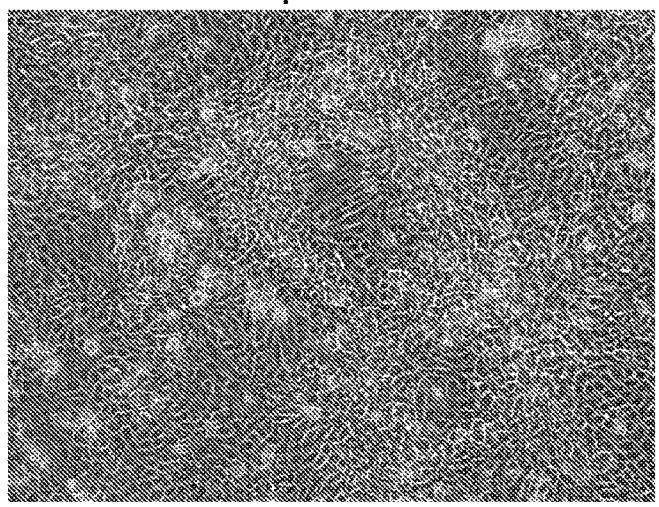
Figure 4C:
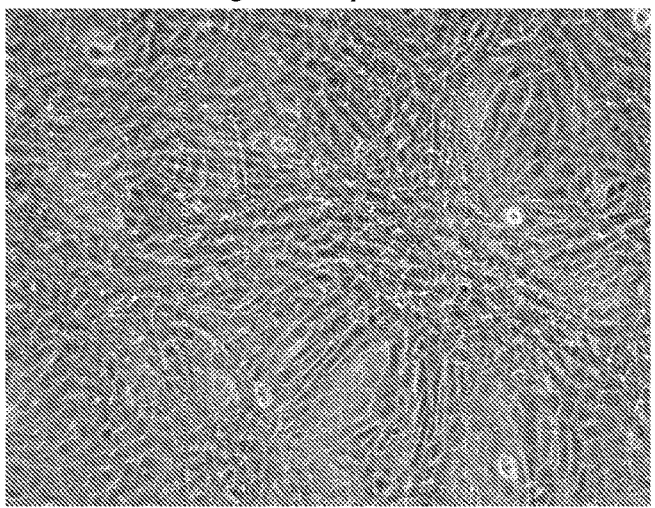

FIGS. 4A, 4B, and 4C—Localization of the bone factor/cofactor in the extracellular space and disruption by gentle agitation. U2OS-pESY1c cells were grown in culture for 9 days and then fixed with 4% paraformaldehyde in a high calcium buffer. A rabbit polyclonal antibody was used as a primary and goat anti-rabbit alexa 488 was used as a secondary (FIG. 4A). For comparison, the same field is shown in phase contrast (FIG. 4B). Areas where the cells are overgrowing the monolayer show strong staining whereas cells remaining in the monolayer appear to be suppressed. This leads to the strong localized differences in the expression of this gene.

When CM was collected from these cells, the flasks are gently rotated (100 rpm) for 1 h; then the medium is collected and new medium is added. After 3 collections the flasks are stationary for the next 21 h. After collecting medium for 3 days a dramatic change is observed in the culture—the cells no longer accurately detect the cells around them and they grow all over the dish as seen in phase contrast (FIG. 4C).

Figure 5A:
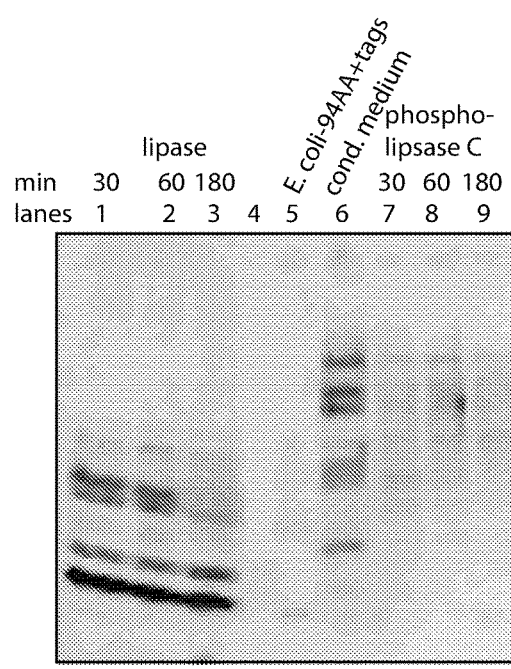
Figure 5B:
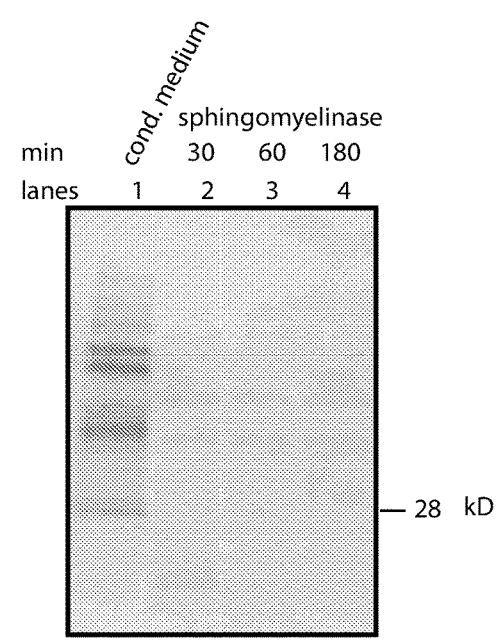

FIGS. 5A and 5B—Treating U2OS-pESY1c CM with various lipid degradative enzymes to identify the makeup of the bone cofactor. The only assay for the cofactor is its binding to the factor and shifting its mobility. The CM was treated with lipase, phospholipase C, and sphingomyelinase for 30, 60, and 180 min and analyzed by Westerns using a myc monoclonal antibody (FIG. 5A, lanes 1, 2, 3; FIG. 5A, lanes 7, 8, 9; and FIG. 5B, lanes 2, 3, 4; respectively). The *E. coli* expressed secreted form of the factor (94 AA+tags) was run as a control (FIG. 5A, lane 5 showing a monomer band at 16 kD and a dimer band at 32 kD) as well as untreated CM (FIG. 5A, lane 6; and FIG. 5B, lane 1). FIG. 5A, lane 4 contained MW markers (data not shown). The lipase was the least specific enzyme and it degrades the cofactor and leaves most of the factor running at 16 kD. This type of phospholipase C can cleave at both glycerol phosphates and ceramide phosphates. The sphingomyelinase is specific for ceramide phosphates. Both of these enzymes cause single breaks and this alters the binding/mobility but does not free the cofactor from the factor.

Figure 6:
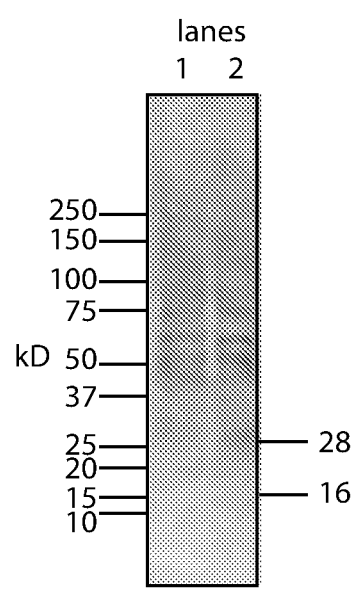

FIG. 6—Chloroform/methanol extraction does not free the lipid bone cofactor from the protein factor. To test whether the standard extraction method of purifying lipids would yield a free cofactor, CM from U2OS-pEsy1c was extracted with chloroform/methanol. The protein fraction which precipitates at the interface between the two solvents was examined by Western blotting using a myc monoclonal antibody (lane 1 is half the sample volume of lane 2). Despite unusual sample preparation, the SDS gels and Western blotting worked reasonably well. Nevertheless, there was no evidence of a 16 kD free protein factor. Instead the bands resembled those of the factor/cofactor running together with a minimum size of 28 kD.

Figure 7:
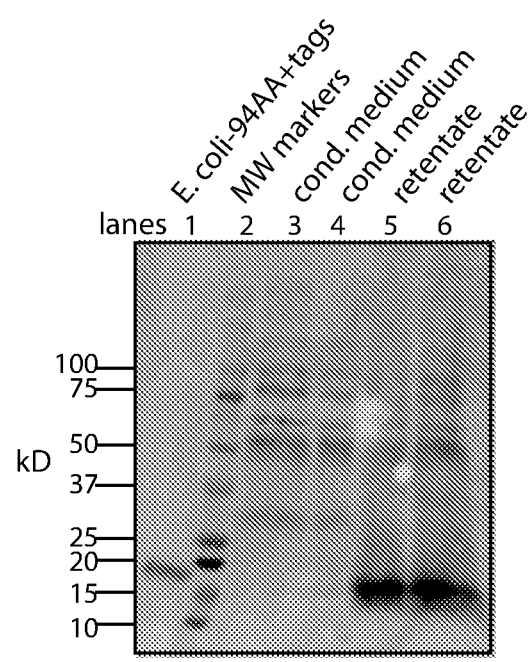

FIG. 7—A simplified procedure using ultrafiltration and high salt releases the bone cofactor. In this composite Western (using a myc monoclonal antibody, clone 4A6) where the molecular weight markers (lane 2) are superimposed on the other lanes. The secreted form of the factor made in $E.$ $coli$ (94 AA+tags) was run in lane 1 and the concentrated CM was run in lanes 3, 4. To release the cofactor the CM was made ~0.6 M NaCl and then concentrated on a 10 kD YM-10 ultrafilter and then diluted with water and refiltered using the same filter (lanes 5, 6). In this case, the retentate shows a strong shift to the secreted form of the factor without cofactor, MW of 16 kD.

FIGS. 8A, 8B, 8C and 8D—Identification of the bone cofactor on mass spectrometry by using lipid degradative enzymes and differential elution from a C-18 spin column. After separation from the factor, the bone cofactor was in the dilute filtrate. To concentrate the lipid containing cofactor, the filtrate was run over a C-18 column and washed with water, acetonitrile, and eluted with chloroform. To identify the cofactor, the cofactor was treated separately with phospholipase C (FIG. 8B) and lipase (FIG. 8C). These were compared to untreated cofactor (FIG. 8A) and a lipase buffer only control (no cofactor; FIG. 8D) using mass spectrometry. The only regions that showed a strong peak in the untreated sample and little or no intensity in the other panels were at an m/z of 543.42 and 557.44. These peaks had the characteristic pattern of a doubly charged molecule and this gave the cofactor a MW of 1086.84 or 1114.88.

Figure 9:
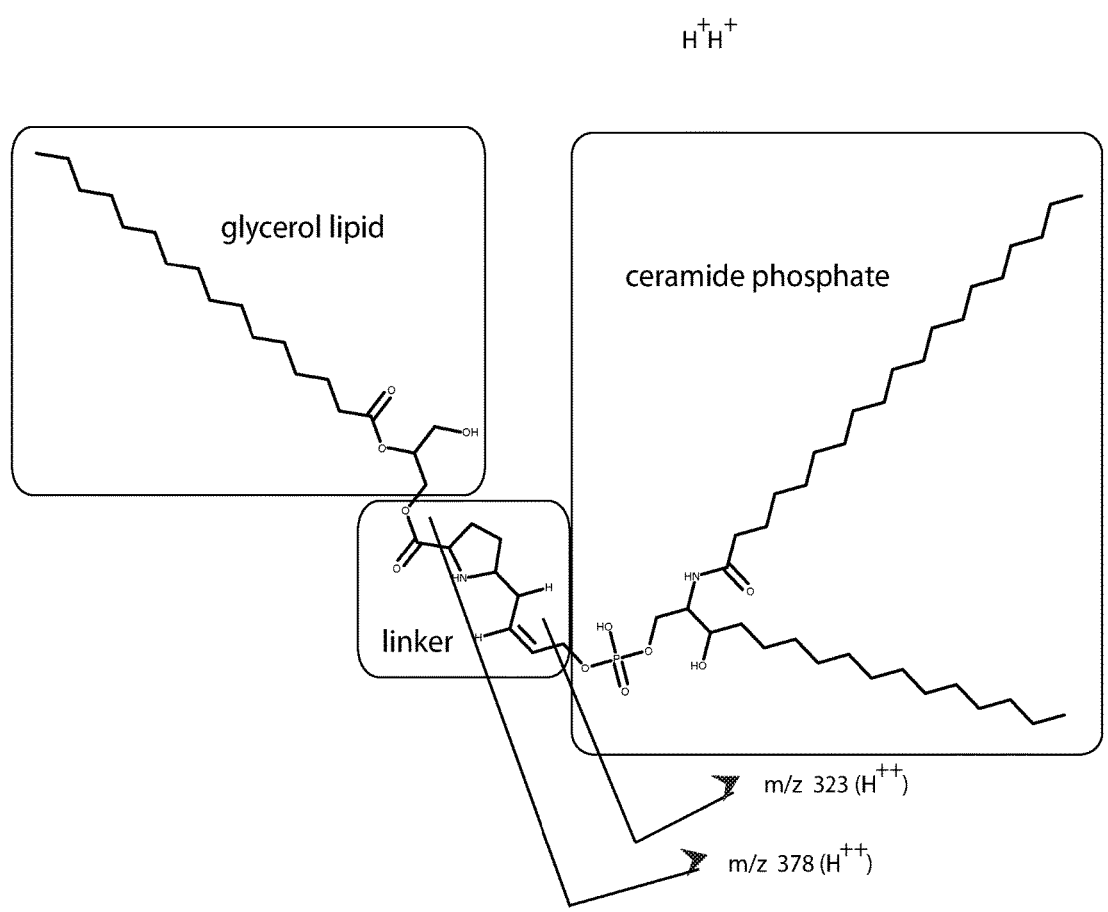

FIG. 9—Working model is shown for the bone cofactor. Using our knowledge of the lipid enzyme preferences, the molecular weight of the whole molecule, the predicted molecular formula, and the fragmentation pattern (MS/MS), a preliminary model has been drawn with a ceramide phosphate, a single chain glycerol lipid, and a small linker. This model also explains why this molecule is soluble from aqueous buffers to chloroform: a structure with a hydrophilic end and hydrophobic tails. The model also shows how the fragmentation pattern of two breaks (MS/MS) is consistent with the model.

Figure 10:
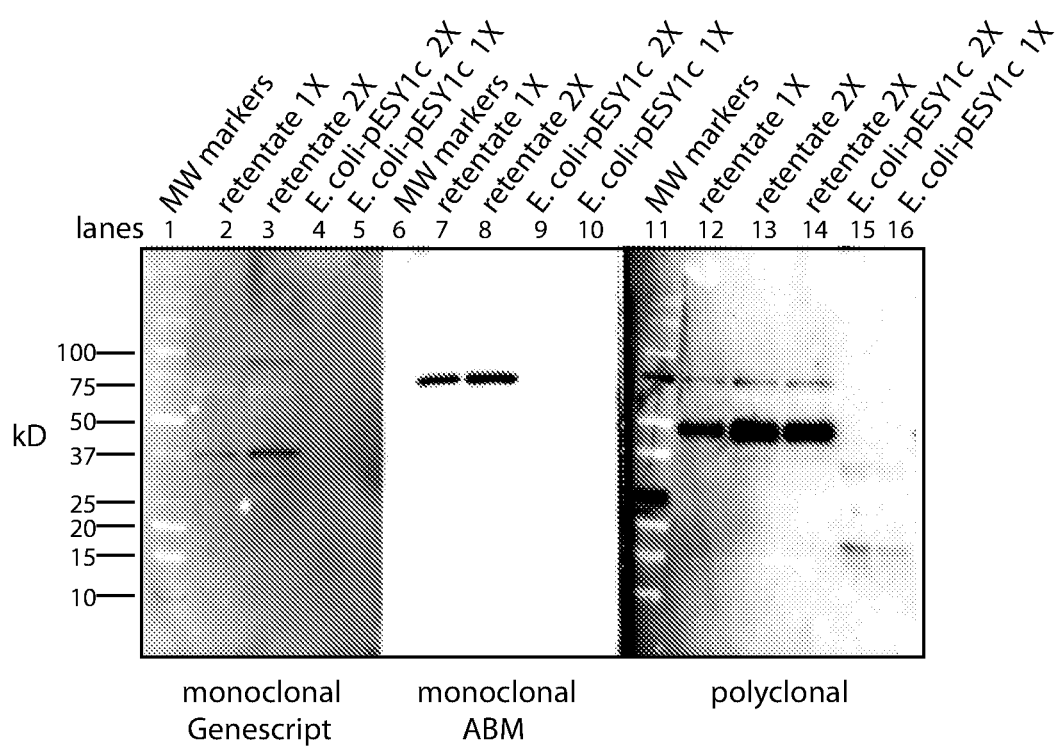

FIG. 10—The conformation of the tagged factor and its interaction with the cofactor dramatically influences the detection by monoclonal and polyclonal antibodies. During the course of these experiments Millipore changed the stabilizing agent for its monoclonal antibody (clone 4A6) and it would now only recognize the free form of the factor. The Millipore monoclonial had been selected because it detects the myc sequence in a "variety of sequence contexts." Two other monoclonal antibodies were tested—Genescript clone 2G8D5 (lanes 1-5) and ABM clone A7 (lanes 6-10)—to see if they could be an adequate replacement. In addition, a polyclonal antibody made in rabbits to the secreted form of the factor (94 AA+tags) expressed in $E.$ $coli.$ was tested (lanes 11-16). For each case, the same samples were used: MW markers (lanes 1, 6, 7) the retentate from trying to separate the factor from the cofactor at 1× (lanes 2, 7, 12) and 2× (lanes 3, 8, 13, 14) and the free factor with tags made in $E.$ $Coli$ at 2× (~1 ng, lanes 4, 9, 15) and 1× (~0.5 ng, lanes 5, 10, 16). The monoclonal antibodies show no overlap in what they detect and neither of them detects the free factor made in $E.$ $Coli$ at the concentration used. The ABM monoclonal is striking in how strong it reacts to only one form at ~75 kD with almost no background. The polyclonal does prefer the ~50 kD form, shows some affinity for the 75 kD form as well as weak affinity for some of the lower MW forms. The polyclonal antibody is sensitive to the secreted factor made in $E.$ $coli$ and can be used in an assay for the separation of the factor from the cofactor. The critical point is that one cannot compare the intensity between bands but only the change in intensity of one band after different treatments.

Figure 11A:
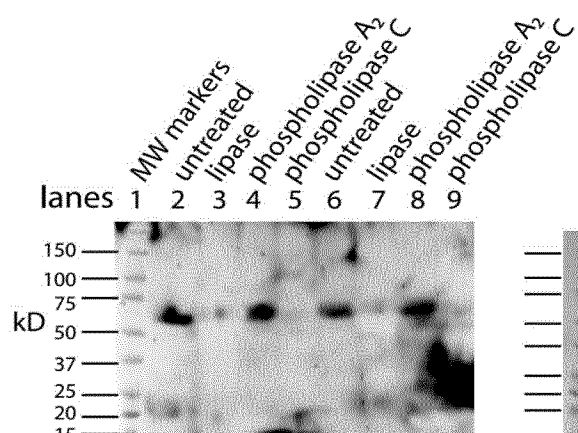
Figure 11B:
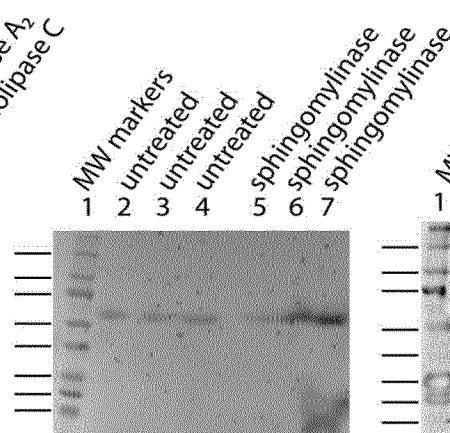
Figure 11C:
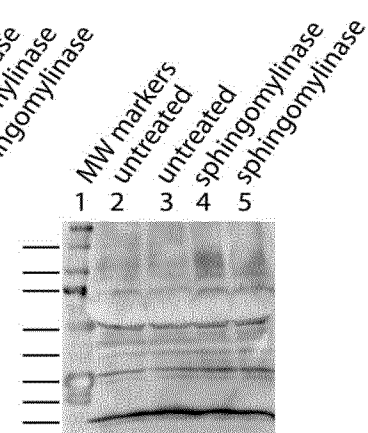
Figure 12:
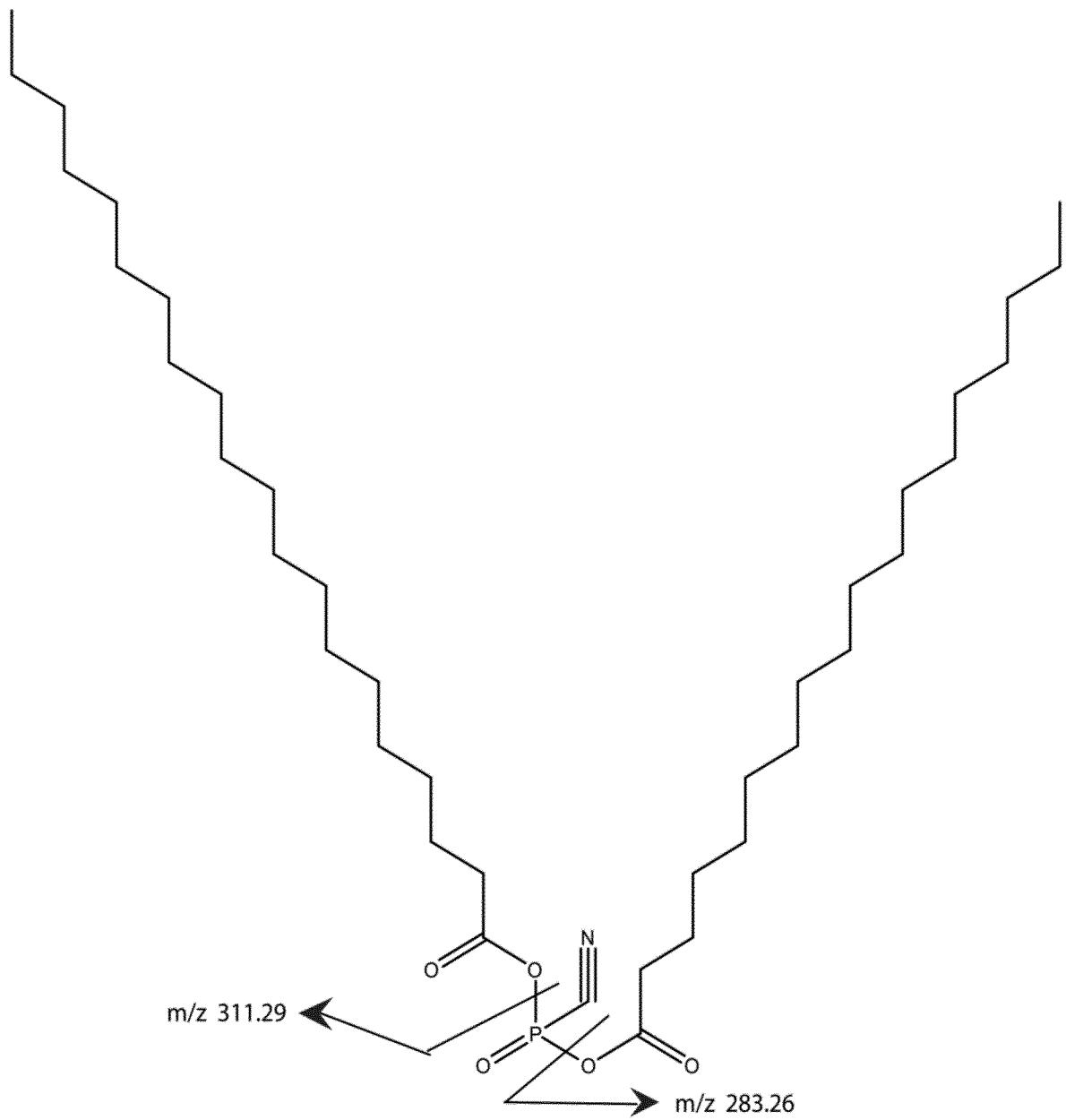
Figure 15:
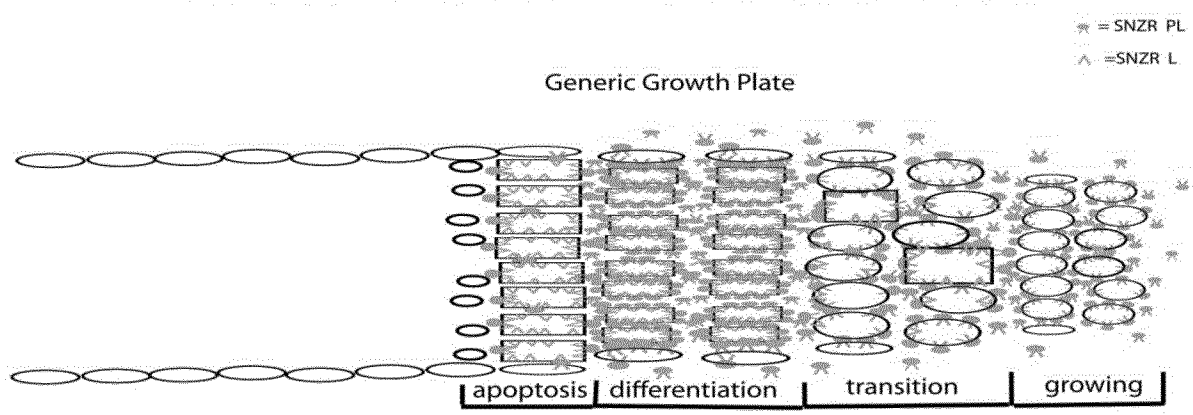
Figure 16A:
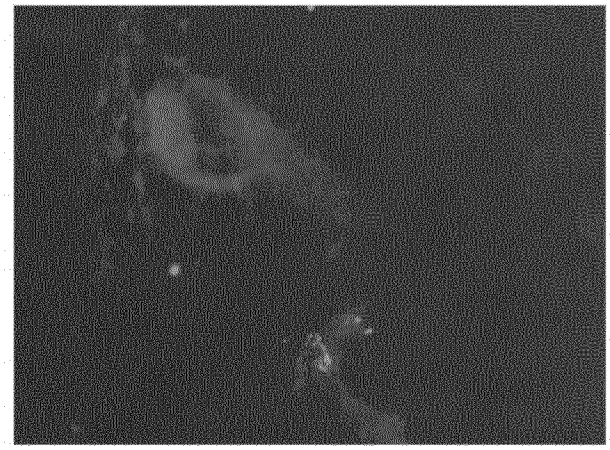
Figure 16B:
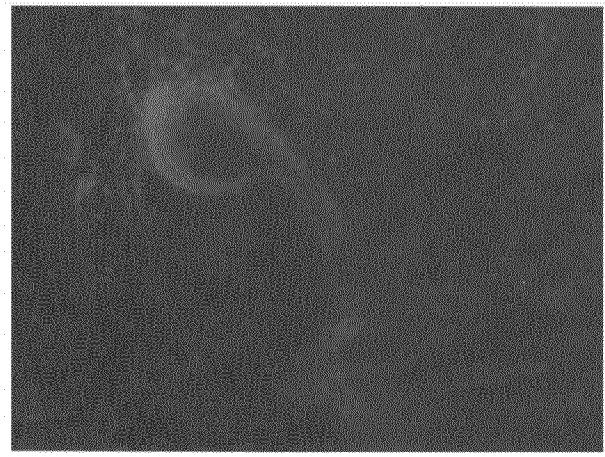

FIGS. 11A, 11B, and 11C—Characterizing the tendon cofactor by its sensitivity to specific lipid degradative enzymes. PAT cell CM was put through a 30 kD filter and then concentrated with a 10 kD filter. This concentrated CM after several months at 4° C. forms a dominant aggregate that runs at ~60 kD. This CM was run on Westerns (using a polyclonal antibody) as follows: untreated (FIG. 11A, lanes 2, 6); lipase treated (FIG. 11A, lanes 3, 7); phospholipase $A_2$ (FIG. 11A, lanes 4, 8); and phospholipase C (FIG. 11A, lanes 5, 9). The data indicates a strong sensitivity to lipase and phospholipase C but not to phospholipase $A_2$. This is identical sensitivity pattern as seen with the bone cofactor. Next sphingomylinase was tested (FIG. 11B, lanes 5, 6, 7) and compared to the untreated control (FIG. 11B, lanes 2, 3, 4). In contrast to the bone cofactor, sphingomyelinase did not affect the tendon cofactor. To rule out that the sphingomyelinase was being inhibited by the aggregation caused by "aging" the CM, fresh cultures of PAT cells were made and the CM treated with sphingomyelinase (FIG. 11C, lanes 4, 5) and untreated control (FIG. 11C, lanes 2, 3). Again, this enzyme does not alter the mobility of the tendon factor/cofactor.

Figure 12:
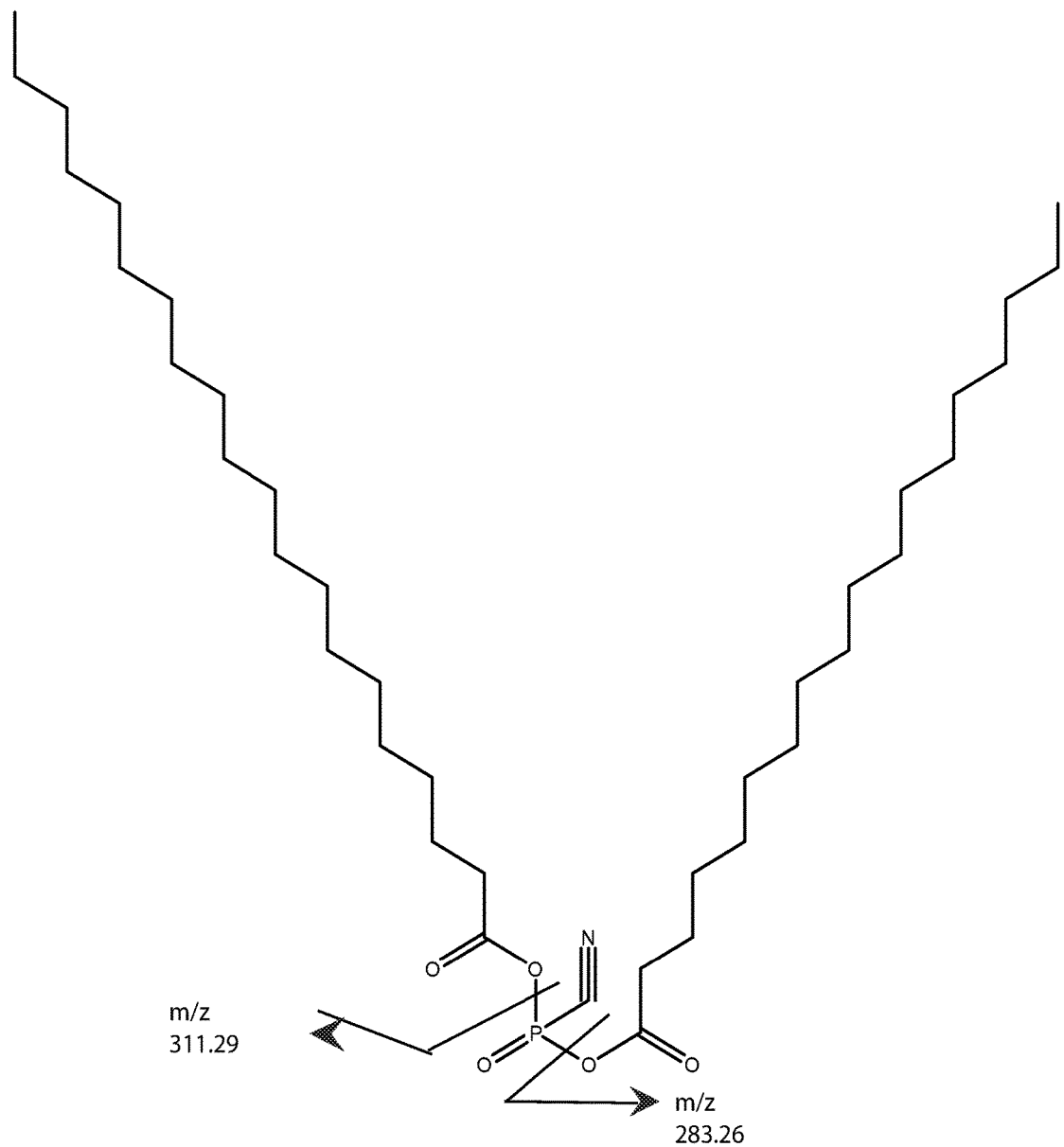

FIG. 12—A working model is shown for the tendon cofactor. The same approach as previously used with the bone cofactor yielded two peaks at 668.61 and 696.65 separated by 28. This difference is commonly seen for lipid chains by addition of two $CH_2$ groups. Since the 668 band was stronger, we focused the model on this band. The ms/ms fragmentation pattern was fairly simple yielding two bands of roughly equal intensity corresponding to an 18 and 20 carbon fatty acids. Since the molecule is degraded by phospholipase C, a phosphate was added to the model. However, there was insufficient MW for a glycerol so the fatty acids were attached directly to the phosphate. The remaining MW fits a cyano group. The working model is presented to give a framework to the type of structure expected.

FIGS. 13A-F—The cofactor has a unique lipid makeup depending on the producing cell type but would SNZR 1P1L and SNZR 1P2L give the same or different response if added to the same cell type. In this case we used the control cell line U2OS and added a 5× concentrated condition medium from PAT cells or from U2OS-pESY1c cells. An additional test was done to see if the free factor made in *E. coli* had any activity on U2OS cells if applied at a high concentration (5 µg/ml).

Figure 13A:
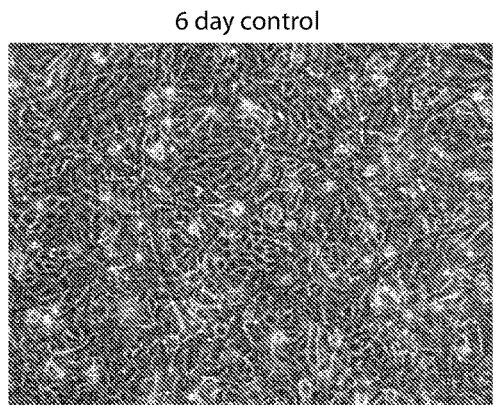

In comparison to expressing pESY1c in U2OS cells which causes hills and valleys to form, adding 5×CM from these cells to uninfected U2OS cells shows only a slight growth effect after 6 days as the cells appeared to be more compact (FIG. 13B) vs medium only control (FIG. 13A). Growing the cells for an additional 9 days showed a strong growth effect (FIG. 13F) vs the medium only control (FIG. 13E). Moreover, the increased growth is even over the culture—no hills or valleys. In contrast, adding 5×CM from PAT cell cultures caused the U2OS cells to grow more slowly and the presence of more rounded up cells (FIG. 13D). Adding high concentrations of the secreted form of the factor alone (expressed in *E. coli*, 94 AA+tags) did not appear to increase growth after 6 days (FIG. 13C).

Figure 14A:
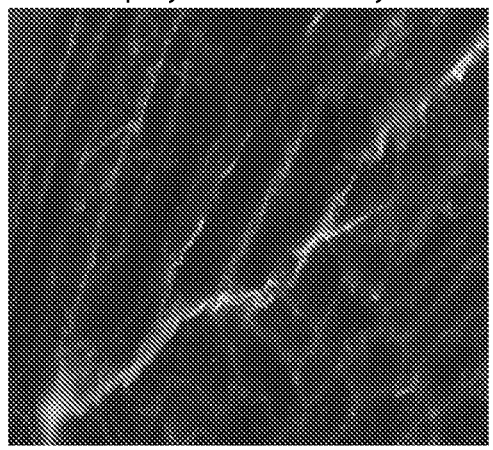
Figure 14B:
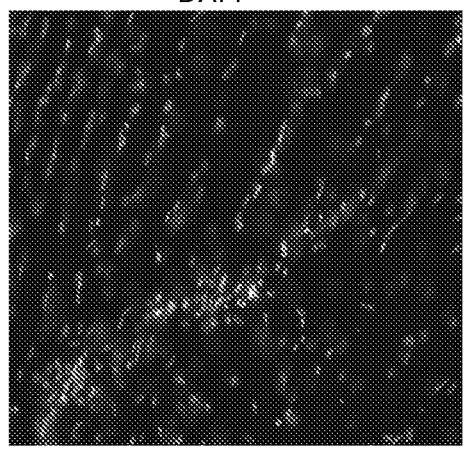
Figure 14C:
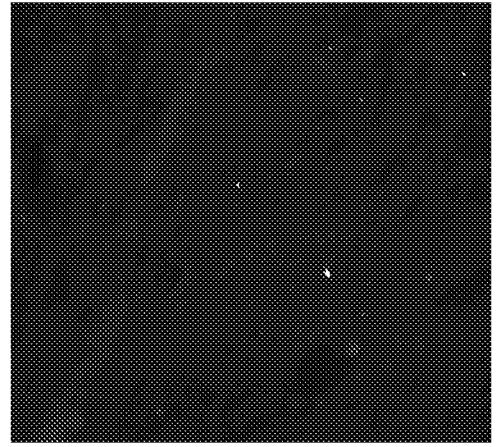
Figure 14D:
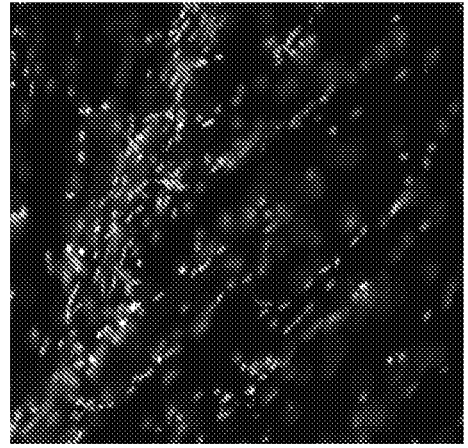

FIGS. 14A-D—Localization of the factor using a rabbit polyclonal antibody in 5 week old mice at the tendon/muscle junction. In the first photograph (FIG. 14A) a small tendon is seen from the lower left edge of the image towards the middle. The polyclonal antibody staining for the factor (using a secondary antibody, goat anti rabbit Alexa 568 (Invitrogen), showed intense staining compared to the muscle bundles. Staining the same section with DAPI shows that this part of the tendon is full of nuclei reflecting that this is a growing end (FIG. 14B). The connective tissue surrounding the muscle shows nuclei staining with DAPI that looks like a line of nuclei. The light staining of the muscle connective tissue with the polyclonal antibody suggests another cell density signal with its own cofactor. As a control, a preimmune serum used at the same concentration, and exposed for the same time was used to detect non-specific signal (FIG. 14C). The same section was DAPI stained and the stained nuclei show a growing tendon rising steeply from the lower left corner to the top of the picture (FIG. 14D). One has to take into account that the tendon does not have to be in exactly the same plane as the tissue slice and therefore, the nuclei density can vary as the tendon weaves through the muscle. Scale bar=100 µm.

Figure 15:
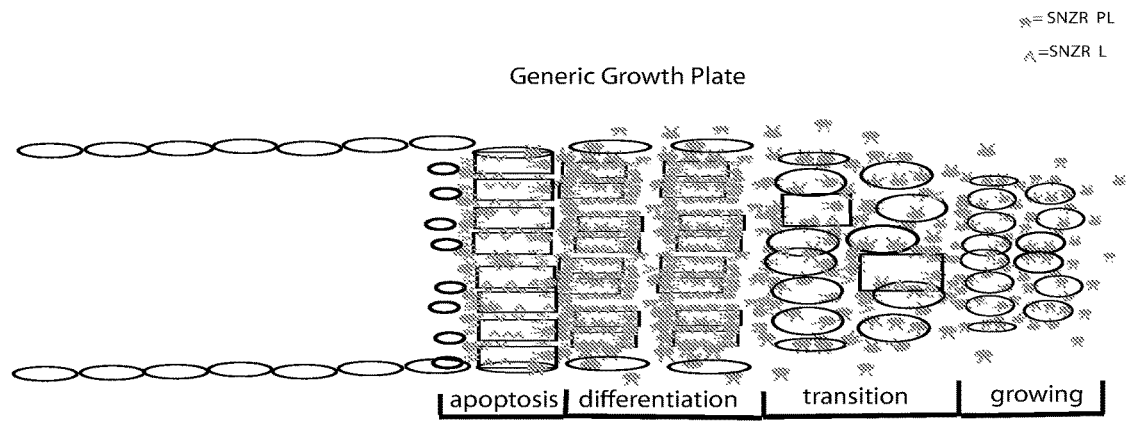

FIG. 15—Schematic representation of tube formation—a critical process in diverse tissues. Glandular tissues clearly need ducts (tubes) to secrete their products. Tendons, a structural tissue, also form tubes but fill them with collagen to make fibrils. This solves the problem of how to make a collagen thread that can be long but maintain a precise diameter for uniform strength. The key element is a growth plate where cells are proliferating and moving forward on one side (right) while they are mostly dying on the opposite side (left). To accomplish this requires two factors: SNZR PL (blue) and SNZR L (dark yellow). Growth is stimulated at moderate cell density by the production by many cells of SNZR PL—the factor is found in the fluid surrounding the cells as well as bound to the plasma membrane. The binding of SNZR PL not only stimulates growth but the production of a non-diffusible second factor that we postulate is SNZR L. This causes another change in the cell membrane and some cells slow growth and become more differentiated which we show as oval cells becoming retangular in the transition zone. As cells become denser, they accumulate more SNZR PL and SNZR L and become highly differentiated. The exception is cells at the outer edge of the tube that due to their position never reach high cell density (narrow ovals). The high level of SNZR L causes a drop in the production of SNZR P and this triggers apoptosis.

In tendon, the differentiated cells produce half of their total protein synthesis as procollagen and they fill the tube with collagen and become a fibril. The cells at the edge are not necessarily contiguous or ordered. One can extrapolate that in a gland, the differentiated zone would produce a variety of mature phenotypes that could escape apoptosis and form a tight single or multi-cell layered duct.

Figure 16A:
Figure 16B:
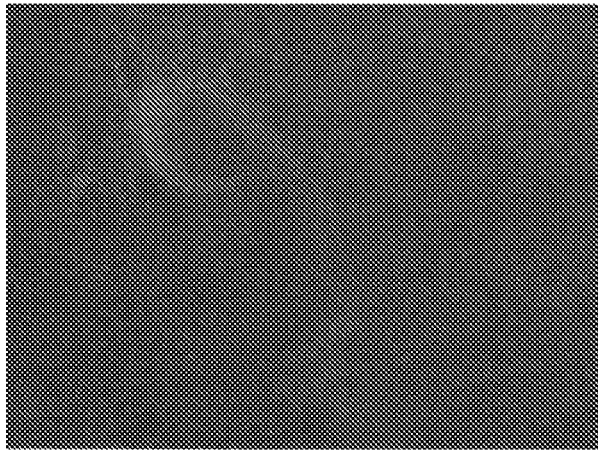
Figure 1A:
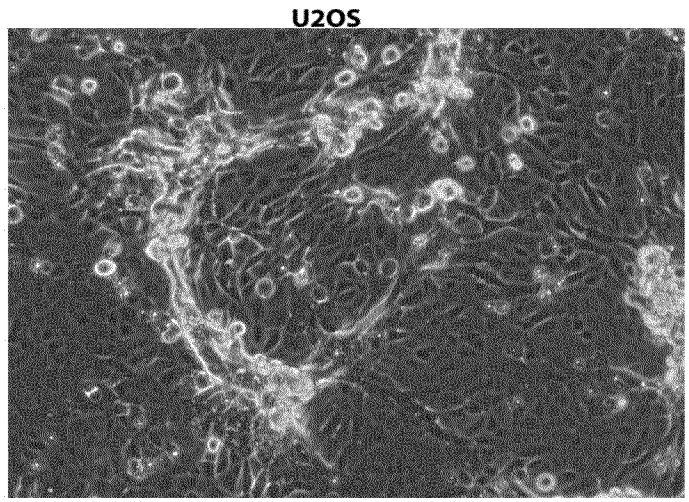
Figure 1B:
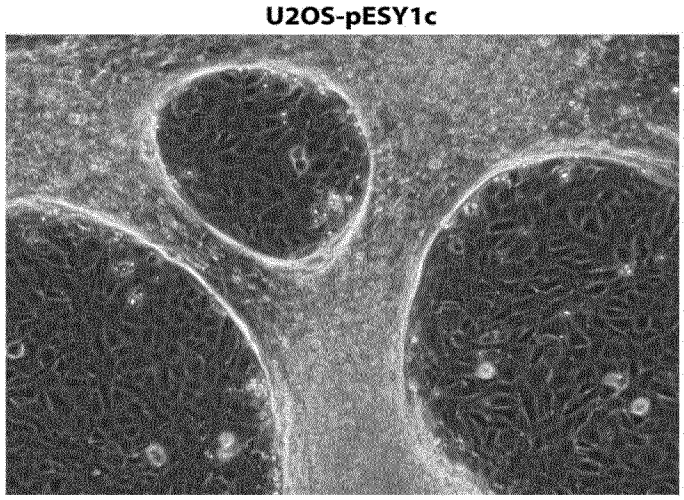
Figure 1C:
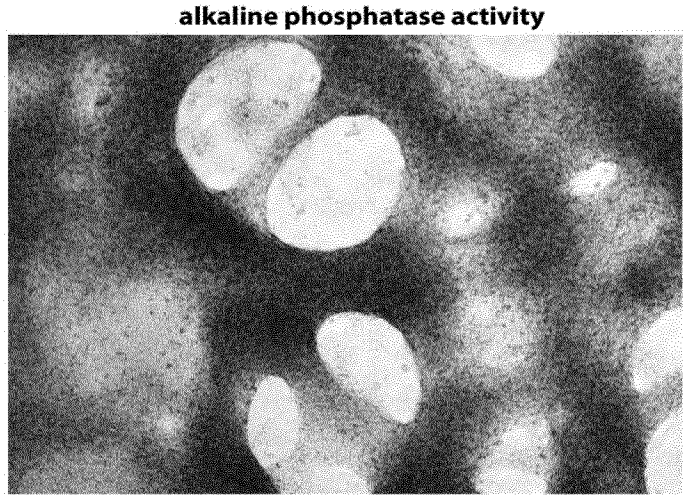
Figure 2:
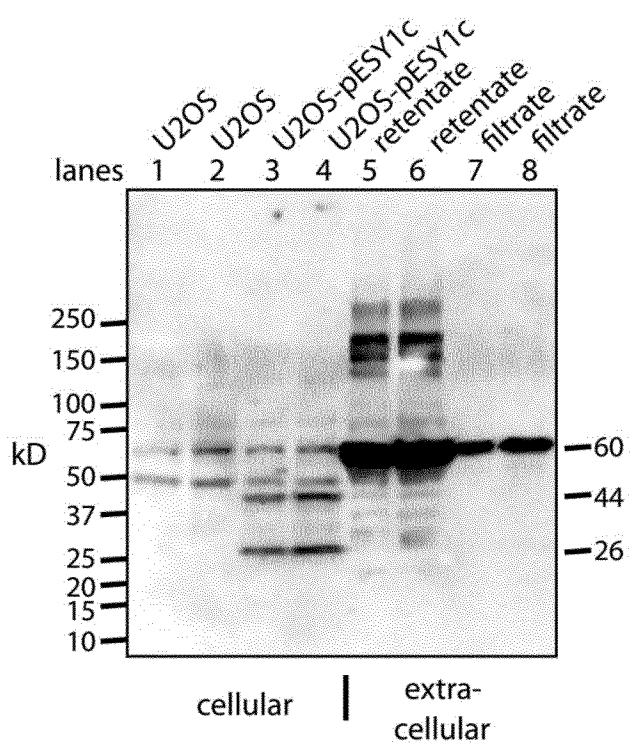
Figure 3:
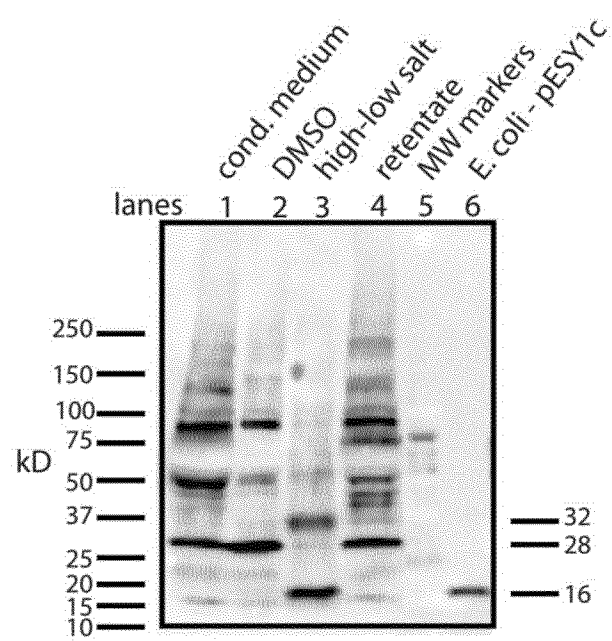
Figure 4A:
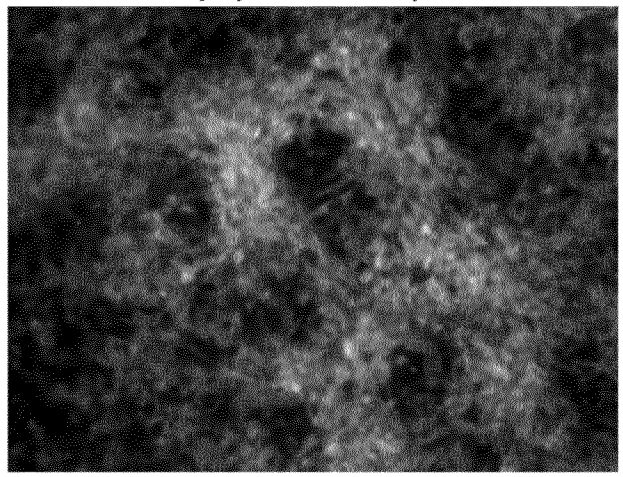
Figure 4B:
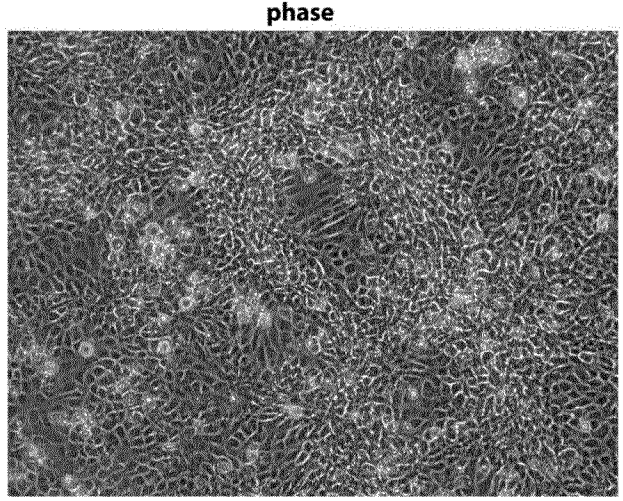
Figure 4C:
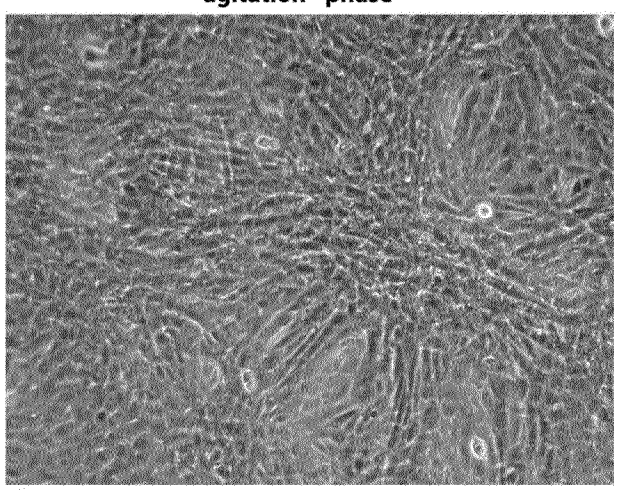
Figure 5A:
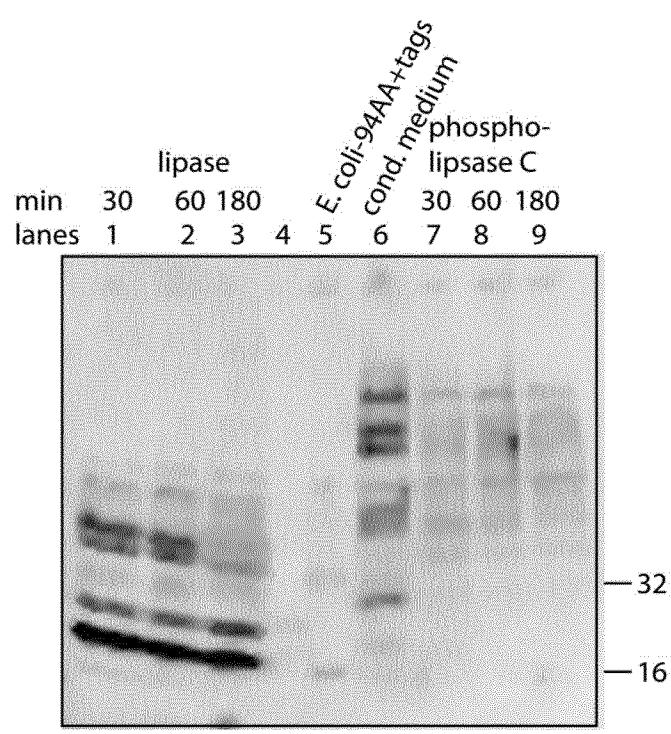
Figure 5B:
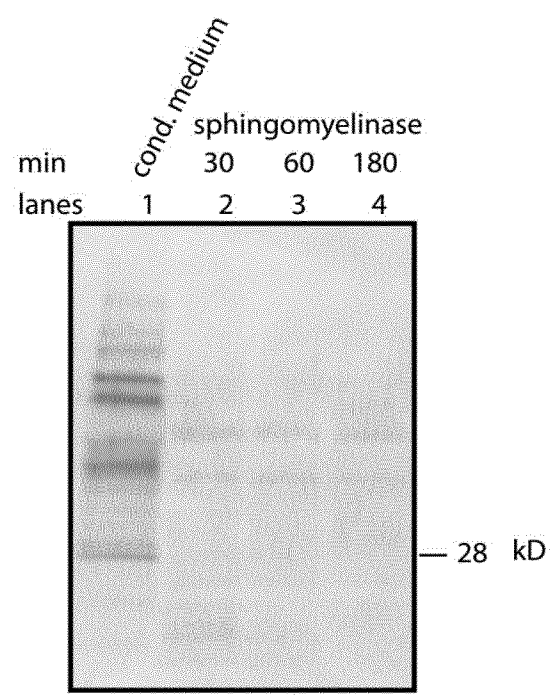
Figure 6:
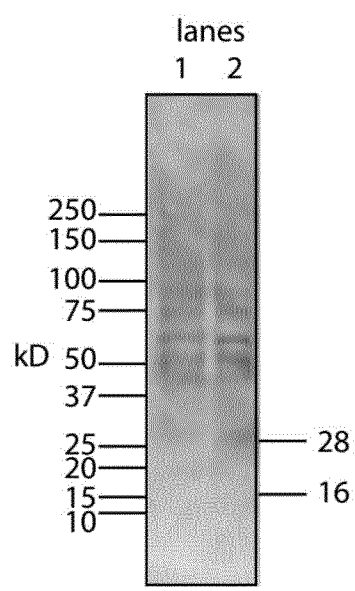
Figure 7:
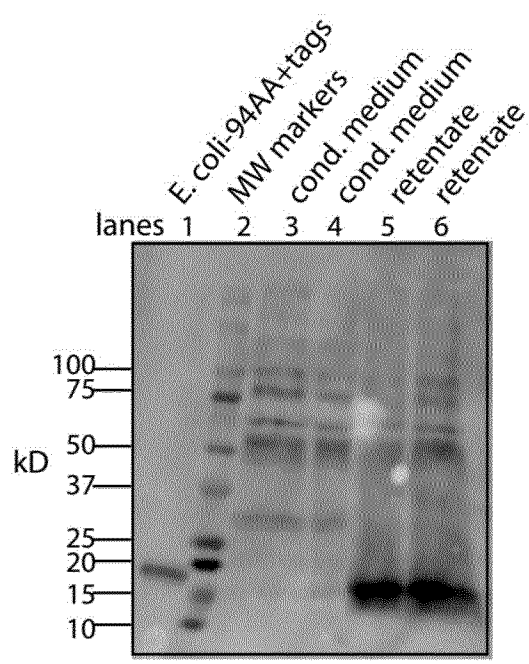
Figure 9:
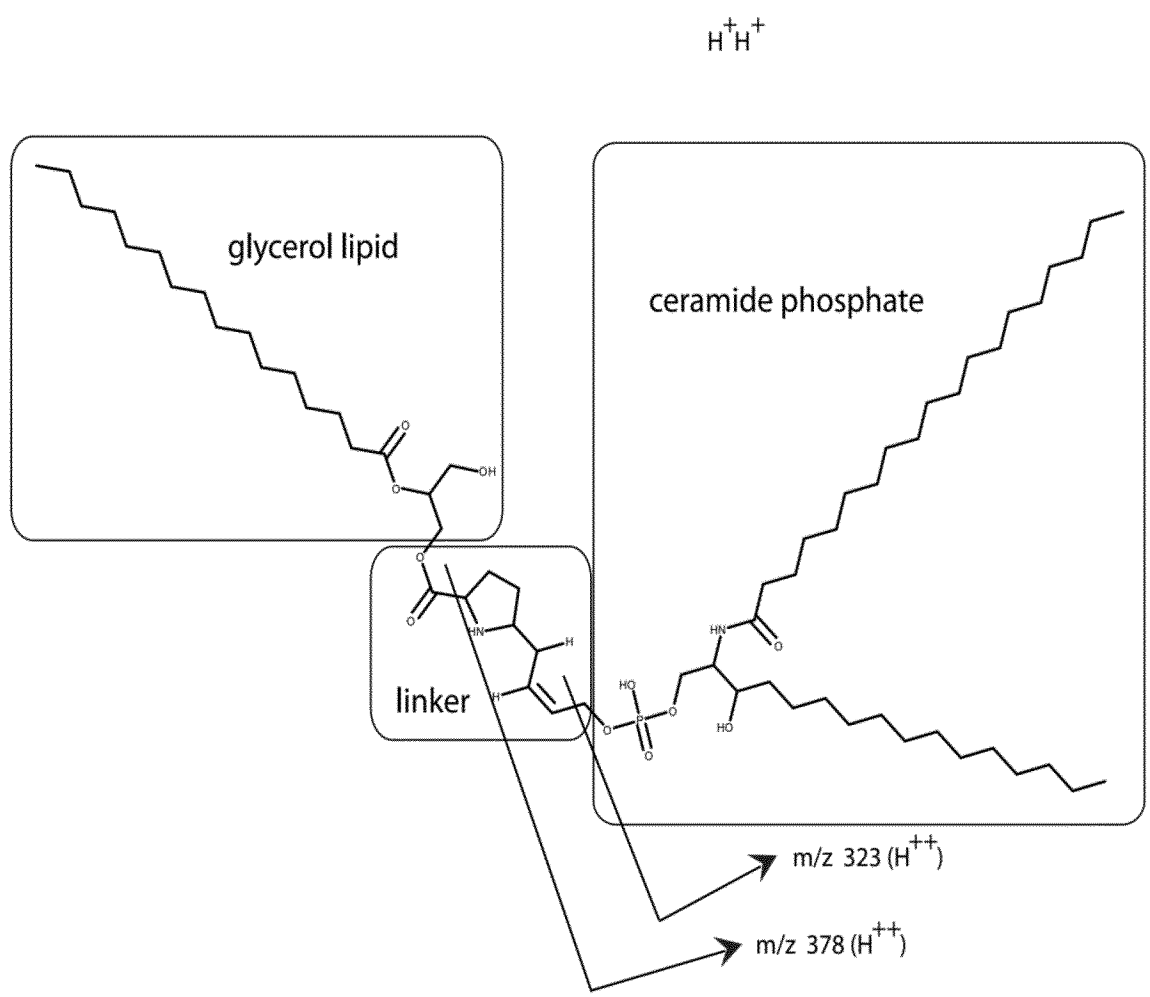
Figure 10:
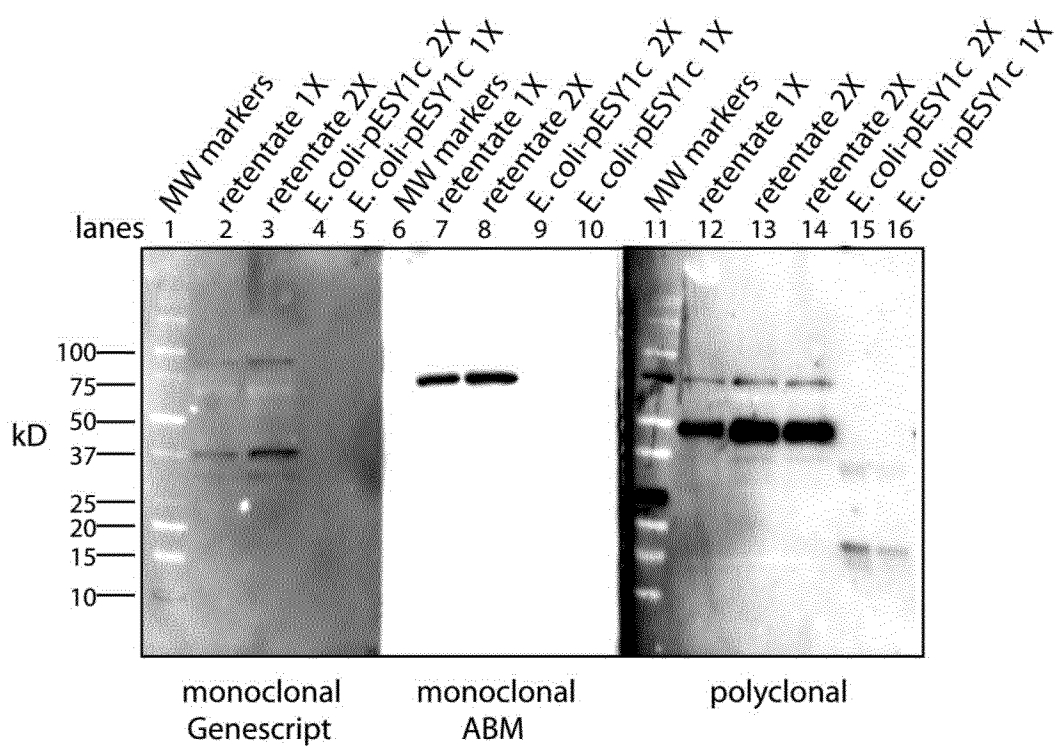

FIGS. 16A and 16B—Mammary gland from 5 week old mice were frozen and thick section (100 microns) were stained for the conserved protein component of the cell density signal (FIG. 16A; Alexa 488) and show strong staining in the endbud. The sections were also stained for nuclei using DAPI (FIG. 16B).

DETAILED DESCRIPTION OF THE PREFERRED EMBODIMENT

Introduction

Cell density is the critical parameter controlling tendon morphogenesis. Knowing its neighbors allows a cell to regulate correctly its own proliferation and collagen production. Previous work is described in U.S. Pat. Nos. 5,741,895; 6,245,899; and 6,433,136, which are incorporated by reference in their entirety, which identified an 14 amino acid (AA) sequence from chicken DNA, which shares the first 8 AA sequence with the cell density signaling protein isolated and described herein: EPLAVVDL (SEQ ID NO:1). We describe herein that in humans, SEQ ID NO:1 is part of a 424 AA gene product, highly conserved between chicken and human (89% identical). By cleavage the 8 AA sequence, towards the carboxy terminus, could begin a 94 AA secreted protein. The human cDNA that expresses the present protein is found in GenBank Accession No. AY398644.1 GI:38946311 and submitted as *Homo sapiens* tubulin-specific chaperone cofactor E-like protein mRNA. It was described by others in Bartolini, F., et al., "Identification of a novel tubulin-destabilizing protein related to the chaperone cofactor E," J. Cell. Sci. 118 (PT 6), 1197-1207 (2005). We describe herein that this protein is processed intracellularly to provide a secreted 94 AA protein (SEQ ID NO: 5) that is a cell-density signaling protein which interacts with a tissue-specific co-factor.

Using the chicken secreted 94 AA protein (SEQ ID NO:3) and various enzymes the cofactor was identified as a lipid. Through mass spectrometry, the cofactor was shown to be a 1114.89 MW molecule containing a ceramide phosphate, a single chained glycerol lipid and a linker. Chick tendon uses a different cofactor made up of two fatty acid chains linked directly to the phosphate yielding a molecule about half the size. Moreover, adding the tendon factor/cofactor to osteosarcoma cells causes them to stop growing which is opposite to its effects on tendon cells. Thus, it was found that the cofactor is cell type specific both in composition and in the triggered response. Further proof of its role came from frozen sections from 5 week old mice where an antibody to the factor stained strongly at the growing ends of the tendon as predicted. In conclusion, one part of the cell density signaling (CDS) mechanism is a small protein bound to a unique, tissue-specific phospholipid yielding a membrane associated but diffusible molecule.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the 94 amino acids of SEQ ID NO:3, 4, and 5), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

In some embodiments, constructs and methods are provided for transfecting or transforming a cell with a construct or expression cassette, the construct comprising a sequence that expresses a cell density signaling protein, and the expressed sequence being 60%, 65%, 70%, 75%, 80%, 85%, 90%, 95%, 96%, 97%, 98%, 99% or 100% identical or homologous to SEQ ID NOS:3, 4, 5, 7, 9, 12 or 13.

In some embodiments, the CDS nucleotide sequences of SEQ ID NOS:6, 8, or 14 or fragments thereof, may be inserted into a vector expression system. Suitable vectors include but are not limited to pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also used including but not limited to lentiviral, adenoviral, retroviral or sendai viral vectors. The expression system usable in a method with fragments of or the sequences of SEQ ID NOS:6 or 8 or 14 include any system utilizing RNA or DNA sequences. It can be used to transform transiently or stably in the selected host (bacteria, fungus, plant and animal cells). It includes any plasmid vectors, such as pUC, pBR, pBI, pGA, pNC derived vectors (for example pUC118, pBR322, pBI221 and pGAH). It also includes any viral DNA or RNA fragments derived from virus such as phage and retro-virus derived (TRBO, pEYK, LSNLsrc). Genes presented in the invention can be expressed by direct translation in case of RNA viral expression system, transcribed after in vivo recombination, downstream of promoter recognized by the host expression system (such as pLac, pVGB, pBAD, pPMA1, pGal4, pHXT7, pMet26, pCaMV-355, pCMV, pSV40, pEM-7, pNos, pUBQ10, pDET3, or pRBCS.) or downstream of a promoter present in the expression system (vector or linear DNA). Promoters can be from synthetic, viral, prokaryote and eukaryote origins. In some embodiments, the promoter is inducible to provide an inducible expression system as is known in the art. An example of such inducible expression system is a tetracycline-inducible expression system. In other embodiments, the promoter is tissue-specific and/or developmental stage-specific. These types of promoters may find use in the present constructs and methods as the lipid co-factor is tissue-specific, and the CDS protein-lipid complex is active at various developmental stages in various tissues.

The CDS sequences can be first cloned from cDNA, genomic DNA libraries or isolated using amplification techniques with oligonucleotide primers or synthesized. For example, sequences of candidate genes are typically isolated from nucleic acid (genomic or cDNA) libraries by hybridizing with a nucleic acid probe, the sequence of which can be derived from publicly available genomic sequence or the primers provided herein as SEQ ID NOS: 10 and 11, and 15 and 16. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA*, 72:3961-3965 (1975)).

In another embodiment, the CDS proteins are expressed in a tissue from any mammal including but not limited to, primates such as humans, monkeys, and chimpanzees; rodents, including mice and rats, domestic animals such as horses, dogs, cats, cattle, etc.

In various embodiments, methods are provided for expression of the CDS proteins in various tissue cells including but not limited to bone, breast, tendon, muscle, epithelial, epidermal, cartilage or secretory glands.

In another embodiment, methods and compositions are provided for expression of the CDS protein in a host cell to express the CDS protein recombinantly. After isolation and purification, the CDS protein can be provided to a cell to induce the formation of the CDS protein-lipid co-factor complex.

In another embodiment, an antibody is provided that binds to the CDS protein. The Examples also describe a polyclonal antibody that binds to the 94 AA chicken protein but also shows affinity for the human and mouse proteins. Methods for making a monoclonal antibody are known and humanizing the monoclonal antibody that specifically binds to or targets the CDS proteins of SEQ ID NOS: 3, 4, 5, 7, 9, 12 and/or 13 can be carried out by one of skill in the art.

In other embodiments, after expression of the CDS protein in a specific tissue, methods are provided for isolating the tissue-specific lipid co-factor. Filtering and separation methods including ultrafiltering to separate the protein from its lipid co-factor are also described.

Thus, in some embodiments, the invention also provides for the CDS protein bound to a tissue specific lipid co-factor. In one embodiment, a CDS protein bound to the lipid co-factor in FIG. 9. In another embodiment, a CDS protein bound to the lipid co-factor in FIG. 12.

Thus, in another embodiment, a protein-lipid complex comprising the CDS protein bound to a tissue specific lipid co-factor. In some embodiments, the CDS protein by itself has little or no observed biological activity. Its role is to give the complex the ability to diffuse from one cell to another. The protein/lipid complex builds up in the membrane of the cell only when there are increasing numbers of other cells in the surrounding vicinity. In some embodiments, the 94 AA secreted protein can be modified to provide for variants that still exhibit the function of binding to a lipid co-factor to enable cell density signaling. For example, the attachment of tags to the 94 AA secreted protein of at least 40 AA did not affect the activity and the modified 94 AA secreted protein was still active in bone cells. Evolution has made 9 significant changes in the 94 AA sequence and it is still active (see below for the comparison between chick and human CDS proteins and SEQ ID NO:4). It is contemplated that the CDS protein can be shortened (e.g., by 4 AA on the C-terminus), lengthened or modified to provide for variants yet still retain the property to bind to lipid cofactors of the correct cell type and acting to signal other cells to proliferate, differentiate, or apoptose.

Tissue-specific lipid cofactors that bind to the CDS protein were found. In one embodiment, the structure of the lipid cofactor in tendon is as shown in FIG. 12. In another embodiment, the structure of the lipid cofactor in bone is as shown in FIG. 9, having a ceramide phosphate, linker group, and a glycerol lipid. Variations of the lipid such as addition or deletion of acyl, glycerol, phosphate, methyl or other groups, shortening or lengthening of the linker or lipid chain length, or other known modifications or variations in lipids are also contemplated. Such variants are expected to retain the property of binding to the CDS protein to form a complex which acts to signal other cells to proliferate, differentiate, or apoptose.

Herein are provided examples of ultrafiltration protocols for isolating and purifying the lipid co-factors from the protein-lipid complex after expressing the CDS protein in cells or providing cells the isolated purified protein to form protein-lipid complexes. In some embodiments, the cells are grown in conditioned medium and allowed to form the protein-lipid complexes. In one embodiment, a series of filtration steps are carried out such as:

1) The conditioned medium is filtered through a 0.2 micron filter and then the salt concentration is raised by adding approximately ⅒th volume of 5M NaCl.

2) This high salt conditioned medium is concentrated to 1 ml using a YM-10 ultrafilter (Millipore) in a stirred cell using pressurized nitrogen.

3) The retentate is diluted to 10 ml with water and reconcentrated to 0.5 ml.

4) Most of the free protein factor remains in the retentate and this can be assayed by Western blots.

5) The free lipid cofactor is present in the filtrate.

In some embodiments, with new ultrafilters (e.g., from Millipore), the pretreatment of the filter with hydrophobic solvents and heating the cofactor in a hydrophobic buffer are additional necessary steps for the purification of the cofactor. In some embodiments, with new YM-10 filters (Millipore) the following changes are made for the separation to succeed:

1) The YM-10 filters need to be pretreated by soaking for 48 h in a 20% solution of acetonitrile in water at 37 degrees C. Other hydrophobic solutions will work but this is the best within the guidelines suggested by Millipore for their filters.

2) After concentrating the high salt conditioned medium to 1 ml, this was put into 10 ml of a more hydrophobic buffer (10 mM EDTA [pH 8.0], 2 ml acetonitrile, 3 ml isopropyl alcohol, 5 ml water) and heated at 80 degrees C. for 2 h. Again, this is the best hydrophobic buffer within the guidelines suggested by Millipore for their filters.

3) This heated conditioned medium was put back into the stirred cell and concentrated using the same YM-10 filter.

In various embodiments, the times and amounts for these protocols can be changed or optimized as determined by one having skill in the art.

In other embodiments, the lipid co-factor can be synthesized and added to purified recombinant CDS protein to allow the formation of the CDS protein-lipid co-factor complex.

In further embodiments, the CDS protein-lipid co-factor complex can be provided to a cell to enhance or modulate cell signaling. For example, the recombinant protein or the protein-lipid co-factor complex can be delivered to a tendon of an injured mammal to promote tendon repair.

In various embodiments, a cell's microenvironment concentration of the CDS protein-lipid co-factor complex is modulated to alter the signaling concentration in the cell microenvironment, thereby resulting in a change in the cell state. In one embodiment, modulation of the CDS protein-lipid co-factor complex in the bone cell microenvironment induced differentiation of the bone cell. In another embodiment, modulation of the CDS protein-lipid co-factor complex in a tendon cell microenvironment could also induce the tendon cell to undergo differentiation. In another embodiment, modulation of the CDS protein-lipid co-factor complex in the mammary gland cell microenvironment could induce ductal cell differentiation. And in another embodiment, modulation of the CDS protein-lipid co-factor complex in a malignant mammary cell microenvironment may be used to stop differentiation.

Therefore, in some embodiments, methods are described wherein the cell density signal protein-lipid complex is contacted to a cell to modulate cell type, induce differentiation, form fibrils filled with collagen, or form ducts, in a tissue-specific manner and at non-natural time points. In some embodiments, the complex is placed in the cell's microenvironment and the cell can be induced to differentiate or form these cell states or structures.

Example 1

Cell density is the critical parameter controlling tendon morphogenesis. Knowing its neighbors allows a cell to regulate correctly its own proliferation and collagen production. A missing link to understanding this process is the sensing mechanism. Previously, this mechanism was shown to rely on a diffusible factor with an affinity for the cell layer. Purifying and sequencing the band that best correlated with a cell proliferation assay yielded an 8 amino acid (AA) sequence that was part of a 424 AA gene product, highly conserved between chicken and human (89% identical). By cleavage the 8 AA sequence, towards the carboxy terminus, could begin a 94 AA secreted protein.

To validate its role, a construct of pEsy1c was made inserting the chicken cDNA (Exons 2-7; SEQ ID NO:14) to express the protein described in GenBank Accession No. XP_427094.2 GI:118101919 (SEQ ID NO: 12). pEsy1c was transfected into a human osteosarcoma cell line (U2OS) to test whether the recombinant protein would exhibit the expected activity on tendon cells. U2OS cells expressed the gene but not passively: differentiating into structures resembling spongy bone and expressing alkaline phosphatase, an early bone marker. Intracellularly, two bands were observed: the full length protein (44 kD) and a smaller form (26 kD). Outside the cell, a 28 kD band was detected as well as multiple larger bands. These larger forms could be converted to a 16 kD form by changing salt concentrations and ultrafiltering—releasing a cofactor to the filtrate while leaving a protein factor in the retentate. Using various enzymes the cofactor was identified as a lipid. Through mass spectrometry, the cofactor was shown to be a 1114.89 MW molecule containing a ceramide phosphate, a single chained glycerol lipid and a linker. Chick tendon uses a different cofactor made up of two fatty acid chains linked directly to the phosphate yielding a molecule about half the size. Moreover, adding the tendon factor/cofactor to osteosarcoma cells causes them to stop growing which is opposite to its effects on tendon cells. The cofactor is cell type specific both in composition and in the triggered response. Further proof of its role came from frozen sections from 5 week old mice where an antibody to the factor stained strongly at the growing ends of the tendon as predicted. In conclusion, one part of the cell density signaling mechanism is a small protein bound to a unique, tissue-specific phospholipid yielding a membrane associated but diffusible molecule.

Our long-term goal is to resolve how cells sense cell density and then tie this signaling to the induction of prolyl hydroxylase. To begin to understand cell density regulation, PAT cells were grown as a 6 mm island in the middle of a 60 mm dish[12]. The cells in middle of the island grow to be confluent while cells at the edge of the island would grow outwards to be at low cell density. In this way, cells at multiple cell densities could be studied at the same time. Indeed, when one probed the levels of procollagen mRNA by in situ hybridization, the level dramatically increased from the edge of the island to the confluent center[12]. Growing cells as an island was useful but it made a change that turned out to be much more significant: the ratio of medium to cells was increased 100 fold. While gently agitating PAT cells confluent over the whole dish had no effect, gently agitating PAT cells grown as an island caused a dramatic change in both cell proliferation and procollagen production[12,13]. The reason for this difference is that cells confluent over the whole dish could condition the medium such that shaking only increased the rate at which the factor exchanged locations between the medium and the cell layer and not its concentration. When grown as an island of cells, there was too much medium and the factor released from the cell layer was basically lost. The lower concentration of this factor strongly altered the ability of PAT cells to sense the cells around them. To identify the complete molecular nature of this factor is a focus of the following Example.

The Gene

Previously 400 liters of conditioned media (using gentle agitation) from primary avian tendon (PAT) cells were put through 4 columns and the band on an SDS gel running at 16 kD tracked best with activity (stimulating an island of PAT cells to proliferate) was sequenced and yielded: EPLAVVDLTEKTIS (SEQ ID NO:2) [14]. This chicken sequence does not have an immediate correspondence to the human equivalent for two reasons. First, as with all N-terminal Edman sequence data, with each cycle the noise level increases reducing the confidence of each additional read. Not unexpectedly, the chicken genome shows an exact homology only with the first 8 AA. Second, the human genome has a variant in the fifth position from V to E. Nevertheless, this 8 letter AA sequence in the chicken comes from a much larger gene with a gene product of 424 AA in seven exons. The homology between the chicken and the human genes at the amino acid level is 89% identical and 94% positive.

```
Chick        1  EPLAVVDLRPQSSVKVEVHFQDKVEEMSIRLDQTVAELKKHLKTVVQLSTSNMLLFYLDQ  60
consensus       EPLA VDLRPQSS KVEVHF D+VEEMSIRLDQTVAELKK LKT+VQL TSNMLL+Y D
Human           EPLAEVDLRPQSSAKVEVHFNDQVEEMSIRLDQTVAELKKQLKTLVQLPTSNMLLYYFDH
1366

Chick       61  EAPFGPEEMKYSSRALHSYGIRDGDKIYVEPRMK (SEQ ID NO: 3)                94
consensus       EAPFGPEEMKYSSRALHS+GIRDGDKIYVE + K (SEQ ID NO: 4)
Human           EAPFGPEEMKYSSRALHSFGIRDGDKIYVESKTK (SEQ ID NO: 5)
```

High homology in the amino acid sequence between chick and human secreted protein factor. The chick sequence (top line) has 80 out of 94 amino acids that are identical (85%) to the human sequence (bottom). In addition, of the 14 amino acids that differ between these sequences, 5 are considered positive in that the substitution is predicted to act in a similar manner. This is shown in the consensus line (middle sequence, SEQ ID NO:4)) where identical amino acids are shown with their letter, positive changes with a "+" sign, and other changes by a blank.

For this large gene to be correct requires further processing: a cleavage just before the EPLAVVDL sequence (SEQ ID NO:1) of the larger predicted expressed protein of SEQ ID NO:9 would give the right starting sequence since this sequence is found near the carboxy end and thus produces a small secreted protein with 94 AA (SEQ ID NO:3, or 5).

In summary, the high homology between chicken and human is striking for such a distant relationship from a common ancestor but this does not confirm a significant role for this protein. Moreover, the potential 94 AA protein is small for the observed molecule weight on SDS gels of 16 kD inferring that if this is the correct gene that some modification or tightly bound cofactor may be involved. The next step is to test whether this is the correct gene.

Example 2: Results—Expression in U2OS Cells

The classic proof that a gene codes for a given function is to clone it, express it in a different cell type, and then show that the purified recombinant protein has the same activity on the original cells. In this case, the chicken gene could be cloned and expressed in a non-chicken cell line. The secreted form could be purified from shaken, conditioned media and tested on PAT cells for its ability to stimulate cell proliferation on confluent cultures seeded as an island in the middle of a dish. To simplify detection and purification of the recombinant protein, a myc and his tag were added to the carboxy end. A replication defective retroviral vector containing a neomycin resistance gene was used to transfect the chicken gene into U2OS cells[15,16]. Because this prior study was started when the chicken genome was first sequenced, the chicken equivalent to the first exon was not present in GenBank or public sequence repository. So the insert described contained only the last six exons (pESY1c). Pattern of Molecular Expression Intracellularly and Extracellularly The expression of pESY1c in U2OS cells directed a unique phenotype in human bone cells derived from an osteosarcoma tumor but the putative processing of a large transcript to obtain a much smaller protein outside the cell requires further confirmation. Because the U2OS cells expressed a myc and his tagged chicken cDNA, the processing of this large protein could be observed by Western blotting. The nucleotide sequence coded for 423 AA including an additional 3 AA at the 5' end and 41 AA at the 3' end encoding the two tags (myc and his). Extrapolating from what we had seen in PAT cells, this should be cleaved to a 94 AA small protein plus a 41 AA tag and secreted from the cell. Despite its small size, in PAT cells the 94 AA protein ran with an apparent MW of 16 kD on SDS gels; extrapolating, the tagged protein would be predicted to have an apparent MW of ~20 kD.

Figure 2:
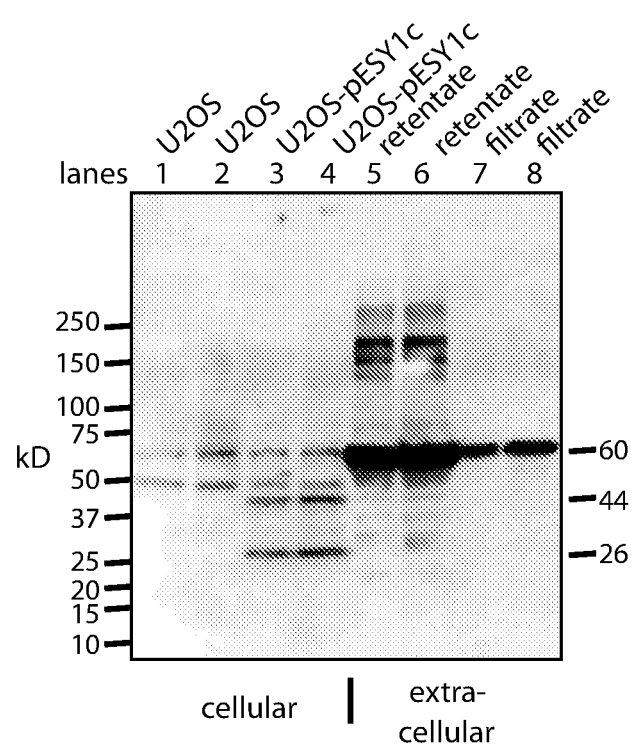
FIG. 2—Western analysis of U2OS-pESY1c expression both inside and outside the cell. The monoclonal antibody to the myc tag (clone 4A6) detects c-myc inside the cell so control U2OS cells were used to identify the background bands (lanes 1, 2). For each condition, two lanes were run on an SDS gel where the second was loaded with twice the sample. U2OS cells expressing pESY1c showed two additional bands—a full length protein at 44 kD and a smaller band at 26 kD (lanes 3, 4).

A monoclonal myc antibody and Western blotting was used to probe the expression and processing of this myc tagged gene. Since c-myc would also be expressed inside the cell, uninfected U2OS cells were used to identify those intracellular bands (FIG. 2). Two new bands were seen intracellularly: ~44 kD band which is expected for the full size gene product; ~26 kD band that could be a cleavage product since the protein sequenced from PAT cell conditioned medium does not start with a methionine. However, this band is larger than the predicted 20 kD protein.

To observe the secreted forms, a simple purification was used whereby the CM was put through a 30 kD ultrafilter. Both the retentate and the filtrate were analyzed and both had to be further concentrated on a 10 kD ultrafilter in order to load sufficient protein on the gel for Western analysis. The retentate has many bands (FIG. 2): the smallest is a weak band at ~28 kD, the strongest is at ~60 kD, and the largest is over 200 kD. The filtrate shows basically a single band at ~60 kD. This is unusual since 60 kD proteins are excluded to a high degree from passing through a 30 kD ultrafilter. One possible explanation of the data is that the need to concentrate ~20 fold has caused the tagged protein to aggregate into stable forms that resist the denaturing effects of heat, beta mercaptoethanol, and SDS.

In summary, this data shows both positive and negative findings. Intracellularly, the large protein does get processed to a smaller form but this appears larger than predicted. A smaller tagged protein does get secreted outside the cell but this protein is larger than expected and it appears to aggregate to stable forms when concentrated.

Aggregation is Due to a Cofactor

The multiple bands seen in the Western blot complicates the interpretation of how this tagged protein is working in the extracellular space. But more specifically, even the smallest MW band (~28 kD) seen outside the cell is higher than predicted. We asked whether this larger size due to a different amount or type of modification in bone cells versus tendon cells, or was this increase in apparent MW a reflection of an interaction with another molecule.

To begin to answer these questions, we needed to resolve how the unmodified protein factor with two tags migrates on a Western. To accomplish this, the tagged protein was expressed in E. coli, purified on a nickel column, and then used as a standard in Western blots. The tagged protein ran with a MW of 16 kD (FIG. 3, lane 6). This confirms that there is either a covalent modification or a binding to another molecule that gives rise to the 28 kD form in U2OS cells. Further aggregation could then occur when concentrating the factor to give rise to larger MW forms.

This raises the question of whether different physical and chemical modifications could alter the size of the bands observed on Western. CM from U2OS-pESY1c was put through a YM30 (YM is the type and 30[kD] is the pore size [Millipore]) ultrafilter and the filtrate was then concentrated on a YM10 ultrafilter. This was divided into 2 parts. One was further concentrated on a YM10 ultrafilter for loading on a gel but in this case, 30% DMSO was added. To the other sample was added salt (0.5 M); concentrated with an ultrafilter; then diluted to low salt; and then concentrated to apply to a gel (FIG. 3). The effect of DMSO was to reduce the number of bands, especially those at high MW, but the smallest band still remained 28 kD. In contrast, the treatment with high salt, low salt and ultrafiltration yielded a much simpler picture where the bands were reduced to the 16 kD band and its dimer at 32 kD. One can conclude that the 28 kD band is due to a binding of a cofactor and not a covalent modification.

Example 3: Purification, Localization and Characterization of the Factor/Cofactor in the Extracellular Space The previous experiment raises the question of how the untagged 16 kD form in tendon cells compares to the 28 kD tagged form seen in bone cells. Even taking into account a 4 kD tag, there is an additional 8 kD shift in MW. Are these forms variations with common characteristics or is the bone form acting in a different manner? In tendon cells the 16 kD form is loosely bound to the cell layer. This gives a key feature to this form in that gently shaking a flask of tendon cells causes them to lose their ability to sense high cell density, resulting in increased proliferation.

First, the localization was examined with immunofluorescence using a rabbit polyclonal antibody specific to the tagged secreted form of the chicken protein expressed in *E. coli*. During tests to optimize the signal, procedures that disrupted membranes decreased the signal. Using an optimized protocol, immunofluorescence staining was localized to areas where the cells have overgrown the monolayer (hills) and expression was suppressed in monolayer areas (valleys) (FIG. 4a).

Second, the cells were subjected to gentle shaking (100 rpm) for 3 h per day with the medium changed each hour. After 3 days the hills had spread into the valleys and the valleys had additional growth. The net effect was to even out the growth over the flask (FIG. 4c).

One can conclude that some of the major physical properties of the bone and chicken factor/cofactor are the same. They are both localized to the cell layer—most likely bound to the cell membrane. However, this interaction is not strong, allowing significant diffusion that can be enhanced by gentle agitation of the medium. The effect of the signal on the cells is cell type specific in that the bone cells try to form a lattice network in order to form spongy bone (FIG. 1b) while the tendon cells try to form a growth plate to make small tubes filled with collagen—fibrils[7].

Characterization of the Bone Cofactor

The cofactor is tightly bound to the factor: the interaction is stable to SDS, heat, and gel electrophoresis. This tight binding makes purification of the cofactor difficult, but is useful in giving a consistent mobility pattern on Western blots. This pattern could then be used to test whether specific degradative enzymes could cleave the cofactor and alter the migration profile.

One possible candidate for the cofactor would be a variation on the anchoring structure for membrane bound proteins: a glycosylphosphatidylinositol lipid[18]. To test for a glycolipid, the factor/cofactor was treated with a variety of polysaccharide degradative enzymes—chondroitinase ABC, hyaluronidase, heparinase—and then the pattern on a Western was compared to that of an untreated control. None of the treated samples showed a distinct change in the pattern (data not shown). At the same time, a variety of lipid degrading enzymes were tested—lipase, phospholipase $A_2$, phospholipase C, and sphingomyelinase. Lipase, phospholipase C, and sphingomyelinase caused dramatic shifts in the pattern seen on Westerns (FIG. 5). Lipase was most dramatic in that it caused bands to shift to lower MW including the 16 kD, free protein form. The lipase was a crude preparation used at a high concentration; so while its primary target would be a glycerol fatty acid linkage in the cofactor, this is probably not the only cleavage product. The phospholipase C used in this experiment has overlapping activities with the sphingomyelinase. The sphingomyelinase is more specific to cleaving moieties on ceramide phosphates. In contrast, phospholipase $A_2$ did not show a significant change in mobility or intensity (data not shown). A negative result is hard to interpret because there are too many potential causes. The positive results, while not yielding a definitive structure, implicate lipid components containing a phosphoceramide and a glycerol fatty acid as part of the cofactor. The lipid nature of the cofactor can explain why the factor/cofactor has a strong tendency to aggregate when concentrated due to hydrophobic interactions.

Purification and Characterization of the Cofactor

In order to characterize the cofactor in more detail, procedures needed to be developed that separate both the factor from the cofactor and then the cofactor from other lipid-like molecules. One serious handicap to developing this purification scheme is the lack of a direct assay for the cofactor. In addition, most common lipid identification procedures use quantities that are far greater than what can be obtained easily from CM. The one method with sufficient sensitivity is mass spectrometry. This method requires at the very least that the purification yield a good signal to noise ratio.

The first step in the purification—the separation of the cofactor from the factor—might benefit from standard lipid procedures using a methanol/chloroform extraction. In this procedure the lipids are found in the chloroform layer and proteins are found as a precipitate between the layers. There is no assay for the cofactor but the proteins in the precipitate can be solubilized and then Western analysis can be used to see if the protein factor runs as the free form (16 kD) or as a complex with the cofactor (28 kD). The amount of free factor is an indicator of cofactor release. However, redissolving the protein precipitates at the interface and running Western blots only showed the 28 kD form and higher order aggregates (FIG. 6). In this extraction protocol, the cofactor remains bound to the factor and as a consequence, precipitates at the interface.

Despite attempts to weaken the interaction between the factor and the cofactor by changes in pH, salt, solvent, chaotropic agents, temperature, and chelating agents, Western blots showed little or no conversion to the free form (data not shown). The only successful method required a combination of a shift in salt concentration and ultrafiltration (FIG. 3). Using a simplified version of this procedure whereby the CM was made high in salt (~0.6 M) and then concentrated on a 10 kD ultrafilter. This was then diluted 10 fold with water and concentrated to run on Westerns (FIG. 7). By intensity of the bands, most of the tagged factor runs as the free form. Thus, the corresponding free cofactor was expected to have passed through the ultrafilter as part of the filtrate.

Using differential solvent elution from a small C18 resin column to concentrate and purify lipids and then comparing the untreated and the enzyme treated samples via mass spectrometry one can identify candidate cofactors (FIG. 8). Only molecular weights between 530 and 580 are shown because there was no significant differences between the samples at either higher or lower values (mass range=m/z 300-m/z 1500). Two doubly-charged ions at m/z 543.4273 and m/z 557.4429 are dramatically reduced by treatment with either enzyme and these peaks are not observed in the control and the intensity of the m/z 557 ion is highly correlated with the intensity of the free protein factor in the retentate. The observed difference between the doubly-charged ions is 14 representing a 28 Da difference in MW commonly seen for lipids. In the rest of the analysis, we focused on the 557 species with a MW of 1114.8858. By using a high mass accuracy Q-TOf mass spectrometer we generated potential molecular formulas with a list of atoms commonly found in organic biomolecules (i.e., carbon, hydrogen, nitrogen, oxygen, and phosphorous). The most likely formula C63H123N2O11P (exact mass=557.4432252+; 0.6 ppm from the measured mass) had nearly a 1:2 Carbon:Hydrogen ratio common to lipids and the nitrogen, oxygen and phosphorous indicative of a hydrophilic region. Support for the proposed cofactor structure derived from MS/MS fragmentation of m/z 557. Two fragment ions, shown in FIG. 9, at m/z of 323 and m/z 378 are consistent with a ceramide phosphate and a linker moiety, supporting the results from the enzymatic reactions.

From our analysis, the cofactor is susceptible to three lipid enzymes—lipase, phospholipase C, and sphingomyelinase, and a peak observed at m/z 557 that has a strong lipid composition. This peak is lost when treated with lipase, phopholipase C, and sphingomyelinase. Using our knowledge of which enzymes cleave the cofactor and the molecular formula, a working model can be postulated that includes a ceramide phosphate and a glycerol lipid with a linker consisting of a short modification of a proline residue between them (FIG. 9).

Antibody Interactions with a Protein/Lipid

Antibody affinity to a protein could be strongly affected by a lipid cofactor. This became an issue when the monoclonal antibody (clone 4A6, Millipore) to the myc tag stopped working. Over the course of these experiments Millipore changed the storage buffer several times and finally to a liquid stored at 4° C. This latter change reduced the affinity of the antibody so that only the free protein factor was detected (data not shown). The benefit of the antibody from the 4A6 clone is that it "recognizes and is specific for recombinant proteins containing the Myc epitope tag in a variety of sequence contexts." Other clones are known to show strong affinity differences depending on the protein attached to the myc tag. Add a lipid cofactor to a protein with a myc tag and it is unclear how a context sensitive antibody would bind. To find an adequate replacement, three alternatives were tested: a rabbit polyclonal antibody to the secreted form of the factor (94 AA+tags) expressed in *E. coli*; a monoclonal antibody to the myc tag from Applied Biological Materials (clone A7) and one from GenScript (clone 2G8D5). Using the same CM sample for each antibody yields a Western blot that is unique to the probing antibody (FIG. 10). Critical to our purification procedure for the cofactor, only the polyclonal antibody can detect the free factor at our test concentration of ~0.5 ng as well as bands with the factor/cofactor. Most importantly, one cannot compare the intensity of one band to that of another because each antibody has its preferred conformations; instead, one can only compare the relative amount of a specific band after different treatments.

The Tendon Cofactor Characterization

Having analyzed the bone factor/cofactor, the focus returned to the original aim of characterizing the tendon factor except with the knowledge that it binds a cofactor. The bone and tendon cofactors must be different because they impart a unique shift in mobility to the factor/cofactor complex on SDS gels. In tendon the protein portion codes for ~10 kD but it runs with an apparent MW of 16 kD. One can approximate the cofactor influence as adding ~6 kD to the MW. In the case of bone cells (U2OS), the factor is larger due to the myc and his tags, ~14 kD yet it runs at a MW of 28 kD. The cofactor influence is ~14 kD but this is actually due to a lipid with a MW of 1.1 kD. This raises important questions about the nature of the tendon cofactor and how it compares to its bone counterpart.

As a first step, the lipid enzymes that were used to characterize the bone cofactor were tested on PAT cell CM. In this case, concentrated CM was used that was over 6 months old. This results in a stable aggregate at ~60 kD being the dominant band. As with bone, ligase and phospholipase C were active on the PAT cell factor/cofactor and phospholipase $A_2$ was inactive (FIG. 11a). The main difference was that sphingomyelinase was inactive on the PAT cell factor/cofactor (FIG. 11b). To insure that the inactivity of the enzyme was not due to the factor/cofactor being in a specific aggregate, the treatment with sphingomyelinase was repeated with fresh CM (FIG. 11c). The result remained unchanged. This indicates a lack of a ceramide phosphate in the tendon cofactor.

The cofactor was purified for mass spec. by binding it to a small C18 column and washing with methanol, acetonitrile, and then, eluting with chloroform. We compared preparations that were treated with either phosphospholipase C or lipase while the cofactor was bound to the C18 column to the untreated cofactor samples. No differences were seen in the methanol or acetonitrile washes. The chloroform elution did show several bands that changed between the untreated and treated samples. Two of the peaks, 668.61 and 696.65 were reduced to background levels by the enzyme treatments. These peaks are related in that they differ by 28 MW and reflect variation a lipid chain length by two carbons. But there was another negative fact that needs to be pointed out—there was no 557 doubly charged peak in the tendon cofactor spectrum (data not shown). The same medium and the same purification scheme yields different candidate molecules depending on the cell type conditioning the medium.

Using ms/ms to further characterize the 668.61 band yielded a rather simple spectrum with two bands of roughly equal intensity and with MW of 283.26 and 311.29. These differ by 28 and correspond to saturated fatty acids with 18 and 20 carbons respectively. Both chains are required to be in the model in order to achieve the high lipid content indicated by the parent molecule's MW. Since the band is degraded by phospholipase C, there is a phosphate group but there is insufficient mass to include a glycerol phosphate. Instead an ester links the fatty acid directly to the phosphate. Our proposed structure adds a cyano group to the phosphate and is consistent with the enzymology and the mass spec. data (FIG. 12).

Nomenclature

With two different cofactors and the potential for more in the future, there is a need to give them distinct names. For the bone factor/cofactor will be named SNZR 1P1L; for tendon factor/cofactor will be named SNZR 1P2L. Similarly, the protein factor will be SNZR 1P and the bone cofactor, SNZR 1L and the tendon cofactor, SNZR 2L. At present, because of the extremely high homology between species at the protein level and no knowledge of the conservation of lipid structure between species, the delineation is only on cell type.

Cofactor Specificity

The cofactor for bone and the cofactor for tendon are unique. The SNZR 1P can bind either SNZR 1L or SNZR 2L and drive a unique differentiation pathway dependent on the type of cofactor produced by the cell. This raises the question of whether the SNZR 1P2L when added to U2OS cells is capable of driving bone differentiation or does it elicit a new or null response? In addition, one can ask whether the protein factor, by itself, has any activity?

To answer these questions, U2OS cells were grown in regular media as a control, or with 5× concentrated condition media from U2OS-pESY1c cells expressing the SNZR 1P1L, and from 5× concentrated condition media from PAT cells expressing SNZR 1P2L. In addition, SNZR 1P purified from *E. coli*, was added at 5 μg/ml—3 orders of magnitude greater than the estimated level in CM (FIG. 13a,b,c,d). These levels were chosen because early work with PAT cells have shown that 1×CM is insufficient to stimulate growth when added back to confluent cultures (Zayas & Schwarz 1992). The high level of the protein factor was chosen because it seemed unlikely that the factor without the cofactor would have a lot of activity and small amounts of activity are difficult to detect by visualization.

Figure 1A:
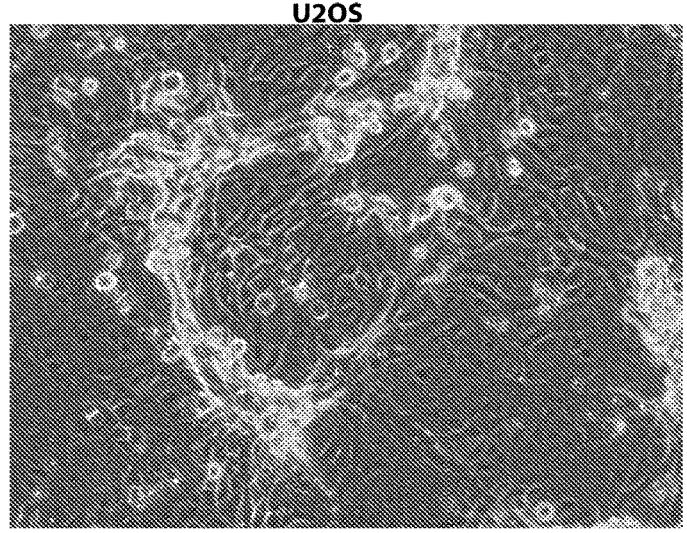
FIGS. 1A, 1B and 1C—Expression of the cDNA, pESY1c, causes human osteosarcoma cells (U2OS) to differentiate. Control U2OS cells do overgrow the monolayer but cannot sustain growth necessary to form structures (FIG. 1A). U2OS-pESY1c cells, after becoming confluent (end of week 1), the cells begin to overgrow the monolayer. First as linear short stripes but these coalesce into small circles and then finally some of the common borders recede and the circles become larger (week 3, phase contrast, FIG. 1B). When U2OS-pESY1c cells get to the stage of differentiation where they are making large circles of overgrown cells, they start to produce alkaline phosphatase, an early marker of bone development. In this assay using brightfield microscopy, the overgrowing cells turn dark, an indicator of alkaline phosphatase activity, while the confluent cells inside the circle express little or no activity (FIG. 1C). The bars=100 µm.
Figure 1B:
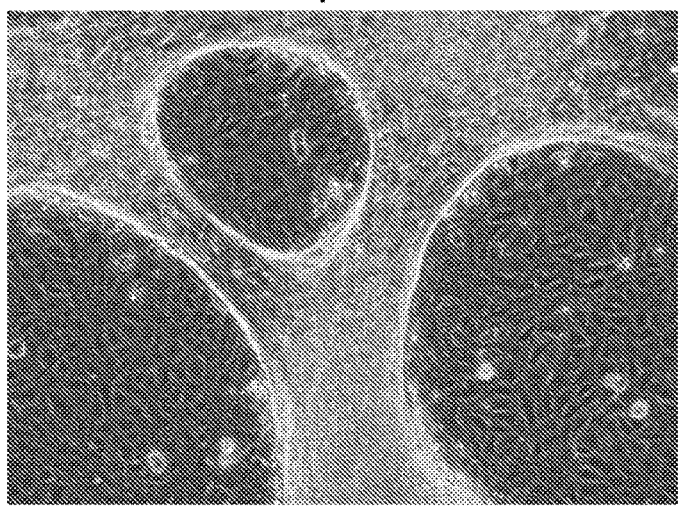
Figure 1C:
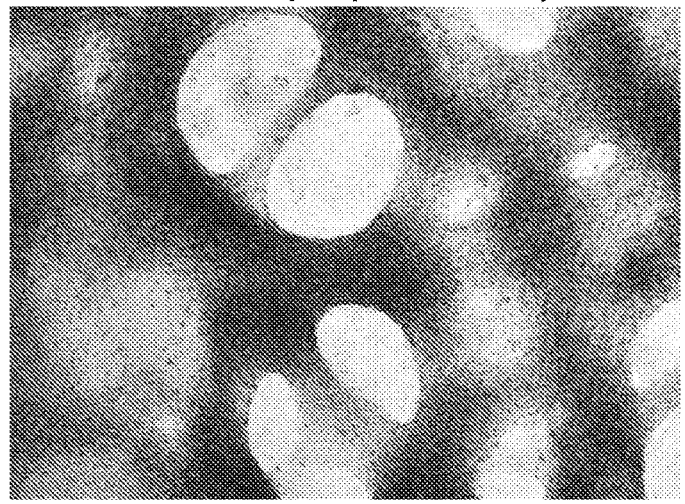

After a week in the various media, the most dramatic effect was that the tendon CM was inhibitory to growth when added to the U2OS cells yielding a subconfluent culture. The addition of the SNZR 1P alone did not appear to change the cultures compared to the control even at this high concentration. Adding 5×CM from U2OS cells expressing the SNZR 1P1L, showed some increased in growth as the cells appeared to be more compact. However, to confirm this observation we allowed this flask and its control to grow for additional 9 days, at which point it was obvious that the CM had caused the cells to completely overgrow the monolayer (FIG. 13e,f). What is particularly striking is uniformity of growth when the CM is added to cells versus the lattice patterns that are formed when the cells themselves express the SNZR 1P1L (FIG. 1b).

One aim of this Example—producing the recombinant form of the tendon cell density signal in another cell type and then applying it to tendon cells to show it has the original activity—is not compatible with our data. Since the cofactor that is essential for activity is unique (in two cases) to the cell type producing it, another test would be useful in showing that the protein factor is the correct candidate for being part of the cell density signaling mechanism. There is the similarity that both the tendon SNZR 1P2L and bone SNZR 1P1L are loosely bound to the cell layer and cause the cells to differentiate. In addition, the polyclonal antibody to the 94 AA protein does detect a band at 16 kD in the PAT cell CM (FIG. 11C). A more functional test would further confirm the identity.

To accomplish this, the polyclonal antibody was used to check whether the factor was at the tendon/muscle junction of 5 week old mice. This is the growing stage for mice and one would predict that the factor would be at high concentration at the growing ends of the tendon; where there should also be a high density of fibroblasts (Schwarz 1996). To detect the protein factor, a polyclonal rabbit antibody was used with a secondary antibody labeled with Alexa 568; to detect the nuclei, the sections were stained with DAPI (FIG. 14).

At the growing end of the tendon there is a strong fluorescence signal for the factor (FIG. 14a) as well as numerous nuclei labeled with DAPI (FIG. 14b). There is variation in the signal over the length of the tendon but this can result from the plane of the tendon not being in exactly the same plane as the section. The strong staining for the factor at the growth plate of the tendon supports its role as a cell density signal.

As a control, a preimmune serum was used at an equal concentration and exposed for equal time and it is basically negative (FIG. 14c) and the DAPI staining shows the tendon nuclei starting at the lower left corner and rising steeply to the top of the picture (FIG. 14d).

One unexpected observation is the light staining of the muscle connective tissue with its single file nuclei (FIG. 14a,b). This is an indication that a third cell type may be producing this protein factor along with its own unique cofactor.

Discussion

In 1976, we showed that freshly isolated chicken embryonic tendon cells were exquisitely sensitive to cell density as reflected in the levels of procollagen production[19]. Despite this dramatic regulation of the most important protein in tendon morphogenesis, the paper went on to say that the "mechanism by which one cell communicates its presence to another cell is unclear." A few years and many experiments later the signaling mechanism is now shown to use a tight complex between a protein and a lipid. The protein is a small cleavage product from the carboxy end of a larger gene product and this small protein is subsequently secreted from the cell. The protein itself appears to have little or no activity but requires the binding of a lipid cofactor. Remarkably, the composition of the lipid is tissue-specific. While only two types have been characterized, they are each unique in both the lipid structure and the triggered response.

SNZR 1P is also unique in composition, processing, and function. By being able to bind unique phospholipids, SNZR 1P allows diffusion into the medium of a lipid that would otherwise be expected to be tightly embedded in the membrane. In earlier papers, this trait was described as being "loosely bound to the cell layer" an explanation for its ability to localize to the cell layer but be partially removable by gentle agitation[12,13,20]. Being able to identify SNZR 1P and its lipid partners gives this complex a molecular identity that explains its unusual characteristics. In addition, as more has become known about the SNZR 1P1L, similarities can be seen to other signaling molecules—in particular, sonic hedgehog. There is no sequence homology but they are both made as large transcripts that are processed to a smaller protein and then secreted from the cell[21]. In the case of sonic hedgehog, it is the N-terminus that is secreted and in this case, it is the C-terminus. The activity of sonic hedgehog is greatly enhanced by the covalent linkage of palmitate and/or cholesterol[22]; with the cell density signaling protein itself has little activity but this is greatly enhanced by binding to a lipid cofactor. Because of the lipid attachments, sonic hedgehog runs as an aggregate on SDS gels[23]. The binding of the cofactor causes a similar effect on the SNZR 1P. On the other hand, the differences are equally important: SNZR 1P can bind a variety of lipids and in doing so can change its signaling function in a tissue specific manner. Besides how this complicates the analysis of gene function, the result is that the cell has the ability to sense both the type and number of cells in its immediate vicinity and thereby react accordingly. Given the nature of the complex, the simplest hypothesis is that the protein holds the lipid in a specific conformation that can then bind to the cell membrane and organize it[24]. With more cells there would be additional binding resulting in a more organized plasma membrane and this would trigger a stronger signal transduction.

But we should point out that our focus has been on the carboxy end of the transcript yet the rest of the protein is equally well conserved between the chick and the human. Another group searching for homology to other tubulin stabilizing proteins found a 20% overlap with this gene[25]. By Northern analysis, many tissues appeared to transcribe this gene at low levels while testis produced it in larger amounts. Over expressing this gene in HeLa cells caused tubulin to be destabilized in contrast to their initial selection criteria. Because they tagged the transcript at the amino terminus, the secreted form would have gone undetected. Moreover, they pointed out that they could not distinguish whether the destabilization of tubulin was a direct or an indirect effect. If the effect on tubulin was an indirect effect of cell density signaling in HeLa cells, then the conservation of sequence could be as simple as conserving the 3-dimensional structure of the cleavage site, or another alternative could be as an intracellular part of the cell density signaling process. The role of the larger, N-terminus protein, will require further analysis to resolve why it is so highly conserved.

Our focus has been on molecular characterization of the sensing mechanism for cell density regulation that generates a proliferative signal, but the cell usually requires a more sophisticated response. For instance, in U2OS-pESY1c cells expressing SNZR 1P1L one might postulate that as the cells overgrow the monolayer they begin to produce a secreted inhibitor to prevent the cells in the valleys from producing SNZR 1P1L and dividing: a classic Turing model[26,27]. In tendon cells, more is known and with the knowledge of the cofactor one can adjust a previous model to reveal how cells form a growth plate and then fill a growing tube (fibril) with collagen. To do this the cells need a timer, a growth stimulator, a growth inhibitor and a trigger for apoptosis. Mathematical modeling has shown that this can be accomplished with two factors and the cell[7]. The first factor stimulates growth and the production of the second factor. The second factor, which does not diffuse into the medium; has no activity on its own but by interacting with the first factor changes it to an inhibitor of growth, and a stimulator of procollagen synthesis. Cells left at high cell density cause a drop in production of the first factor triggering apoptosis. The first factor can now be seen as SNZR 1P2L that we have described. The second factor has until now been hypothetical but a good candidate would be the free cofactor (SNZR 2L). Their interactions occur in the plasma membrane and their consequences are predicted to further organize the membrane structure that in turn can alter the internal state of the cell.

In a permissive cell culture environment for tendon cells—very low serum (0.2%) and addition of ascorbate—these factors come to the forefront and results in the "peculiar" behavior of primary cells in culture[6-8,12,13,17,19]. The cells isolated from 16 day chick embryos were programmed to rapidly make a tendon by way of a growth plate in order that the hatched chick is able to walk to find food and water. In the research laboratory, however, we wanted tendon cells to conform to normal cell culture protocol: grow on a 2-dimensional plastic surface from low density to high density; then be trypsinized off the plastic and the process repeated. Meanwhile the cells were trying to interpret these changes in terms of its own programming for generating a tendon—a collagen rope—by regulating collagen production and cell proliferation. As a result we found that: PAT cells only made high levels of procollagen at high cell density (~50% of total protein synthesis). Left at high cell density for several days procollagen production declines. Splitting high density cultures resulted in cells that grew to a lower confluent density and produced a lower level of procollagen. Seeding cells a low cell density resulted in uneven cell growth. Seeding cells at low cell density as a small island in the middle of a dish resulted in the whole island apoptosing after a few hours. Gentle agitation of confluent cells seeded as an island in the middle of dish—high medium to cell ratio—caused cells to grow. Adding back CM to an island of confluent cells caused cells to grow. Taking all this information and developing a 2 factor model to explain it was the first step; the second step was to mathematically model the behavior of the cells in 3-dimensional space. Their programming generated a growth plate that was confirmed in vivo at the tendon/muscle junction[7].

At the growth plate one can postulate how tendon cells normally respond: at the leading edge cells at moderate cell density are growing driven by their production of the SNZR 1P2L. As one moves towards the trailing edge the cell density increases as does the level of SNZR 2L. This slows proliferation and increase procollagen production. At the trailing edge the cells have been at high cell density producing high levels of procollagen for a longer time and this causes a decrease in the SNZR 1P. This drop triggers apoptosis although some cells at the periphery of the tube (fibril) survive. This is only an outline with the principal players identified (FIG. 15). Nevertheless, a "peculiar" behavior in one setting, becomes "normal" in another.

Analyzing molecular changes raises the question of why does the cell need an additional method for signal transduction? Why not use a protein to activate a receptor? Or put another way, what is the advantage of using a diffusible lipid? In the case of activating a receptor, the cell responds in a graded manner in a set direction. Adding a growth factor can stimulate a cascade of events that results in more rapid cell proliferation. However, the participation of a cell within a growth plate is a far more complex process requiring the cell to respond to parameters related to both space and time. By detecting the levels of SNZR 1P2L and SNZR 2L, the cell can determine its location within the growth plate, whether it should be growing or slowing down, producing high levels of procollagen, or apoptosing. Having a diffusible lipid be a major signal makes the system sensitive to subtle and rapid changes; and with all of the sensors and modifiers acting in one place creates the biological equivalent of an analog logic board allowing the cell to respond to a complex environment correctly.

Key elements to this "circuit" require unique lipids yet this is not a common type. Because the tissue specific lipids are present at low concentrations, their detection is difficult. We were only able to analyze the two unique lipids because of their tight binding to a protein to which we had both tag and polyclonal antibodies. On the other hand, the tight binding of a protein made purification by standard lipid extraction methods impossible. But the critical observation is that production of a chick protein made in tendon with high homology to the human equivalent causes a unique human bone lipid to be produced. This makes the protein look like a cassette that can bind a variety of different lipids. Based on the observations described herein, it is expected that there are many different tissue specific lipids that bind the protein to form this complex. Thus, if the proteins are in tendon that uses a growth plate to form tubes filled with collagen, we would also expect to see unique lipids in other tissues that form tubes—filled (structural tissues) and unfilled (ductal glands)—using a growth plate or end buds. Similarly we have seen one case where two cell types share a common protein. Given the disparate types of cells where this protein is found—bone, tendon and mammary gland—it is likely that many cell types share this protein or variants specific for each cell types with unique lipids for each of those cell types comprising many unique cell density signals in an organism.

And in other embodiments, the formation of this unique complex provides a novel therapeutic for tendon repair. Future testing in vivo will include providing this complex in sufficient concentration to a damaged tendon can be driven to form a new growth plate by injecting a tendon cell density signal and thereby heal a damaged tendon with speed and strength. These signals are potent and specific agents that drive the morphogenesis of tissues. In cell culture, expressing the universal protein part of the signal in an osteosarcoma cell line (U205) caused these cells to make their own tissue-specific lipid cofactor, and differentiate into spongy bone in a 2-dimensional space. Despite malignant transformation and having been in culture for 50 years, they retain the response to cell density signaling.

Example 4: Materials and Methods for Examples

Cells and Cell Culture

PAT cells were isolated from 16 day chick embryos by a modification of the procedures described by Dehm and Prockop[30]. Specifically, a higher serum level (3%) was used in the dissociation medium and the use of a nylon mesh (20 micron; TETKO) instead of filter paper to separate out single cells. In these experiments the medium was changed from F12 to a 50/50 mix of F12/DMEM in order to be consistent with the medium used to grow the U2OS cells. The medium contained 0.2% fetal bovine serum deactivated for 30 m at 56° C.

U2OS cells were grown in F12/DMEM medium with 0.2% fetal bovine serum. In 75 cm² flasks the medium, 50-75 mls, was changed every other day. When the cells first overgrow the monolayer, they are very sensitive to medium volume and will apoptose if too much medium is added.

CM was produced by growing cells in 225 cm² flasks. Medium was changed and reduced to 12 mls of serum-free medium. The flasks were placed in an environmental rotator at 100 rpm, 37° C. for 1 h. The CM was collected and new medium added, and the process was repeated for the third hour. After the 3$^{rd}$ collection medium with serum was added and the flask returned to the regular incubator.

Alkaline Phosphatase Assay

The Sigma kit was used (85L2-1KT) and the included procedures were followed with only slight modifications for labeling tissue culture flasks instead of slides.

Genes, Cloning and Expression

RNA was extracted from confluent cultures of PAT cells using Trizol (Invitrogen). The RNA was reversed transcribed using superscript II (Invitrogen). The cDNA was amplified by PCR using proof reading taq polymerase (Invitrogen) using primers from the 5' end of exon 2 plus a methionine start site and the 3' end of exon 7.

```
Forward primer:
                             (SEQ ID NO: 10)
GCTGGATCCATGAAAGACCGTCTCAACCTTCCA Reverse primer:
                             (SEQ ID NO: 11)
ACAGAATTCGACTTCATCCTGGGCTCC
```

This was cloned into the vector pcDNA3.1/Myc-His(+) A,B,C (Invitrogen) and sequenced. The sequence agreed with the predicted expression of this gene (minus exon 1; accession: XP_427094). Using primers for standard T7 promoter/priming site and the BGH Reverse priming site with the addition of a Sal1 site, the gene with tags was amplified using PCR. It was TOPO cloned (Invtrogen) to enhance Sal1 activity and then cut with BamH1 and Sal1. This was ligated to pESY-Neo-II (Koh et al. 2002; Lee 2007), a retroviral vector, that had also been cut with BamH1 and Sal1.

In summary, at the time the sequence for the chicken exon 1 was not known, so a 3 AA sequence containing methionine was added to the 5' end (above the dashed line below) and myc and his tags added to the 3' end (below the dashed line below). This polynucleotide (SEQ ID NO:14) was inserted into a retroviral vector pESY-Neo-II—retroviral pEYK 3.1 was modified to remove the GFP and bleomycin DNA and replace it with Neo/Kan antibiotic resistance gene and a multi-cloning site (Lee 2007) and renamed pESY1c which when expressed provides the following protein herein identified as SEQ ID NO: 12:

```
MKD
----------------------------------------
----------------------------------------
R L N L P S V L V L N S C G I T C A G
D E N E I A A F C A H V S E L D L S D
N K L E D W H E V
S K I V S N V P H L E F L N L S
S N P L S V L E R R C
A G S F A G V R K L V L N N S K A
S W E T V H T I L Q E L P D
L E E L F L C L N D Y E T V S C S P V
C C Q S L K L L H I T D N N L Q D W T
E I R K L G I M F P S L D T L I L A N
N N L I T I E E S E D S L A R L F P N
L R S I N L H K S G
L H C W E D I D K L N S F P K L E E V
K L L G I P L Q S Y T T E E R
R K L L I A R L P S I I K L N G S I V
G D G E R E D S E R F F I R Y Y M E F
P E E E V P F R Y H E L I T K Y G K L
E P L A V V D L R P Q S S V K V E V H
F Q D K V E E M S I R L D Q T V A E L K K H
L K T V V Q L S T S N M L L F Y
L D Q E A P F G P E E M K Y S S R A L H S Y
G I R D G D K I Y V E P R M K
----------------------------------------
----------------------------------------
S N S A D I Q H S G G R S S L E G P R
F E Q K L I S E E D L N M H I G H H H
H H H
```

Alternating normal and bold/italic fonts indicate exons and the underlined AAs in last exon indicate the secreted form of the gene (94 AA).

The vector pESY1c (4 μg/60 mm² dish) was used to transfect phoenix cells using lipofectamine 2000 using the manufactures protocol (Invitrogen). The cells were incubated overnight and the next day medium was collected, filtered (0.45μ), and used to transfect pESY1c into U2OS cells in the presence of 8 μg/ml polybrene. The transfected cells were selected using G418 (100 μg/ml).

Polyclonal Antibody

The secreted form of pEsy1c (underlined AA above, 94AA; SEQ ID NO:13)) with a methionine at the N-terminus (above dashed line) was inserted into the *E. coli* expression vector pTrcHis2-TOPO (Invitrogen). The vector included myc and his tags at the C-terminus (below lower dashed line) produces the secreted form of the protein shown below (SEQ ID NO:13). The primers used are shown below as well.

M
--------------------------------------
--------------------------------------
E P L A V V D L R P Q S S V K V E V

H F Q D K V E E M S I R L D Q T V A E L

K K H L K T V V Q L S T S N M L L F Y L

D Q E A P F G P E E M K Y S S R A L

H S Y G I R D G D K I Y V E P R M K
--------------------------------------
--------------------------------------
D D D D K K G E F E A Y V E Q K L I S

E E D L N S A V D H H H H H H

Forward primer:
(SEQ ID NO: 15)
GTGACCATGGAGCCCTTGGCAGTCGTGGAT

Reverse primer:
(SEQ ID NO: 16)
CTTATCGTCATCGTCCTTCATCCTGGGCTC

The prokaryotic expression vector yielded an expressed protein that was 7 AA smaller in the linker between the protein and the tags (the variation is a function of the type of multiple cloning site and the primers used in cloning) and 1 AA larger at the N-terminus. This difference was too small to detect on gels and the linker region was not important for antibody production. The protein was expressed in *E. coli* and purified and nickel columns (Invitrogen). This protein (4 mg) was used to immunize rabbits and for affinity purification (Biosynthesis). This protein was also used as a standard for the secreted form of the factor with tags.

Immunofluorescence

Cell culture: cells were fixed with 4% paraformaldehyde for 10 m in a high calcium buffer (0.05M TES pH 7.2, 0.1M NaCl, 0.05M CaCl$_2$). The fixation was quenched with two, five minute washes in buffer A (0.05M TES pH 7.2, 0.1M NaCl, 0.01M CaCl$_2$) containing 0.1M glycine. A blocking agent (1% casein Hammerstein [EM Science]) was used for 30 m followed by a rinse with buffer A. The primary antibody was a polyclonal made in rabbits against the secreted form of pESY1c plus tags expressed in *E. coli*. This was added at 1:40 (the antibody was diluted by 25% with stabilizer [Candor]) for 2 h with agitation. Then, washed 3× with buffer A with agitation and then a fluorescently tagged goat anti-rabbit secondary was added for 1 h with agitation. Washed 3× with buffer A and then once with a DAPI buffer (500 nM in PBS). Finally, a wash with buffer A.

Tissue sections: hind legs from 5 week old mice were dissected to reveal the muscle and the attached tendon. These were embedded in OCT (Sakura) for 10 to 30 m and then frozen in small embedding molds in a dry ice/ethanol bath. Frozen tissue was sliced into 16µ sections and attached to superfrost plus slides (VWR). The sections on the slide were outlined with a pap pen and then analyzed as described above. In this case, because the tendon had less autofluoresence in the red, this was the preferred color for the secondary emission. Because the plane of the knife and the plane of the tendon were infrequently in agreement, the analysis required many legs and sections.

Western Analysis.

Samples were concentrated on 10 kD spin ultrafilters (Millipore) diluted with 2× sample buffer and concentrated again to <200 µl and 40 µl or less was applied and run on an SDS gel (4-20%, 1.5 mm, 10 well, Tris-Glycine [Invitrogen]). The gels were blotted onto nitrocellulose (0.45µ), washed with water, and dried overnight. Next, the blots were washed with water and blocked with 1% Hammerstein casein for ½ h. After 2× water washes the primary antibody (monoclonal myc (Millipore) or polyclonal rabbit, see above) was added at 1:1000 in PBS with 0.25% casein Hammerstein for 2 h. The blot was then washed 3× for 5 m in PBS with 0.02% Tween 20. After which the rabbit secondary antibody conjugated to horseradish peroxidase (Thermo) was added at 1:1000 in PBS with 0.25% casein. Again the blot was washed 3× for 5 m in PBS with 0.02% Tween 20 and then developed with a Dura or Femto kits (Thermo). The blots were photographed with a FluoroChem HD2 (ProteinSimple).

Cofactor Purification

The NaCl level of the CM (see above) was increased by adding 1/10 the volume with 5M NaCl. This was concentrated to 1 ml in a stirred cell (Millipore), at 700 rpm and pressurized (14 psi, N$_2$). The filter was a YM-10 with a nominal cutoff at 10 kD (Millipore). The retentate was diluted to 10 ml with water and reconcentrated to 0.5 ml. The retentate was analyzed on Westerns to see the level of free factor released.

The filtrate containing the cofactor was concentrated using a Pierce C18 spin column (Thermo). The column was wetted with 1 ml of 50% acetonitrile/water and then spun for 1 m at moderate speed in a clinical centrifuge. Then, 1 ml of the filtrate was added and spun and repeated until all the filtrate was bound to the column. After which the column was washed twice with 1 ml of water, and twice with 1 ml of acetonitrile. Then, the washing was repeated: 1 ml of 50% acetonitrile, 1 ml water, 2×750 µl acetonitrile, and elute with 2×750 µl of chloroform. Samples were stored in chloroform and concentrated before analysis by blowing down with nitrogen to ~100 All solvents were LC, MS, or HPLC grade.

With recently purchased YM-10 filters (in comparison to using older filters from the original maker Amicon), the cofactor would not separate from the factor unless the following changes were made: the filters had to soak at 37° C. in 20% acetonitrile for 48 h; after concentrating the high salt CM to 1 ml, it was put into 10 ml of buffer (10 mM EDTA, 2 ml acetonitrile, 3 ml isopropyl alcohol, 5 ml water) and heated to 80° C. for 2 h and then concentrated to 0.5 ml. The filtrate was further concentrated and purified as described above.

Lipid Enzyme Treatment

Lipid enzymes were first used to identify the makeup of the cofactor. In this case, we were looking for a change in the mobility of factor/cofactor on a SDS gel after being treated with these enzymes for various times 30 m, 90 m, 180 m, and a no enzyme control. CM (3 ml) was concentrated to 0.5 ml. Then the enzymes were added as detailed below and incubated for the specific time, 2× sample buffer was added to stop the reaction, concentrated on a 10 kD ultrafilter, and analyzed by Western blotting.

Lipase: Sigma (L8525); 380 units/µl; added 50 µl; incubated 37° C. in buffer B (see below)

Phospholipase C: Sigma (P7633); 0.038 units/µl; added 50 µl; incubated 37° C. in buffer B Phospholipase A$_2$: Sigma (P9279); 6 units/µl; added 50 µl; made 20 mM triethanolamine pH 8.9 substituted for TES in buffer B; incubated room temperature Sphingomyelinase: Sigma (S9396); 0.54 units/µl; added 2 µl in buffer B with MgCl$_2$ substituted for CaCl$_2$; incubated 37° C.

The second use of lipid enzymes was to identify the peaks on mass spectrometry that were sensitive the enzyme treatment. In the cofactor purification above, between the wash steps, the column material was resuspended in buffer B (20 mM TES pH 7.2; 10 mM NaCl; 1 mM $CaCl_2$) and incubated for 30 min at 37° C. with agitation. This was spun down and the protocol above continued. In the buffer, when using sphingomyelinase, $CaCl_2$ was replaced with $MgCl_2$.

Mass Spectrometry Analysis

The diluted lipid extract samples were analyzed on an ABSciex TripleTOF 5600 (AB Sciex, Foster City, Calif.). Samples were introduced to the mass spectrometer via syringe pump by using a Nanospray III source (ABSciex) with a nano-tip emitter (New Objective, Woburn, Mass.) operating in positive-ion mode (2400 V). The data were acquired with Analyst TF 1.5.1 by averaging the signal from 400 m/z to 1250 m/z over several minutes. MS/MS spectra were collected in "high sensitivity" mode with the quadrupole set to UNIT resolution and collision energy set to 30 to optimize fragmentation. MS/MS spectra were scanned from 100 m/z to 1600 m/z and were collected for a total accumulation time of 500 ms.

Example 5: Cofactor in Mammary Gland Formation

Mammary gland from 5 week old mice were frozen and thick section (100 microns) were stained for the conserved protein component of the cell density signal (FIG. 16A; alexa 488) and show strong staining in the endbud. The sections were also stained for nuclei using DAPI (FIG. 16B). Detection of the presence of the co-factor in mammary gland cells also supports that this cofactor is found in various tissue types.

Example 6: Protein-Lipid Co-Factor Complex as a Cancer Treatment

A New Strategy for Cancer Treatment.

The standard approach searches for new ways to differentially inhibit the growth of malignant cells. Side effects in normal cells and the ability of malignant cells to develop resistance limits its effectiveness. In contrast, our strategy is to use strong differentiation signals to trump the malignant state and drive the cell towards normal morphogenesis. The limitation of this approach has been the scarcity of tissue-specific, strong differentiation signaling reagents.

Evolution has spent thousands of years stabilizing the differentiated state. Cells are hardwired to respond to strong differentiation signals. For the rare malignant cell and its progeny that have drifted from their stable state, the best solution is using strong differentiation signals to push them towards normal morphogenesis. One of those strong differentiation signals is cell density. Cell density is signaled using a highly conserved small protein bound to a unique tissue-specific lipid.

The prevailing theory is that malignant transformation is irreversible. Mutations lock the cancer cell into a proliferative state that continues until the organism dies. In which case, the only solution is to differentially attack the malignant cells and hope to destroy them or at least slow their growth. Evolution, on the other hand, has worked over thousands of generations to insure the stability of the differentiated state. Cancer is rare: most humans with 10 trillion cells can live 80+ years without a significant malignant transformation. This requires that strong differentiation signals be dominant over most mutations. For instance, in neuroblastoma in babies something is produced in the body at ~1½ years that causes these malignant cells to differentiate and act normally. Tumors formed after the age of 2 are very difficult to treat. In retinoblastoma, even with RB mutations, the rate of malignant tumors is vastly greater in children under the age of 6. Even teratocarcinoma cell lines act normally in their expected environment (blastocyst) and malignant if placed in an adult environment. A reasonable hypothesis is that the correct signals, e.g., in the microenvironment, drive a cell to act normally.

Our work has focused on how cell density stimulates differentiation and slows proliferation. This is taken as almost a cell biology axiom, yet the signaling mechanism has up until now been elusive. Moreover, tumor cells in vivo and in culture have lost their sensitivity to this signaling and continue to proliferate. The question one would like to ask if you had a supply of a cell density signal could you reinstate cell density regulation on a malignant cell if you added sufficient quantities. Our aim was to understand cell density signaling in tendon cells and in doing so we expressed a protein candidate in an osteosarcoma cell line (U2OS). These cells came from a malignant tumor in a female teenager and have been in culture for 50 years. Yet expressing this protein (and the cell produced a tissue-specific lipid cofactor) caused these cells to start growing like spongy bone and expressing an early marker of bone differentiation. The original U2OS cells appear to be the worst situation. The U2OS cells make a low amount of cell density signal and this stimulates growth but not differentiation. If the U2OS cells increased the amount of cell density signal they made, they would differentiate; if they made less they would stop growing. As a teenager's height shifts from rapid growth spurts to no growth as an adult, the bone cells must switch from rapid proliferation to no overall growth and yet, the original U2OS cells never fully accomplished this transition. The present model suggests that cell density signals may be used to cure osteosarcomas. Used as a therapeutic they are tissue-specific and normal signaling agents so they should have low toxicity and high specificity. As a consequence, the presently described cell density signals could reduce the fear of cancer and its treatment side effects while improving outcomes.

Cell density signaling is used by most cell types. Because the signal is a common protein and tissue-specific lipid, the potential use in many cell types remains to be tested. Thus, tissues with ducts such as prostate, breast, and lung cancers could be successful targets.

REFERENCES

1. Aaronson S A, Todaro G J (1968) Basis for the acquisition of malignant potential by mouse cells cultivated in vitro. Science 162: 1024-1026.
2. Kaldis P, Richardson H E (2012) When cell cycle meets development. Development 139: 225-230.
3. Pardee A B (1987) The yang and yin of cell proliferation: an overview. J Cell Physiol Suppl 5: 107-110.
4. Vogel A, Ross R, Raines E (1980) Role of serum components in the density-dependent inhibition of growth of cells in culture. J Cell Biology 85: 377-385.
5. Rowe L B, Schwarz R I (1983) Role of procollagen mRNA levels in controlling the rate of procollagen synthesis. Molecular and Cellular Biology 3: 241-249.
6. Schwarz R I, Bissell M J (1977) Dependence of the differentiated state on the cellular environment: modulation of collagen synthesis in tendon cells. Proceedings of National Academy of Sciences, USA 74: 4453-4457.
7. Schwarz R I (1996) Modeling tendon morphogenesis in vivo based on cell density signaling in cell culture. Journal of Mathematical Biology 35: 97-113.

8. Schwarz R I, Farson D A, Bissell M J (1979) Requirements for maintaining the embryonic state of avian tendon cells in culture. In Vitro 15: 941-948.
9. Lyons B L, Schwarz R I (1984) Ascorbate stimulation of PAT cells causes an increase in transcription rates and a decrease in degradation rates of procollagen mRNA. Nucleic Acids Research 12: 2569-2579.
10. Schwarz R I (1985) Procollagen secretion meets the minimum requirements for the rate-controlling step in the ascorbate induction of procollagen synthesis. Journal of Biological Chemistry 260: 3045-3049.
11. Lee E H, Kao W W-Y, Schwarz R I (2001) Cell density regulates prolyl 4-hydroxylase activity independent of mRNA levels. Matrix Biology 19: 779-782.
12. Schwarz R I (1991) Cell-to-cell signaling in the regulation of procollagen expression in primary avian tendon cells. In Vitro Cell and Developmental Biology 27a: 698-706.
13. Zayas J R, Schwarz R I (1992) Evidence supporting the role of a proteinaceous, loosely bound extracellular molecule in the cell density signaling between tendon cells. In Vitro Cell and Developmental Biology 28A: 745-754.
14. Schwarz R I (2002) Cell density signal protein suitable for treatment of connective tissue injuries and defects. In: Patent US, editor. USA.
15. Lee S-Y (2007) Identification and characterization of novel genes involved in signaling. Berkeley, Calif.: University of California, Berkeley.
16. Koh E Y, Chen T, Daley G Q (2002) Novel retroviral vectors to facilitate expression screens in mammalian cells. Nucleic Acids Res 30: e142.
17. Valmassoi J, Schwarz R I (1988) High serum levels interfere with the normal differentiated state of avian tendon cells by altering translational regulation. Experimental Cell Research 176: 268-280.
18. Paulick M G, Berozzi C R (2008) The glycosylphosphatidylinositol anchor: a complex membrane-anchoring structure for proteins. Biochemistry 47: 6991-7000.
19. Schwarz R I, Colarusso L, Doty P (1976) Maintenance of differentiation in primary avian tendon cells. Experimental Cell Research 102: 63-71.
20. Stoker M G P (1973) Role of diffusion boundary layer in contact inhibition of growth. Nature 246: 200-203.
21. Weed M, Mundlos S, Olsen B R (1997) The role of sonic hedgehog in vertebrate development. Matrix Biology 16: 53-58.
22. Taylor F R, Wen D, Garber E A, Carmillo A N, Baker D P, et al. (2001) Enhanced potency of human sonic hedgehog by hydrophobic modification. Biochemistry 40: 4359-4371.
23. Goetz J A, Singh S, Suber L M, Kull F J, Robbins D J (2006) A highly conserved amino-terminal region of sonic hedgehog is required for the formation of its freely diffusible multimemeric form. Journal of Biological Chemistry 281: 4087-4093.
24. Simons K, Toomre D (2000) Lipid rafts and signal transduction. Nature Reviews Molecular Cell Biology 1: 31-41.
25. Bartolini F, Guoling T, Piehl M, Cassimeris L, Lewis S A, et al. (2005) Identification of a novel tubulin-destabilizing protein related to the chaperone cofactor E. Journal of Cell Science 118: 1197-1207.
26. Murray J D (1988) How the leopard gets its spots. Scientific American 256: 80-87.
27. Turing A M (1952) The chemical basis of morphogenesis. Philos Trans Roy Soc 237: 37-72.
28. Weaver V M, Peterson O W, Wang F, Larabell C A, Briand P, et al. (1997) Reversion of the malignant phenotype of human breast cells in three-dimensional cultures and in vivo by integrin blocking antibodies. Journal of Cell Biology 137: 231-245.
29. Postovit L-M, Seftor E A, Seftor R E B, Hendricks J C (2006) A three-dimensional model to study the epigenetic effects induced by the microenvironment of human embryonic stem cells. Stem Cells 24: 501-505.
30. Dehm P, Prockop D J (1971) Synthesis and extrusion of collagen by freshly isolated cells from chick embryo tendon. Biochim Biophys Acta 240: 358-369.

The above examples are provided to illustrate the invention but not to limit its scope. Other variants of the invention will be readily apparent to one of ordinary skill in the art and are encompassed by the appended claims. All publications, databases, accessions, and patents cited herein are hereby incorporated by reference for all purposes.

---

SEQUENCE LISTING

```
IB-3190US

Schwarz, Richard I.

SEQ ID NO: 1
Gallus Gallus
First 8 amino acids of CDS sequence identified in US Pat. No. 6433136
EPLAVVDL SEQ ID NO: 2
Gallus Gallus
14 amino acid CDS sequence identified in US Pat. No. 6433136
EPLAVVDLTEKTIS SEQ ID NO: 3
Gallus Gallus
94 aa cell density signal
EPLAVVDLRP QSSVKVEVHF QDKVEEMSIR LDQTVAELKK HLKTVVQLST SNMLLFYLDQ
EAPFGPEEMK YSSRALHSYG IRDGDKIYVE PRMK SEQ ID NO: 4
Artificial
94 aa cell density signal consensus
See specification

SEQ ID NO: 5
```

SEQUENCE LISTING

*Homo sapiens*
94 aa cell density signal
EPLAEVDLRP QSSAKVEVHF NDQVEEMSIR LDQTVAELKK QLKTLVQLPT SNMLLYYFDH
EAPFGPEEMK YSSRALHSFG IRDGDKIYVE SKTK SEQ ID NO: 6
AY398644.1 GI:38946311
*Homo sapiens* tubulin-specific chaperone cofactor E-like protein
mRNA, complete cds

```
   1 acactgggct ccggcggcca gagtggggga ctaggtgaag cggcgccggg ccggggctgg
  61 ccgggaccag gcccgaggct gagcggcggc gacagcggtg gccgggaggg gggaggagag
 121 gcgcagccag aggagccgcc gcagtagctc ccccgcctcc cgggctgagg gcattttaag
 181 aaagaaagat ggatcaacct agtggaagaa gtttcatgca agtattatgt gaaaaatata
 241 gtcctgaaaa ttttccttat cgccgtggcc cggggatgga agtccatgtc ccagccacac
 301 ctcagggctc tcctatgaaa gatcgcctca acctcccaag tgtactagtg ttgaacagct
 361 gtggaataac ctgtgcagga gatgaaaaag aaattgctgc tttctgcgct catgtgtcgg
 421 aactagatct ttctgacaac aaactcgaag actggcatga ggtcagtaaa attgtgtcaa
 481 atgttcctca gttggagttt ctaaacctga gttccaaccc tctgaatttg tcggttttag
 541 aaagaacatg tgctgggtcc ttctctgggg ttcgcaaact tgtcctcaac aacagcaaag
 601 cttcttggga gacggtccac atgatactac aggagttacc agatttggag gagctcttcc
 661 tgtgccttaa tgactatgaa acagtgtctt gtccttctat ttgctgtcat tctcttaagc
 721 tactacatat aacagacaat aacctccaag actggactga aatacgaaag ttaggagtta
 781 tgtttccttc actggatacc ctcgtcctgg ccaacaatca tttgaatgct attgaggagc
 841 ctgatgattc attggccagg ttggttccta atcttcgatc catcagcctc cacaggtcag
 901 gtttgcagtc ctgggaagac attgataaac taaattcatt tcccaaactg aagaagtga
 961 gattgttagg aattcctctt ctgcagccat ataccaccga ggagcgaagg aaattggtaa
1021 tagccagatt gccatcagtt tccaaactta atggcagcgt tgttactgat ggtgaacgag
1081 aagattctga gagattttt attcgttact atgtggatgt tccacaggaa gaagtgccat
1141 tcaggtatca tgaactgatc actaaatatg ggaagttgga gcctttgaca gaagtggacc
1201 taagacccca gagcagtgca aaagtagaag tccactttaa cgatcaggtg gaagaaatga
1261 gcattcgtct ggaccaaaca gtggcagaac taaagaaaca gttaaaaact ctagtacaat
1321 tacccacaag caacatgctt ctctactatt ttgaccatga agcacccttt ggcccagagg
1381 aaatgaagta cagctctcgg gcattgcatt ccttttggcat tagggatgga gataaaattt
1441 acgtggaatc caaaacaaaa taacctctac cagccttgtg aaaaacatac acataaggac
1501 ttgttgcagg gcatttgttt ttaatgtggt tttctttagg agggagaggt tgttttttgtt
1561 ttgtttttgtt ctgtttaggt ttgggaagga ttttgtatat ttttccccct ggagtgagta
1621 ggggccattt tgggtgtttt tctaccacag attgatttgg ctcagccagc ggaattggcc
1681 acatttccag tgtatgtgcc ctctctaagg aaagatgaca aagaaatcac cgacttctta
1741 ctgtgttcac tgggatttgc ctgccacgtt ggtatcagta c
//
```

SEQ ID NO: 7
AAR27875.1 GI:38946312
tubulin-specific chaperone cofactor E-like protein [*Homo sapiens*]

```
   1 mdusgrsfm qvlcekyspe nfpyrrgpgm gvhvpatpqg spmkdrinlp svlvinscgi
  61 tcagdekeia afcahvseld lsdnkledwh evskivsnvp qleflnlssn pinlsvlert
 121 cagsfsgvrk lvinnskasw etvhmilgel pdleelflcl ndyetvscps icchslkllh
 181 itdnnlqdwt eirklgvmfp sldtivlann hlnaieepdd slarlvpnlr sislhrsglq
 241 swedidklns fpkleevrll gipllqpytt eerrklviar lpsysklngs vvtdgereds
 301 erffiryyvd vpqeevpfry helitkygkl epltevdlrp qssakvevhf ndqveemsir
 361 ldqtvaelkk qlktivqlpt snmllyyfdh eapfgpeemk yssralhsfg irdgdkiyve
 421 sktk
```

SEQ ID NO: 8
XM 427094.3 GI:513222189
PREDICTED: Gallus gallus tubulin folding cofactor E-like (TBCEL),
transcript variant X2, mRNA

```
   1 acgggggggc tatcacgtga tgtttggttg ctaccgagct gtttccgggt cgatgcggga
  61 cgcggccgcc gggcctggaa gtccaagaaa ggagcatgga ccaacccagt ggcaggagtt
 121 tcatgcaagt tctttgtgag aaatacagcc ctgagaactt cccgtatcgc cgcggccctg
 181 gtatgggtgt gcacgtccca gcaactccac agggctcacc tatgaaagat cgtctcaacc
 241 ttccaagcgt gctggtgctg aacagctgtg gcataacctg tgcagggat gagaacgaga
 301 ttgctgcctt ctgtgctcac gtctccgaac tcgatctttc tgacaataaa ctggaagact
 361 ggcacgaggt cagtaaaatt gtgtccaacg ttcccccactt ggagttttcta aacttgagtt
 421 ccaatcctct cagtttgtcc gttctagaga gaaggtgtgg tgggtccttc gctggtgtcc
 481 gcaaacttgt gctcaacaac agcaaagctt cctgggaaac agtccacaca atcctgcagg
 541 agttacctga cttggaggag ctcttcctgt gccttaatga ctacgaaaca gtgtcttgtt
 601 ctccagtttg ctgtcagtct ctcaaattac tccacataac tgacaataac cttcaagact
 661 ggactgaaat tcgaaaattg gcattatgt ttccatctct ggacacccctt attctggcta
 721 acaacaacct caccaccatc gaagagtcgg aagattccct cgcaaggctg ttccccaacc
 781 tgcgatccat caatttgcac aagtcaggtc tgcattgctg ggaagacatt gacaagttaa
 841 attcgtttcc caagcttgag gaagtgaaat tgctaggaat cccttgctg cagtcctaca
 901 ccactgagga gcgcaggaag ctgctaatag ccaggttgcc atctatcatc aagctcaacg
 961 ggagcattgt tggtgatggg gagcgagagg actcggagcg attcttcatc cgatattaca
1021 tggagttccc agaggaggaa gtcccattca ggtaccacga gctgatcacc aagtatggga
```

US 10,428,093 B2

-continued

SEQUENCE LISTING

```
1081  agctggagcc cttggcagtc gtggatcttc ggccgcagag cagtgtgaag gtggaggttc
1141  acttccagga caaagtagaa gagatgtcaa tccgtcttga tcagactgtg gcagaactga
1201  agaagcactt aaaaactgtg gtgcagctgt caaccagcaa catgctgctc ttctacttgg
1261  accaggaagc ccccttcggc cccgaggaga tgaagtacag ctcacgagca ctgcattcct
1321  atggcattcg ggatggagac aaaatctatg tggagcccag gatgaagtag cctctctcga
1381  cctacacagc ccacacaccc acacacgtgc atttaaggag ttttttgcaag gttttttattt
1441  cggtcagttg gttgaggttt ggttgtgttt ctatagcagg taatggctta gcccggagcg
1501  agtgccctga tgacagaacc atgcccacca cccactgcag gtgacctcgg ggtgacgact
1561  gacttcagtg catgtgtttc cgtgtgtgca atacccccat gttttctttg atgctccggt
1621  atactcgtga tttggcatga gtggtcagtt attgaagctg aagaatgcta gggcccgtaa
1681  gggagaggat ggctcggtgc agaatttgac ctatttattt ctctttctct aaaaaacatg
1741  ggttttttttt ttggcaccat cagagcaccc cagctatcca actgcagttt gagcgagctt
1801  ggttttccat ctgggtgctg tcttgtagcc ttttgtcaca ctcaagctca ctgaaaagat
1861  ctgaaataat gttcagtttg aatcagagct caggtattca gtattcagcg catccactta
1921  gctccactgg ttggtgtgag cgcacaagat gagggaaaga cagggatgct atgagaaaga
1981  aaggatttct tttaaaaact catgcttcta gccatgctgt cttatcagga gtttggaggt
2041  ttgcttttctg tgtccgtgtc acggtgtctg caacctgtag cactgtcagc ctgcaggcaa
2101  agcaagcctg gccctgtaat ttgggaaagg aattgtgggc tggcattgtg ttggaggact
2161  tctaggctag tgggtcagaa atgtggtgag gagtgtgttc ctccattggc taggaaacat
2221  ccctgcgatg ctgaaaggtc ttccaatgag cacttaaccc tgtaccgctg tgtcccgaaa
2281  gtggaatggc tgaaattgct ctcctggag ggagcaagac tcgagttgaa gtttgtttgt
2341  tgttgttgca ccagaaatga aacctggcac ttttccccggg gaccctggc tgcagggtct
2401  ccatttaggg tccaagctag cagaatgtgt tcactaggat cagtttctta gacagcaggt
2461  ccagaagcac ctatacccac gtgtattgta aagcaggtgt tcactagatc ccctccccc
2521  cacatgcacc ttgtaggcat tgtgtgctgc tgcttaaatt agccccccctt ctctaatgca
2581  gcgcagattc ctgtgcgatg aaaccctcag tcctttatat ctcttgtaaa tcagacagcc
2641  gtttcgcttt actctgtcct cccttgttct tctgtcatcc tgacaagctg aagactttttc
2701  aaattacctt cttataagca actgcatcaa cgtttctgtg gctgtgcagt gagggctctg
2761  gttacacgtg aactcctgac cgtgattttg aaatgctccc tgtccccacg tgcactttt
2821  tcccgagatg cttttgtcca cgccaccaag ctcccttata gccttggagt tgtgtattc
2881  tcttcatatt ttacctagat catgggatgg ggtaggatgg gggagggac aaagtattat
2941  ctcgtaatct tcaggttcgg gttgtaggga ccgttgagag gggattagtt ccgcatccac
3001  agtaaggatt aaaaagtggga ggacttaaga caaggtaatt atttctgcct catctccctg
3061  ccaaaaccat ccatctcctg gcaccatcga gacgagcaat agtaaacaga gcaggagtcg
3121  ccataggtag agtagagact acggccatag ctgcagggcc gctgtaccca taaaacacga
3181  gcagggagat ggtggcagtg taccataaga tgatgctttt ataagctaga gctttactga
3241  agatgtattt tccatttggg cagcaaaagg cattttgctg ccttatagcg gaactcttaa
3301  gccaacactt ctgtatgata tatacataga tatgcattgg aaaagttgtg tttaataaga
3361  tatttttgtta taaaacaaag ttttatgaag atatggttgt ttaatattag aagcctattt
3421  ctcccttttga cctcctgttt aagtacatca tccatcggtc gccgcgttgt ccgaattagg
3481  caaccaatgc ggatgcaaag gaatctctga tctaattcta cagagcagta attgcctaca
3541  tggatatgtt tatggcattg taactggtat tagtgagatg ctgtaattac tgaccagctt
3601  gctcagcaca attaaatgtc tcagttgcag acagggaaat aaacaaagtc cattaaagaa
3661  ctaaggggga tattgaagaa gacccagctg taggcttgta ggcttgtttc cccgctaaga
3721  attaccctta tccgcatagg gagcagtgct gccacgctgg ctgggaaccg ccagtaaata
3781  atggctttat ttatggtgga actggtggga actggaagat gaacaaagag gatcgcttgt
3841  tgctttgat gtgacacgc gccgtgtatc accggggatt tggcatcaac acccaaactg
3901  gctcctcggt atgaatgtgt gccttgccat gtcattgagg aaggttgttc ctggacgatg
3961  ttcccaggct gttcaggcag cagcagagcg tgcattaggt ggaaaccaaa agcatccgtt
4021  ggcttcccaa ggagaaagag ccacgtccaa aagccaggaa tgactgacac gtttatgtga
4081  tggacttttga aaagtaggat ggagtggcac gcaaacaacg cgccaggatg tcccgaactg
4141  gattgctttc ctgttgtaat acctgctggg aagggatttt gtgtttgggc aatgttactg
4201  cttaccaggt gtattgggga gagagtgagg gctctgaaca aggggggtcc tggggctggc
4261  attgggcagt gagagtgtcc tgagctggca ggagggtcca tgtcagtcca ttcaatgcca
4321  caaggtgctg cgtcctggct ttgatgcat gcatctgctt tagtgacaga tcccagttct
4381  gccccattcc ttcgagaaaa caaaatacag gcttgcgagc ttctctagct cttgtgttct
4441  tttctcagag tgctacttttt gtcaagaact gttttgttgt tcatgcataa aaatctgctg
4501  tgggcagtct gcacagtgga agaagcacct ggttcgtatg gaattgggta acagctatat
4561  accaaagttt tgcacggctc cgcgtgttga gacgagatgc tgccgcgttg tttttttggg
4621  agacgtcctc attgaatatc catgctttga ccagatgtta caagcctact gctgagccgg
4681  cgatgctatg aatatgcatg gcatggtggc tgtccccct cactgcgatg tgccactgtg
4741  gttggagggg ctcccacgca tcctgctggc caatggcacc atgtggtccc ccaggggctig
4801  gggtggctca gggtccatgc gctcagtcct gtgcggtgct cttgggatcg gctcttggtt
4861  ggccatcgcc tgctgcgctc tgcgatcgct ctgtctccgc cgcttgactt tcctgcttgg
4921  aaatgagatt ctgtaggtgc tgttggtgtg cagattggaa aatgcaaacg atgtgctgaa
4981  agcagcccgg aggctaaaat atgtattcct ggcagctgtg ccaccctcgg tgctcgtgga
5041  gcctttgtag gcagcgggca gacgccgttc ccagcgcggc gctggggcgg ccgcagccat
5101  ctcaggcctc cgccgctgtg attgctgttc tgcacttact ggaaacttca aacatgatt
5161  aaacatgaag gtctattctc gcaccctatt aattatgcat ccgtatgtaa ttctaaagaa
5221  aaagggaaaa ctgtaagtct atatctgttt ttatgctggt ttctctcatg gggattatac
5281  ttcgcgtgcc gacaatttgc ctttggtttg ctcgcagact tagaggtgga attcaggcca
5341  cttaggtcat tggtttggat caattcaata aacctgttta agtttttgca caaaa
```

SEQ ID NO: 9
XP 427094.2 GI:118101919
PREDICTED: tubulin folding cofactor E-like isoform X2 [Gallus Gallus]
  1 mdqpsgrsfm qvlcekyspe nfpyrrgpgm gvhvpatpgg spmkdrinlp svlvinscgi

SEQUENCE LISTING

```
 61 tcagdeneia afcahvseld lsdnkledwh evskivsnvp hleflnlssn plslsvlerr
121 cagsfagvrk lvinnskasw etvhtilgel pdleelflcl ndyetvscsp vccqs1k1lh
181 itdnnlqdwt eirklgimfp sldtlilann nittieesed slarlfpnlr sinlhksglh
241 cwedidklns fpkleevkll gipllqsytt eerrklliar lpsiiklngs ivgdgereds
301 erffiryyme fpeeevpfry helitkygkl eplavvdlrp qssvkvevhf qdkveemsir
361 ldqtvaelkk hlktvvqlst snmllfyldq eapfgpeemk yssralhsyg irdgdkiyve
421 prmk
```

Forward primer:
(SEQ ID NO: 10)
GCTGGATCCATGAAAGACCGTCTCAACCTTCCA

Reverse primer:
(SEQ ID NO: 11)
ACAGAATTCGACTTCATCCTGGGCTCC

SEQ ID NO: 12
Chicken full cell density signal protein with added methionine start sequence, and myc and his tags added on C-terminus M K D
----------------------------------------------------------------
R L N L P S V L V L N S C G I T C A G D E N E I A A F C A H V S E L D L S D
N K L E D W H E V *S K I V S N V P H L E F L N L S S N P L S L S V L E R R C*
*A G S F A G V R K L V L N N S K A S W E T V H T I L Q E L P* D L E E L F L C
L N D Y E T V S C S P V C C Q S L K L L H I T D N N L Q D W T E I R K L G I
M F P S L D T L I L A N N N L T T I E E S E D S L A R L F P N L R S I N L H
K S G *L H C W E D I D K L N S F P K L E E V K L L G I P L L Q S Y T T E E R*
*R K L L I A* R L P S I I K L N G S I V G D G E R E D S E R F F I R Y Y M E F
P E E E V P F R Y *H E L I T K Y G K L E P L A V V D L R P Q S S V K V E V H*
*F Q D K V E E M S I R L D Q T V A E L K K H L K T V V Q L S T S N M L L F Y*
*L D Q E A P F G P E E M K Y S S R A L H S Y G I R D G D K I Y V E P R M K*
----------------------------------------------------------------
S N S A D I Q H S G G R S S L E G P R F E Q K L I S E E D L N M H T G H H H
H H H SEQ ID NO: 13
Chicken 94 aa cell density signal with an added methionine start sequence, and myc and his tags added on C-terminus M
----------------------------------------------------------------
*E P L A V V D L R P Q S S V K V E V H F Q D K V E E M S I R L D Q T V A E L*
*K K H L K T V V Q L S T S N M L L F Y L D Q E A P F G P E E M K Y S S R A L*
*H S Y G I R D G D K I Y V E P R M K*
----------------------------------------------------------------
D D D D K K G E F E A Y V E Q K L I S E E D L N S A V D H H H H H H SEQ ID: 14
DNA sequence which expresses Chicken cell density protein
Exons 2-7

```
cgtctcaaccttccaagcgtgctggtgctgaacagctgtggcataacctgtgcaggggat
 R   L   N   L   P   S   V   L   V   L   N   S   C   G   I   T   C   A   G   D
gagaacgagattgctgccttctgtgctcacgtctccgaactcgatctttctgacaataaa
 E   N   E   I   A   A   F   C   A   H   V   S   E   L   D   L   S   D   N   K
ctggaagactggcacgaggtcagtaaaattgtgtccaacgttccccacttggagtttcta
 L   E   D   W   H   E   V   S   K   I   V   S   N   V   P   H   L   E   F   L
aacttgagttccaatcctctcagtttgtccgttctagagagaaggtgtgctgggtccttc
 N   L   S   S   N   P   L   S   L   S   V   L   E   R   R   C   A   G   S   F
gctggtgtccgcaaacttgtgctcaacaacagcaaagcttcctgggaaacagtccacaca
 A   G   V   R   K   L   V   L   N   N   S   K   A   S   W   E   T   V   H   T
atcctgcaggagttacctgacttggaggagctcttcctgtgccttaatgactacgaaaca
 I   L   Q   E   L   P   D   L   E   E   L   F   L   C   L   N   D   Y   E   T
gtgtcttgttctccagtttgctgtcagtctctcaaattactccacataactgacaataac
 V   S   C   S   P   V   C   C   Q   S   L   K   L   L   H   I   T   D   N   N
cttcaagactggactgaaattcgaaaattgggcattatgtttccatctctggacaccctt
 L   Q   D   W   T   E   I   R   K   L   G   I   M   F   P   S   L   D   T   L
attctggctaacaacaacctcaccaccatcgaagagtcggaagattccctcgcaaggctg
 I   L   A   N   N   N   L   T   T   I   E   E   S   E   D   S   L   A   R   L
ttccccaacctgcgatccatcaatttgcacaagtcaggtctgcattgctgggaagacatt
 F   P   N   L   R   S   I   N   L   H   K   S   G   L   H   C   W   E   D   I
gacaagttaaattcttttcccaagcttgaggaagtgaaattgctaggaattcccttgctg
 D   K   L   N   S   F   P   K   L   E   E   V   K   L   L   G   I   P   L   L
cagtcctacaccactgaggagcgcaggaagctgctaatagccaggttgccatctatcatc
 Q   S   Y   T   T   E   E   R   R   K   L   L   I   A   R   L   P   S   I   I
aagctcaacggagcattgttggtgatggggagcgagaggactcggagcgattcttcatc
 K   L   N   G   S   I   V   G   D   G   E   R   E   D   S   E   R   F   F   I
```

SEQUENCE LISTING

```
cgatattacatggagttcccagaggaggaagtcccattcaggtaccacgagctgatcacc
 R   Y   Y   M   E   F   P   E   E   E   V   P   F   R   Y   H   E   L   I   T
aagtatgggaagctggagcccttggcagtcgtggatcttcggccgcagagcagtgtgaag
 K   Y   G   K   L   E   P   L   A   V   V   D   L   R   P   Q   S   S   V   K
gtggaggttcacttccaggacaaagtagaagagatgtcaatccgtcttgatcagactgtg
 V   E   V   H   F   Q   D   K   V   E   E   M   S   I   R   L   D   Q   T   V
gcagaactgaagaagcacttaaaaactgtggtgcagctgtcaaccagcaacatgctgctc
 A   E   L   K   K   H   L   K   T   V   V   Q   L   S   T   S   N   M   L   L
ttctacttggaccaggaagccccttcggccccgaggagatgaagtacagctcacgagca
 F   Y   L   D   Q   E   A   P   F   G   P   E   E   M   K   Y   S   S   R   A
ctgcattcctatggcattcgggatggagacaaaatctatgtggagcccaggatgaag
 L   H   S   Y   G   I   R   D   G   D   K   I   Y   V   E   P   R   M   K
```

Forward primer:
(SEQ ID NO: 15)
GTGACCATGGAGCCCTTGGCAGTCGTGGAT

Reverse primer:
(SEQ ID NO: 16)
CTTATCGTCATCGTCCTTCATCCTGGGCTC

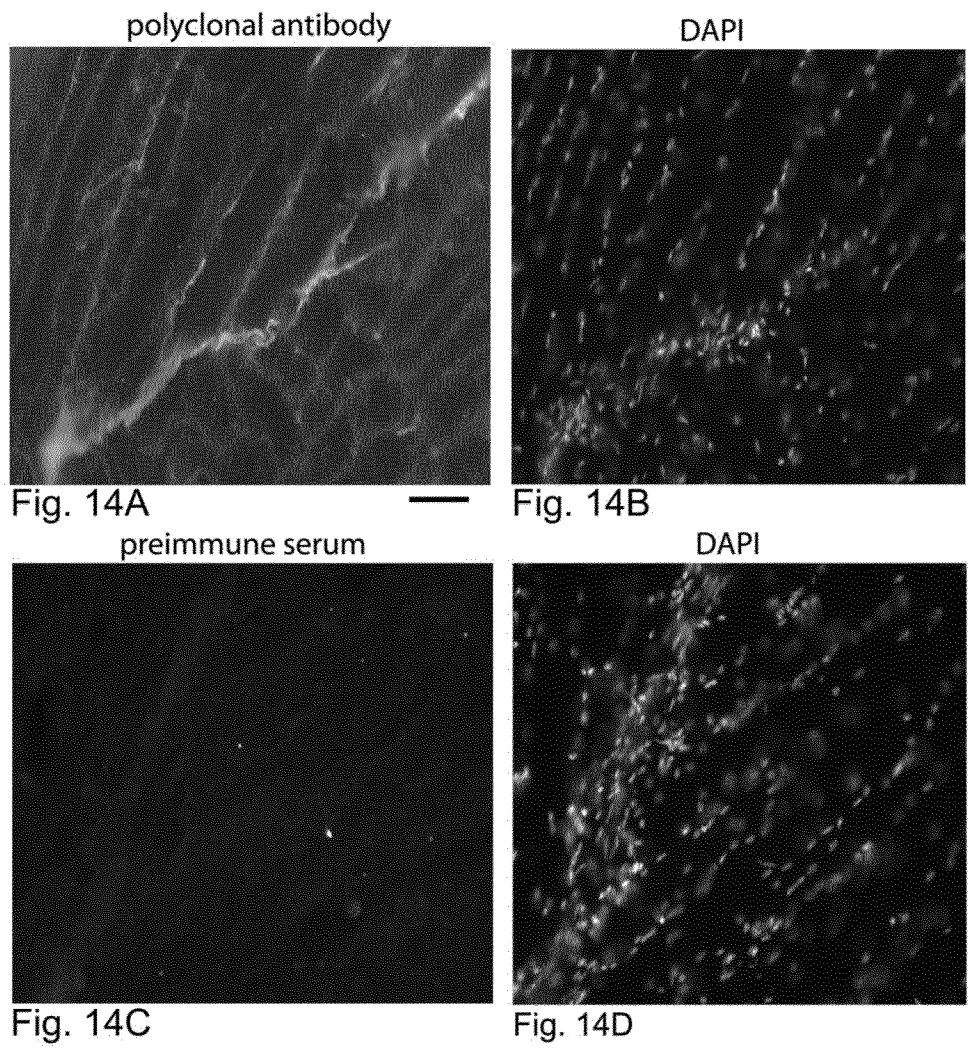

What is claimed is:

1. An isolated tissue-specific lipid co-factor having a formula C63H123N2O11P and a mass of about 1114.89 MW, said lipid cofactor binds to a polypeptide factor that comprises the amino acid sequence set forth in SEQ ID NO: 3 or SEQ ID NO: 5 to form a protein/lipid cell density signaling complex, said cell density signally complex controlling cell proliferation, differentiation or apoptosis in bone and cartilage tissue, and said lipid co-factor comprising a ceramide phosphate, a glycerol lipid with a single fatty acid, and a linker.

2. An isolated tissue-specific lipid co-factor having a formula C30H74NO5P and a mass of about 696.65 MW, said lipid cofactor binds to a polypeptide factor that comprises the amino acid sequence set forth in SEQ ID NO: 3 or SEQ ID NO: 5 to form a protein/lipid cell density signaling complex; said cell density signally complex controlling cell proliferation, differentiation or apoptosis in tendon tissue and said lipid co-factor comprising two fatty acid chains connected directly to a phosphate molecule.

3. A method of isolating the lipid co-factor of claim 1 or 2 comprising:
   a. filtering conditioned medium containing said protein lipid complex through a 0.2 micron filter;
   b. adding 5M NaCl in an amount equivalent to $1/10^{th}$ the resulting conditioned medium volume;
   c. using an ultrafilter in a stirred cell under pressurized nitrogen to concentrate the high salt conditioned medium to 1 ml of retentate;
   d. diluting the retentate to 10 ml with water and reconcentrating to 0.5 ml;
   e. capturing the free protein factor in the retentate; and,
   f. capturing the free lipid cofactor in the filtrate.

4. A cell density signaling complex comprising a tissue-specific lipid cofactor of claim 1 or 2, which is tightly bound to a polypeptide factor that comprises the amino acid sequence set forth in SEQ ID NO: 3 or SEQ ID NO: 5.

* * * * *

UNITED STATES PATENT AND TRADEMARK OFFICE
CERTIFICATE OF CORRECTION

PATENT NO. : 10,428,093 B2
APPLICATION NO. : 15/137448
DATED : October 1, 2019
INVENTOR(S) : Richard I. Schwarz It is certified that error appears in the above-identified patent and that said Letters Patent is hereby corrected as shown below:

In the Drawings

Please replace FIGS. 1A-16B with FIGS. 1A-16B as shown on the attached pages.

Signed and Sealed this
Fourth Day of February, 2020

Andrei Iancu
*Director of the United States Patent and Trademark Office*

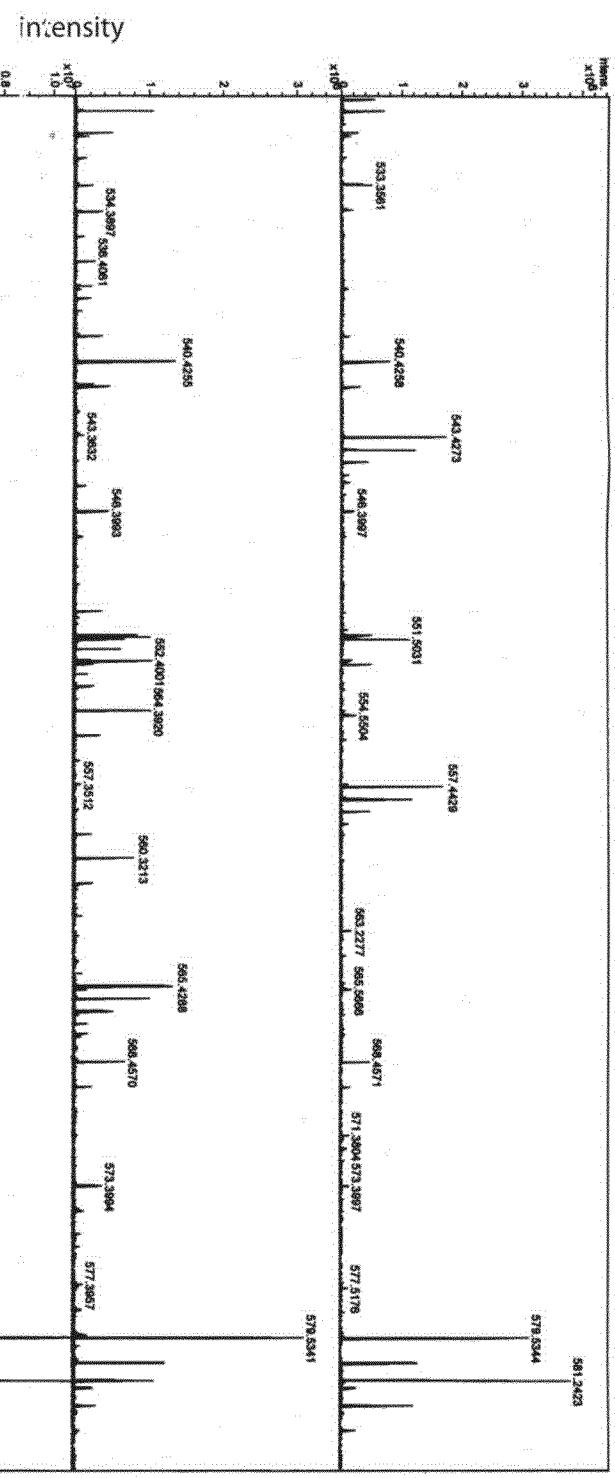
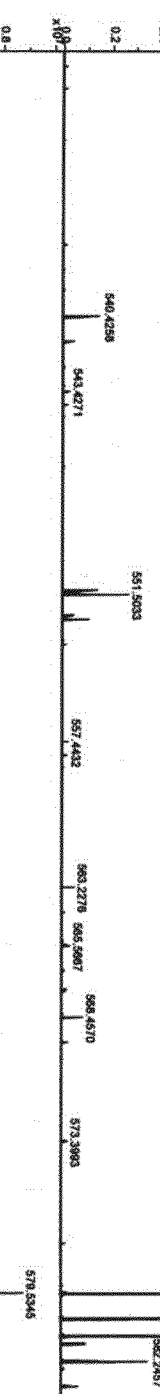
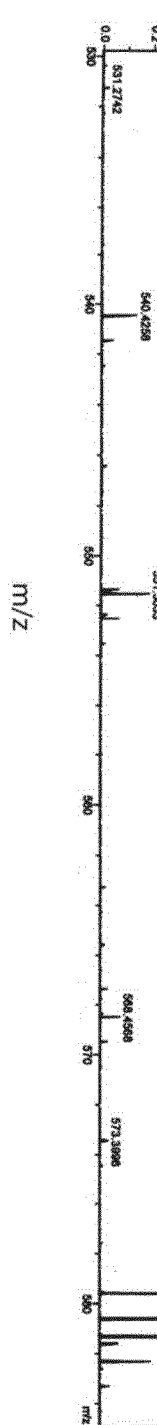
Fig. 8A untreated cofactor
Fig. 8B phospholipase C
Fig. 8C lipase
Fig. 8D no cofactor buffer only

Figure 13B:
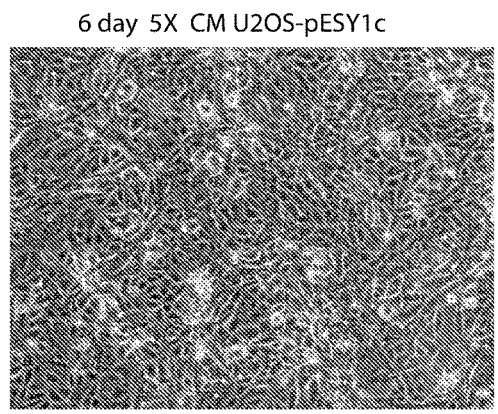
Figure 13C:
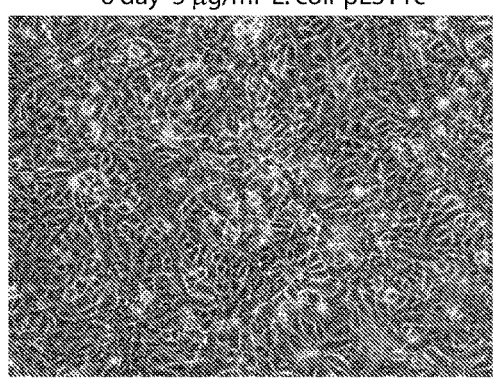
Figure 13D:
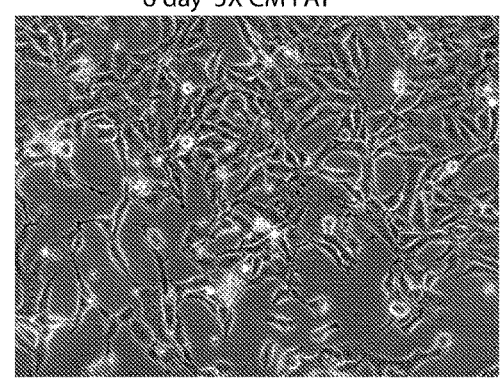
Figure 13E:
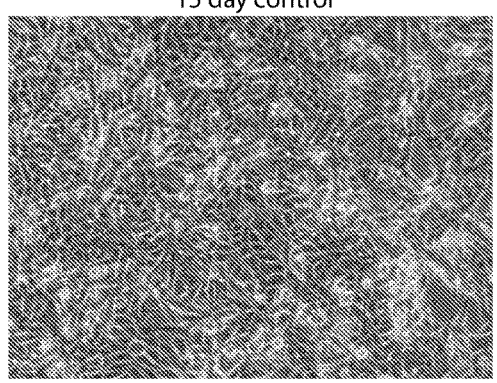
Figure 13F:
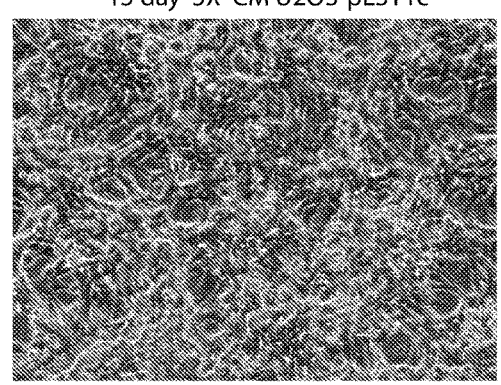

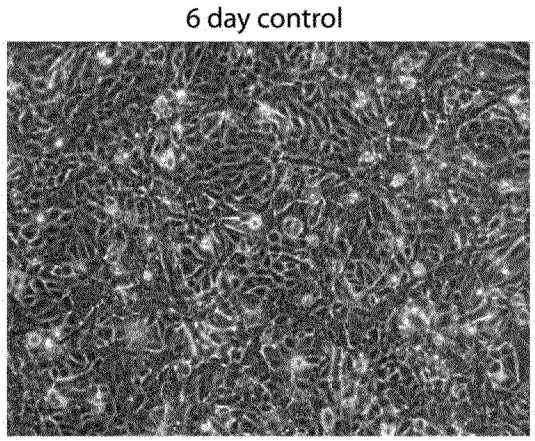
Fig. 13A — 6 day control
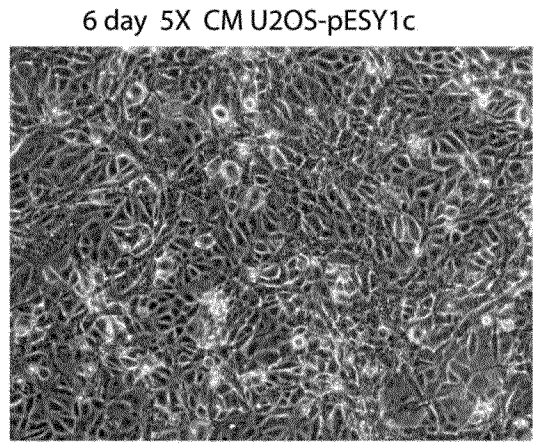
Fig. 13B — 6 day 5X CM U2OS-pESY1c
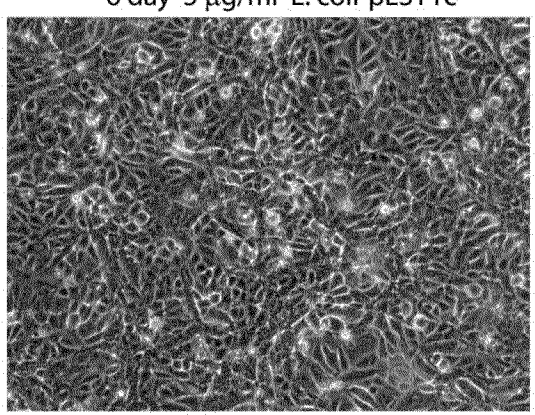
Fig. 13C — 6 day 5 µg/ml E. coli-pESY1c
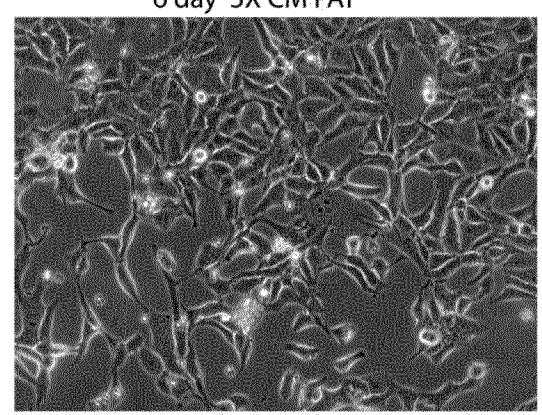
Fig. 13D — 6 day 5X CM PAT
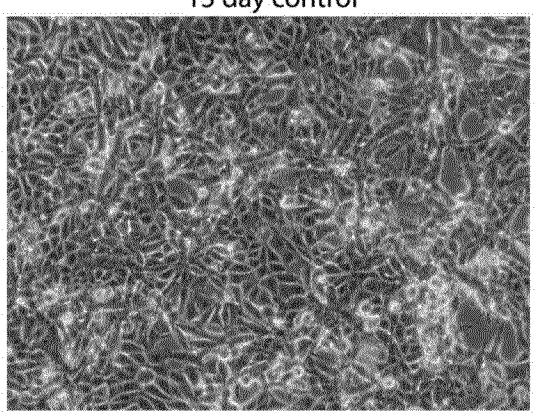
Fig. 13E — 15 day control
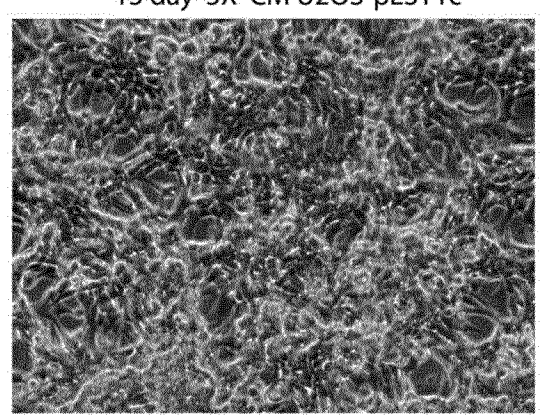
Fig. 13F — 15 day 5X CM U2OS-pESY1c